United States Patent
Hogg

(10) Patent No.: US 9,353,152 B2
(45) Date of Patent: May 31, 2016

(54) INDUCTION OF THE MITOCHONDRIAL PERMEABILITY TRANSITION

(71) Applicant: NewSouth Innovations Pty Limited, UNSW Sydney (AU)

(72) Inventor: Philip John Hogg, Randwick (AU)

(73) Assignee: NewSouth Innovations Pty Limited, Sydney (AU)

(*) Notice: Subject to any disclaimer, the term of this patent is extended or adjusted under 35 U.S.C. 154(b) by 0 days.

(21) Appl. No.: 14/063,748

(22) Filed: Oct. 25, 2013

(65) Prior Publication Data

US 2014/0121165 A1 May 1, 2014

Related U.S. Application Data

(63) Continuation of application No. 10/534,922, filed as application No. PCT/AU03/01483 on Nov. 7, 2003, now abandoned.

(30) Foreign Application Priority Data

Nov. 7, 2002 (AU) .................................. 2002952526
Nov. 5, 2003 (AU) .................................. 2003906109

(51) Int. Cl.

| | | |
|---|---|---|
| *A61K 31/555* | (2006.01) |
| *C07K 7/06* | (2006.01) |
| *A61K 31/285* | (2006.01) |
| *G01N 33/50* | (2006.01) |
| *G01N 33/574* | (2006.01) |
| *G01N 33/68* | (2006.01) |
| *C07F 9/78* | (2006.01) |
| *C07F 9/80* | (2006.01) |
| *C07F 9/82* | (2006.01) |
| *C07F 5/06* | (2006.01) |
| *C07K 5/08* | (2006.01) |

(52) U.S. Cl.
CPC ............... *C07K 7/06* (2013.01); *A61K 31/285* (2013.01); *C07F 5/06* (2013.01); *C07F 9/78* (2013.01); *C07F 9/803* (2013.01); *C07F 9/82* (2013.01); *C07K 5/08* (2013.01); *G01N 33/5011* (2013.01); *G01N 33/5079* (2013.01); *G01N 33/574* (2013.01); *G01N 33/6872* (2013.01); *G01N 2333/515* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 2,370,092 A | 2/1945 | Tillitson |
| 2,409,291 A | 10/1946 | Lott et al. |
| 2,465,308 A | 3/1949 | Herman et al. |
| 2,553,515 A | 5/1951 | Herman et al. |
| 2,664,432 A | 12/1953 | Friedheim |
| 2,951,766 A | 9/1960 | White |
| 3,883,650 A | 5/1975 | Friedheim et al. |
| 5,270,196 A | 12/1993 | Sawada et al. |
| 5,281,588 A | 1/1994 | Maes et al. |
| 5,459,263 A | 10/1995 | Floc'H et al. |
| 7,074,766 B1 | 7/2006 | Hogg et al. |
| 7,186,695 B2 | 3/2007 | Hogg |
| 7,498,406 B2 | 3/2009 | Hogg et al. |
| 2001/0044144 A1 | 11/2001 | Anderson et al. |
| 2005/0101524 A1 | 5/2005 | Hogg et al. |
| 2007/0037995 A1 | 2/2007 | Hogg et al. |
| 2007/0037996 A1 | 2/2007 | Hogg et al. |

FOREIGN PATENT DOCUMENTS

| | | | |
|---|---|---|---|
| FR | 2781674 | 7/1998 | |
| WO | WO 98/51297 | 11/1998 | |
| WO | WO 99/18798 | 4/1999 | |
| WO | WO 99/55344 | 11/1999 | |
| WO | WO 00/56742 | 9/2000 | |
| WO | WO 00/79274 | 12/2000 | |
| WO | WO 01/21628 | * 3/2001 | ............... C07F 9/20 |
| WO | WO 02/074305 | 9/2002 | |
| WO | WO 03/003011 | 1/2003 | |
| WO | WO 03/039564 | 5/2003 | |
| WO | WO 2004/042079 | 5/2004 | |
| WO | WO 2008/052279 | 5/2008 | |

OTHER PUBLICATIONS

Ades et al., "HMEC-1: Establishment of an Immortalized Human Microvascular Endothelial Cell Line," The Journal of Investigative Dermatology, vol. 99, No. 6 (1992) pp. 683-690.
Andre et al., "Binding of Vascular Anticoagulant a (VACa) to Planar Phospholipid Bilayers," J. Bio. Chem., vol. 265, No. 9 (1990) pp. 4923-4926.
Blankenberg et al., "Will Imaging of Apoptosis Play a Role in clinical Care? A tale of Mice and Men," Apoptosis, vol. 6 (2001) pp. 117-123.
Dahmoun et al., "Apoptosis, Proliferation, and Sex Hormone Receptors in Superficial Parts of Human Endometrium at the End of the Secretory Phase," The Journal of Clinical Endocrinology & Metabolism, vol. 84, No. 5 (1999) pp. 1737-1743.
Daly et al., "Neu Differentiation Factor Induces ErbB2 Down-regulation and Apoptosis of ErbB2-Overexpressing Breast Tumor Cells," Cancer Research, vol. 57 (1997) pp. 3804-3811.
Donoghue et al., "Presence of Closely Spaced protein Thiols on the Surface of Mammalian Cells," protein Science, vol. 9 (2000) pp. 2436-2445.
Fisher et al., "Coloning and Expression of Human Tissue Factor cDNA," Thrombosis Research, vol. 38 (1987) pp. 89-99.
Gottlieb et al., "Apoptosis in Myocardial Ischemia-Reperfusion," Ann. N.Y. Acad. Sci., vol. 874 (1999) pp. 412-426.

(Continued)

*Primary Examiner* — Craig Ricci
(74) *Attorney, Agent, or Firm* — McDonnell Boehnen Hulbert & Berghoff LLP

(57) ABSTRACT

The present invention relates to process for identifying a compound which induces the mitochondrial permeability transition (MPT) in proliferating cells, wherein said process comprises contacting a cell or cell extract with a compound, determining whether the compound binds to adenine nucleotide translocator (ANT), and determining whether the compound selectively induces the MPT in proliferating cells.

2 Claims, 29 Drawing Sheets

(56) References Cited

OTHER PUBLICATIONS

Hofstra et al., "Visualisation of Cell Death in vivo in Patients with Acute Myocardial Infarction," The lancet, vol. 356 (2000) pp. 209-212.
Huang et al., "Tumor Infraction in Mice by Antibody-Directed Targeting of Tissue Factor to Tumor Vasculature," Science, vol. 275 (1997) pp. 547-550.
Jiang et al., "Redox Control of Exofacial protein Thiols/Disulfides by protein Disulfide Isomerase," J. Bio. Chem., vol. 274, No. 4 (1999) pp. 2416-2423.
Ju et al., "Molecular and Cellular Mech Regulating T and B Cell Apop Through Fax/FasL Interaction," Intern, Rev. Immunol., vol. 18 (1999) pp. 485-513.
Krams et al., "Apoptosis as a Mechanism of Tissue Injury in Liver Allograft Rejection," Seminars in Liver Disease, vol. 18, No. 2 (1998) pp. 153-167.
Nihei et al., Pharmacologic properties of Pzz/P2X7 Receptor Characterized in murine Dendritic Cells: role on the Induction of Apoptosis,: Blood, vol. 96, No. 3 (2000) pp. 996-1004.
O'Reilly et al., "Angiostatin: A novel Angiogensis Inhibitor That Mediates the Suppression of Metastases by a Lewis Lung Carcinoma," Cell, vol. 79 (1994) pp. 315-328.
Parker et al., "The Role of Apoptosis in the Pathogenesis of the Myelodysplastic Syndromes," Int. J. Hematol., vol. 73 (2001) pp. 416-428.
Ramachandran et al., "Apoptosis in the Intestinal Epitheliam: Its Relevance in Normal and Pathophysiological Conditions," Journal of Gastroenterology and Hepatology, vol. 15 (2000) pp. 109-120.
Riddles et al., "Reassessment of Ellman's Reagent," Methods in Enzymology, vol. 91 (1983) pp. 50-61.
Rimon et al., "Rapid Communication: Increased Surface Phosphatidylserine Is an Early Marker of Neuronal Apoptosis," Journal of Neuroscience Research, vol. 48 (1997) pp. 563-570.
Rupnow et al., "The Role of Radiation-Induced Apoptosis as a determinant of tumor Responses to radiation Therapy," Apoptosis, vol. 4, No. 2 (1999) pp. 115-143.
Stefanec, "Endothelial Apoptosis, Could it Have a Role in the pathogenesis and Treatment of a Disease?," Chest, vol. 117, No. 3 (2000) pp. 841-854.
Stone et al., "Recombinant Soluble Human Tissue Factor Secreted by *Saccharomyces cerevisiae* and Refolded from *Escherichia coli* Inclusion Bodies: Glycosylation of Mutants, Activity and Physical Characterization," Biochem J., vol. 310 (1995) pp. 605-614.
Thompson, "Apoptosis in the pathogenesis and Treatment of Disease," Science, vol. 267 (1995) pp. 1456-1462.
Vermes et al., "A Novel Assay for Apoptosis Flow Cytomertic Detection of Physhatidylserine Expression on Early Apoptoic Cells Using Fluorescein labeled Annexin V," Journal of Immunological Methods, vol. 184 (1995) pp. 39-51.
Virginio et al., "Kinetics of Cell Lysis, Dye Uptake and Permeability Changes in Cells Expressing the Rat P2X7 Receptor," Journal of Physiology, vol. 519 (1999) pp. 335-346.
Weissleder et al., "In Vivo Imaging of tumors with Protease-Activated Near-Infrared Fluorescent Probes," Nature Biotechnology, vol. 17 (1999) pp. 375-378.
Adams et al., "Chemistry of Organometalloid Complexes with potential Antidotes: Structure of an organoarsenic(III) Dithiolate Ring," Inorg. Chem., vol. 29 (1990) pp. 1500-1503.
Greenberg et al., "Prostate Cancer in a Transgenic Mouse," PNAS, vol. 92 (1995) pp. 3439-3443.
Hofstra et al., "In Vivo Detection of Apoptosis in an Intracardiac Tumor," JAMA, vol. 285, No. 14 (2001) pp. 1841-1842.
Kaufmann, "Cell Death Induced by Topoisonmerase-targeted Drugs: More Questions Than Answers," Biochimica et Biophysica Acta, vol. 1400 (1998) pp. 195-211.
Mattson, "Apoptosis in Neurodegenerative Disorders," National Review/Molecular Cell Biology, vol. 1 (2000) pp. 120-129.
Novia, "Protein Disulfide Isomerase: The Multifunctional Redox Chaperone of the Endoplasmic Reticulum," Cell & Developmental Biology, vol. 10 (1999) pp. 481-493.
Pronk et al., "Requirement of an ICE-Like Protease for Induction of Apoptosis and Ceramide Generation by Reaper," Science, vol. 271 (1996) pp. 80-810.
Thronberry et al., "Caspases: Enemies Within," Science, vol. 281 (1998) pp. 1312-1316.
Zhu et al, "An ICE-Like Protease is a Common Mediator of Apoptosis Induced by Diverse Stimuli in Human Monocytic THP .1 Cells," FEBS Letters, vol. 374 (1995) pp. 303-308.
Bazarbachi et al., "Aresenic Trioxide and Interferon-a Synergize to Induce Cell Cycle Arrest and Apoptosis in Human T-Cell Lymphotropic Virus Type I-Transformed Cells," Blood, vol. 93, No. 1 (1999) pp. 278-283.
Gitler et al., "General Method to Identify and Enrich Vicinal Thiol Proteins Present in Intact Cells in the Oxidized, Disulfide State," Analytical Biochemistry, vol. 252 (1997) pp. 48-55.
Cai et al., "Mitochondrial Control of Apoptosis: the role of cytochrome c," Biochimica et Biophysica Acta, vol. 1366, p. 139-148, 1998.
Evtodienko et al., "Mechanisms of the Resistance to the Mitochondrial Permeability Transition in Tumor Cells," Pathophysiology, 1999, pp. 171-178.
Korge et al., "Phenylarsine oxide induces mitochondrial permeability transition, hypercontracture, and cardiac cell death," Am J. Physiol. Heart Circ. Physiol., 2001, vol. 280, pp. H2203-H2213.
Costantini et al., "Modulation of the mitochondrial permeability transition pore by pyridine nucleotides and dithiol oxidation at two separate sites," The Journal of Biological Chemistry, 1996, vol. 271, No. 12, pp. 6746-6751.
McStay et al., "Role of critical thiol groups on the matrix surface of the adenine nucleotide translocase in the mechanism of the mitochondrial permeability transition pore," Biochem J., 2002, vol. 367, pp. 541-548.
Hortelano et al., "Nitric oxide induces apoptosis via triggering mitochondrial permeability transition," FEBS Letters, 1997, vol. 410, pp. 373-377.
Balakirev et al., "Gradual changes in permeability of inner mitochondrial membrane precede the mitochondrial permeability transition," Archives of Biochemistry and Biophysics, 1998, vol. 356, No. 1, pp. 46-54.
Costantini et al., "Oxidation of a critical thiol residue of the adenine nucleotide translocator enforces Bci-2-independent permeability transition core opening and apotopsis," Oncogene, 2000, vol. 19, pp. 307-314.
Don et al., "A peptide trivalent arsenical inhibits tumor angiogenesis by perturbing mitochondrial function in angiogenic endothelial cells," Cancer Cell, 2003, vol. 3, pp. 497-509.
Al-Nasser, I.A., "In vivo prevention of adriamycin cardiotoxicity by cyclosporin a or FK506," Toxicology, 1998, vol. 131, pp. 175-181.
Sieburg, "Aus dem Institut fur Pharmakologie und physiologische Chemie der Universitat zu Rostock, Ueber Ester aromatischer Arsenverbindungen (der p-Benzarsinsaure) mit Aminosauren und hoheren Alkoholen," Zur Biologie aromatischer Arsenverbindungen, Ztschr. f. physiol. Chem., 1916, 97, Heft 2/3, 224-245.
Reiter et al., "Pathogenesis, diagnosis and monitoring of residual disease in acute promyelocytic leukemia," Acta Haematol., 2004, vol. 112, 55-67.
Vey et al., "Arsenic trioxide for the treatment of myelodysplastic syndromes," Expert Opin. Pharmacother., 2004, vol. 5, 613-621.
Fairlamb, et al., "Trypanothione is the Primary Target for Arsenical Drugs Against African Trypanosomes," PNAS, vol. 86 (1989) pp. 2607-2611.
Hummel et al., "Modification of Bovine Pancreatic Ribonuclease A with the Site-Specific Reagent 4-Arsono-2-nitrofluorobenzene. Spectrophotometric Titration of Arsononitrophenyl Ribonuclease A Derivatives", Biochemistry, 1981, vol. 20, 4843-4852.
Hummel et al., "Chemical modification of ribonuclease A with 4-arsono-2-nitrofluorobenzene", Int. J. Peptide Protein Res., 1984, vol. 24, 1-13.

(56) References Cited

OTHER PUBLICATIONS

Delnomdedieu et al., "Reduction and binding of arsenate and dimethylarsinate by glutathione: a magnetic resonance study", Chemico Biological Interactions, 1994, vol. 90, 139-155.
Donoghue, N. et al., "Characterization of Redox-Active Proteins on Cell Surface", Methods in Enzymology, 2002, vol. 348, 76-86.
Hnatowich, DJ et al., "Investigations of Avidin and Biotin for Imaging Applications", 1987, The Journal of Nuclear Medicine, vol. 8, 1294-1302.
Gill, B.S., "Chemotherapeutic Susceptibility of Trypanosoma to some Arsenicals and Suramin-Tryparsamid Complex", Acta Vet., 1971, 40(2), 209-14. (English Abstract only).
Yuki, H. et al., "Synthesis of Purine and Pyrmidine Derivatives of Arsonic Acid", Chem. Pharm. Bull., 1967, 15(7), 1052-1055.
Donahue, N. et al., [9] Identification of Redox-Active Proteins on Cell Surface, Methods of Enzymology, vol. 352, 101-112.
Namgung et al., "Arsenite-Induced Apoptosis in Cortical Neurons is Mediated by c-Jun N-Terminal Protein Kinase 3 and p38 Mitogen-Activated Protein Kinase", The Journal of Neuroscience 2000, 20(7), 6442-6451.
Loiseau et al., "Contribution of Dithiol Ligands to In Vitro and In Vivo Trypanocidal Activities of Dithiaarsanes and Ivestigation of Ligand Exchange in an Aqueous Solution", Antimicrobial Agents and Chemotherapy, 2000, 44(11) 2954-2961.
Gorman et al., "The Hype and the Hope", Time, 1998, 151(19), 40-44. Included HTML Copy referenced pp. 1-9.
Gura, T., "Systems for Identifying New Drugs are Often Faulty", Science, 1997, 278(7), 1041-1042.
Dermer, GB, "Another Anniversary for the War on Cancer", Bio/Technology, Mar. 12, 1994, vol. 12, p. 320.
McKie, R., "Cancer Research Set Back a Decade", The Observer, Jun. 10, 2001, 1-4.
Definition of Cancer. Internet document <<http://www.medterms.com>> 1 page, accessed Sep. 16, 2005, last reviewed Sep. 18, 2004.
Chemical Abstracts Registry No. 1112-90-3. p-amino phenyl arsenoxide.
Chemical Abstracts Registry No. 637-03-6. Arsenosobenzene.
Rudinger, J., "Characteristics of the amino acids as components of a peptide hormone sequence", In: Peptide Hormones, JA Parsons, Ed., 1976, 1-7.
Voet et al., "Chapter 9. Hemoglobin: Protein Function in Microcosm, Section 9-3. Abnormal Hemoglobins", Biochemistry, 2nd Edition, 1995, 235-241.
Smilek et al., "A Single amino acid change in a myelin basic protein peptide confers the capacity to prevent rather than induce experimental autoimmune encephalomyelitis", Proc. Natl. Acad. Sci., 1991, vol. 88, 9633-9637.
Banks et al., "Biomolecules Bearing the S- or SeAsMe2 Function: Amino Acid and Steroid Derivatives", Journal of Medicinal Chemistry, 1979, 22(5), 572-575.
Fairlamb, et al., "Metabolism and Functions of Trypanothione in the Kinetoplastida," Annu. Rev. Microbiol., vol. 46 (1992) pp. 695-729.
Cunningham, et al., "mechanism of inhibition of Trypanothione Reductase and Glutathione Reductase by Trivalent Organic Arsenicals," FEBS, vol. 221 (1994) pp. 285-295.
Bhargava, et al., "Effect of Arsenical Drugs on Glutathione metabolism of Litomosoides Carinii," Molecular and biochemical Parasitology, vol. 9 (1983) pp. 29-35.
Carter, et al., "Arsenical-Resistant Trypanosomes lack an Unusual Adenosine Transporter," Nature, vol. 361 (1993) pp. 173-176.
Pisciotto, et al., "Induction of Mucosal Glutathione Synthesis by Arsenic," Biochemica et Biophysica Acta, vol. 628 (1980) pp. 241-243.
Lawrence et al., "Surface Thiols of Human Lymphocytes and Their Changes after In Vitro and in Vivo Activation," Journal of Leukocyte Biology, vol. 60, (1996) pp. 611-618.
Ryser et al., "Cell Surface Sulfhydryls are Required for the Cytotoxicity of Diphtheria Toxin but not of Ricin in Chinese Hamster Ovary Cells," Journal of biological Chemistry, vol. 266, No. 28 (1991) pp. 18439-18442.
Mandel et al., "Inhibition of a Reductive Function of the Plasma Membrane by Bacitracin and Antibodies Against Protein Disulfide-Isomerase," PNAS, vol. 90 (1993) pp. 4112-4116.
Couet et al., "Cell Surface Protein Disulfide-Isomerase is involved in the Shedding of Human Thyrotropin Receptor Ectodomain," Biochemistry, vol. 35 (1996) pp. 14800-14805.
Krishna et al, "cDNA for R-Cognin: Homology with a Multifunctional protein," PNAS, vol. 90 (1993) pp. 2950-2954.
Zai et al., "Cell-Surface Protein Disulfide Isomerase Catalyzes Transnitrosation and Regulates Intracellular Transfer of nitric Oxide," The Journal of Clinical Investigation, vol. 103, No. 3 (1999) pp. 393-399.
Essex et al., "Localization of Protein Disulfide Isomerase to the External Surface of the Platelet Plasma Membrane," Blood, vol. 86, No. 6 (1995) pp. 2168-2173.
Essex et al., "Protein Disulphide Isomerase Mediates Platelet Aggregation and Secretion," British Journal of Haematology, vol. 104 (1999) pp. 448-454.
Tager et al., "Membrane-Bound proteindisulfide isomerase (PDI) is Involved in Regulation of Surface Expression of Thiols and Drug Sensitivity B-CLL Cells," Experimental Hematology, vol. 25 (1197) pp. 601-607.
Stathakis et al., "Generation of Angiostatin by Reduction and Proteolysis of Plasmin: Catalysis by a Plasmin Reductase Secreted by cultured Cells," J. Bio. Chem., vol. 272, No. 33 (1997) pp. 20641-20645.
Stathakis et al., Angiostatin Formation Involves Disulfide Bond Reduction and Proteolysis in Kringle 5 of Plasmin, J. Bio. Chem., vol. 274, No. 13 (1999) pp. 8910-8916.
Bannai et al., "The Export of Glutathione from Human Diploid Cells in Culture," J. Bio. Chem., vol. 254, No. 9 (1979) pp. 3444-3450.
Holmgren et al., "Thioredoxin and Glutaredoxin Systems," J. Bio. Chem., vol. 264, No. 24 (1989) pp. 13963-13966.
Rosen et al., "A CD4+ T Cell Line-Secreted Factor, Growth, Promoting for Normal and Leukemic B Cells, Identified as Thioredoxin," International Immunology, vol. 7, No. 4 (1995) pp. 625-633.
Happersberger et al., "A Mass Spectrometic Approach to the Characterization of Protein Folding Reactions," Eur. Mass Spectrom, vol. 4 (1998) pp. 209-214.
Halestrap et al., "The Permeability Transition Pore Complex: Another View," Biochimie, vol. 84 (2002) pp. 153-166.
Desagher et al., "Mitochondria as the Central Control Point of Apoptosis," Trends in Cell Biology, vol. 10 (2000) pp. 369-377.
Fantin et al., "A Novel Mitochondriotoxic Small Molecule that Selectively inhibits Tumor Cell Growth," Cancer Cell, vol. 2 (2002) pp. 29-42.
Belzacq et al., "The Adenine Nucleotide Translocator in Apoptosis," Biochimie, vol. 84 (2002) pp. 167-176.
McStay et al., "Role of Critical Thiol Groups on the Matrix Surface of the Adenine Nucleotide Translocase in the Mechanism of the Mitochondrial Permeability Transition Pore," Biochem. J., vol. 367 (2002) pp. 541-548.
Koch, "The Role of Angiogensis in Rheumatoid Arthritis: Recent Developments," Ann. Rheum. Dis., vol. 59 (2000) pp. 65-71.
Hayes, "Angioneogenesis in Rheumatoid Arthritis," The Lancet, vol. 354 (1999) pp. 423-424.
Anonymous, "Arthritis: The Aging Populations of Developed Countries are Likely to present a Growing market for Arthritis Therapies," Nature Biotechnology, vol. 18 (2000) pp. IT12-IT14.
Wolff et al., "Imatinib mesylate efficiently achieves therapeutic intratumor concentrations in vivo but has limited activity in a xenograft model of small cell lung cancer," Clin. Cancer Res., 2004, vol. 10, 3528-3534.
U.S. Appl. No. 12/513,159, filed Apr. 30, 2009.
Allen et al., "The mounse Bcrp/Mxr/Abcp gene: amplification and overexpression in cell lines selected for resistance to topotecan, mitoxantrone, or doxorubicin," Cancer Res., 1999, vol. 59, 4237-4241.
Dilda et al., "Para to ortho repositioning of the arsenical moiety of the angiogenesis inhibitor 4-(N-(S-glutathionylacetyl)amino)phenylarsenoxide results in a markedly increaded cellular accumulation and anti-proliferative activity," Cancer Res., 2005, vol. 65, 11729-11734.

(56) References Cited

OTHER PUBLICATIONS

Dilda et al., "Mechanism of selectivity of an angiogenesis inhibitor from screening a genome-wide set of *Saccharomyces cerevisiae* deletion strains," J. Natl. Cancer Institute, 2005, vol. 97, 1539-1547.
Evens et al., "The potential of arsenic trioxide in the treatment of malignant disease: past, present, and future," Leuk. Res., 2004, vol. 28, 891-900.
Evers et al., Inhibitory effect of the reversal agents V-104, GF120918 and Pluronic L61 on MDR1 Pgp-, MRP1- and MRP2-mediated transport, Br. J. Cancer, 2000, vol. 83, 366-374.
Kobayashi et al., "Involvement of human organic anion transporting polypeptide OATP-B (SLC21A9) in pH-dependent transport across intestinal apical membrane," J. Pharmacol. Exp. Ther, 2003, vol. 306, 703-708.
Kool et al., "MRP3, an organic anion transporter able to transport anti-cancer drugs," Proc. Natl. Acad. Sci., 1999, vol. 96, 6914-6919.
Beilstein Registry No. 21688; Jun. 27, 1988.
Beilstein Registry No. 22377; Jun. 27, 1988.
Beilstein Registry No. 51552; Jun. 27, 1988.
Beilstein Registry No. 111664; Jun. 27, 1988.
Beilstein Registry No. 116874; Jun. 27, 1988.
Beilstein Registry No. 273946; Jun. 27, 1988.
Beilstein Registry No. 358898; Jun. 27, 1988.
Beilstein Registry No. 3126376; Jun. 27, 1988.
Beilstein Registry No. 3129248; Feb. 15, 1990.
Beilstein Registry No. 3139905; Feb. 15, 1990.
Beilstein Registry No. 3141604; Feb. 15, 1990.
Beilstein Registry No. 3152231; Feb. 15, 1990.
Beilstein Registry No. 3233826; Feb. 15, 1990.
Beilstein Registry No. 3235693; Feb. 15, 1990.
Beilstein Registry No. 3254079; Feb. 15, 1990.
Beilstein Registry No. 3273842; Feb. 15, 1990.
Beilstein Registry No. 3275319; Feb. 15, 1990.
Beilstein Registry No. 3285106; Feb. 15, 1990.
Beilstein Registry No. 3293148; Feb. 15, 1990.
Beilstein Registry No. 3296676; Feb. 15, 1990.
Beilstein Registry No. 3298747; Feb. 15, 1990.
Beilstein Registry No. 3319010; Feb. 15, 1990.
Beilstein Registry No. 3341328; Feb. 15, 1990.
Beilstein Registry No. 3344707; Feb. 15, 1990.
Beilstein Registry No. 3531489; Feb. 15, 1990.

\* cited by examiner

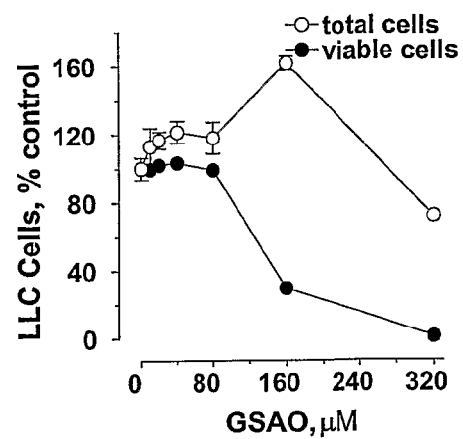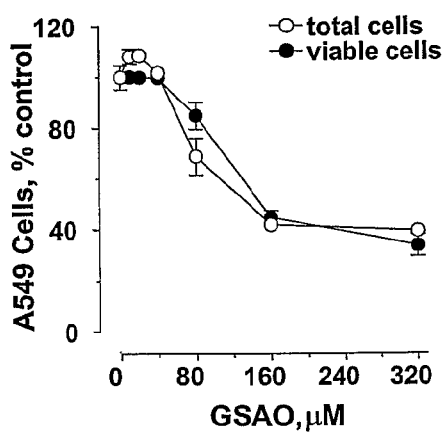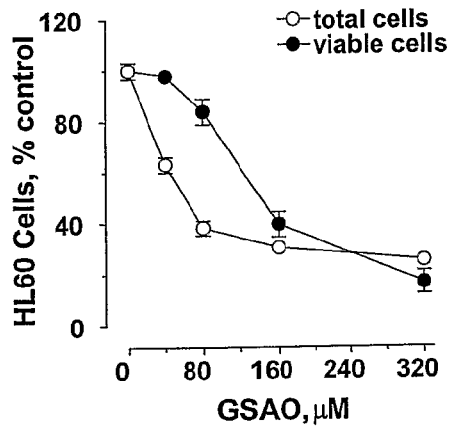
FIGURES 5E, 5F, and 5G

A

INDUCTION OF THE MITOCHONDRIAL PERMEABILITY TRANSITION

This application is a continuation of U.S. application Ser. No. 10/534,922 filed Jan. 30, 2006, which was the National Stage of International Application No. PCT/AU03/001483 filed Nov. 7, 2003, which claims priority to Australian Application No. 2002952526 filed Nov. 7, 2002 and Australian Application No. 2003906109 filed Nov. 5, 2003. The contents of the Ser. No. 10/534,922 application are hereby incorporated by reference in its entirety.

TECHNICAL FIELD

The present invention relates to modification of mitochondrial membrane permeability in cells and in particular, the identification and use of compounds which selectively induce the MPT in proliferating cells.

BACKGROUND OF THE INVENTION

Mitochondria provide ATP to support normal cell function and their perturbation leads to apoptotic and necrotic cell death (Crompton, 1999). An important factor in apoptosis and necrosis is the mitochondrial permeability transition (MPT), which occurs as a result of calcium overload. The cause of the MPT is the opening of a non-specific pore in the inner mitochondrial membrane, known as the mitochondrial permeability transition pore (MPTP) (Crompton et al., 1987). Oxidative stress, adenine nucleotide depletion and elevated inorganic phosphate greatly increase the sensitivity of the pore to calcium concentration. Opening of the MPTP is accompanied by equilibration of all small solutes (<1.5 kD) across the inner mitochondrial membrane. The resultant high protein concentration in the matrix exerts a colloidal osmotic pressure that is responsible for extensive swelling of mitochondria, and ultimately, apoptosis or necrosis.

Adenine nucleotide translocator (ANT) is a 30 kD protein that spans the inner mitochondrial membrane and is central to the MPTP (Crompton et al., 1988).

There is a need to selectively induce the MPT, particularly in proliferating cells, as a means of inducing apoptosis.

The present invention relates to a process for identifying compounds which bind to ANT in mitochondria and selectively induce the MPT in proliferating cells relative to non-proliferating or growth quiescent cells.

SUMMARY OF THE INVENTION

According to a first aspect of the invention there is provided a process for identifying a compound which induces the mitochondrial permeability transition (MPT) in proliferating cells, wherein the process comprises contacting a cell or cell extract with a compound, determining whether the compound binds to adenine nucleotide translocator (ANT), and determining whether the compound selectively induces the MPT in proliferating cells.

According to a second aspect of the invention there is provided a process for screening a plurality of compounds to identify a compound which induces MPT in proliferating cells, wherein the process comprises contacting a cell or a cell extract with the plurality of compounds, determining whether any of the compounds bind to ANT, and if so, separately determining for each of the plurality of compounds whether the compound selectively induces the MPT in proliferating cells.

With reference to the first and second aspects of the invention, selective induction of the MPT in proliferating cells may be determined, for example, by comparing the effect of compounds identified as binding to ANT in accordance with the first or second aspect of the invention, on the MPT in proliferating cells with the effect on the MPT in non-proliferating or growth quiescent cells.

Also with reference to the first and second aspects of the invention, in one embodiment the process may involve measuring changes in the cellular concentration of the superoxide ($O_2^-$) anion. In another embodiment, the process may involve measuring changes in Cytochrome C release.

According to a third aspect of the invention there is provided a process for identifying a compound which induces apoptosis in proliferating cells, the process comprising contacting a cell or cell extract with a candidate compound, determining whether there is an increase in cellular superoxide anion ($O_2^-$) concentration, and determining whether the compound selectively induces apoptosis in proliferating cells.

According to a fourth aspect of the invention there is provided a process for identifying a compound which is an inhibitor of angiogenesis, the process comprising contacting a cell or cell extract with a candidate compound, determining whether there is an increase in cellular superoxide anion ($O_2^-$) concentration, and determining whether the compound is an inhibitor of angiogenesis.

According to a fifth aspect of the invention there is provided a method of inducing MPT in a vertebrate, wherein the method comprises administering to the vertebrate a therapeutically effective amount of at least one compound detected in accordance with the process of any one of the first to third aspects of the invention, or a therapeutically effective amount of a pharmaceutical composition comprising at least one of the compounds together with a pharmaceutically acceptable carrier, adjuvant and/or diluent.

According to a sixth aspect of the invention there is provided a method of inducing apoptosis in proliferating mammalian cells, comprising administering to the mammal an apoptosis-inducing amount of a compound identified in accordance with the any one of the first to third aspects of the invention, or a therapeutically effective amount of a pharmaceutical composition comprising at least one of the compounds together with a pharmaceutically acceptable carrier, adjuvant and/or diluent.

According to a seventh aspect of the invention there is provided the use of a compound identified in accordance with any one of the first to third aspects of the invention for the manufacture of a medicament for inducing apoptosis.

According to an eighth aspect of the invention there is provided a method of inhibiting angiogenesis in a mammal, comprising administering to the mammal an angiogenesis-inhibiting amount of a compound identified in accordance with the fourth aspect of the invention, or a therapeutically effective amount of a pharmaceutical composition comprising at least one of the compounds together with a pharmaceutically acceptable carrier, adjuvant and/or diluent.

According to a ninth aspect of the invention there is provided the use of a compound identified in accordance with the fourth aspect of the invention for the manufacture of a medicament for inhibiting angiogenesis.

With reference to any one of the first to ninth aspects of the invention, in one embodiment the compound may be a dithiol reactive compound.

In another embodiment, the compound may have an arsenoxide (or arsenoxide equivalent) moiety.

In a further embodiment, the arsenoxide (or arsenoxide equivalent) compound may have the formula (I):

$$A-[(XBX')_n B'—Y]_p \quad (I)$$

wherein

A comprises at least one substantially cell-membrane impermeable pendant group;

$(XBX')_n B'$ comprises a suitable linker group, where n is an integer selected from 0, 1, 2, 3, 4, 5, 6, 7, 8, 9, 10, 11, 12, 13, 14, 15, 16, 17, 18, 19 and 20;

Y comprises at least one arsenoxide or arsenoxide equivalent; and p is an integer selected from 1, 2, 3, 4, 5, 6, 7, 8, 9, and 10.

In one embodiment, the compound of formula (I) may have more than 6 carbon atoms.

The following features relate to Formula (I):

In one embodiment, A may be selected from the group consisting of natural, unnatural and synthetic amino acids, hydrophilic amines, peptides and polypeptides, including dipeptides, tripeptides, tetrapeptides, pentapeptides, sugar residues such as monosaccharides, disaccharides, and oligosaccharides (including substituted variants), and thiol containing proteins, or a combination thereof. For example, A may be selected from the group consisting of glutathione, glucosamine, cysteinylglycine, cysteic acid, aspartic acid, glutamic acid, lysine, and arginine, wherein the sulfur atom of each sulfur containing compound may be optionally oxidised to form a sulfoxide or sulfone. In other embodiments, A may comprise a sugar residue, disaccharide or oligosaccharide residue such as, for example, glucose, fructose, mannose, xylose, lyxose, galactose, hexose, sucrose, sorbose, galactosyl-sucrose, sorbitol, mannitol, xylitol, etc. In other embodiments, A may be a hydrophilic amine such as a primary, secondary, or tertiary alkyl-, aryl- or aralkyl-amine, or a heterocyclic amine such as pyridine, pyrrole, imidazole etc.

Amino acids are known to those of skill in the art and are listed, for instance in standard reference texts, such as King and Stansfield, A Dictionary of Genetics, 4th Edition, Oxford University Press, 1990, the contents of which are incorporated herein by reference. For example, the amino acids may be α, β or γ amino acids. The present invention also includes the L- and D-forms of amino acids. Examples of amino acids include glycine, alanine, valine, leucine, isoleucine, methionine, proline, phenylalanine, tryptophan, serine, threonine, cysteine, tyrosine, asparagine, glutamine, aspartic acid, glutamic acid, lysine, arginine and histidine.

In one embodiment, A may be selected from the group consisting of tri-acid ureas, peptides including dipeptides, tripeptides, tetrapeptides, and pentapeptides. For example, glutathione, Cys-Glu-Gly, Arg-Gly-Asp-Cys, Val-Thr-Cys-Gly, Gly-Gly-Cys, Lys-Glu-Gly, Arg-Gly-Asp-Lys, Val-Thr-Lys-Gly, Gly-Gly-Lys, Ser-Glu-Gly, Arg-Gly-Asp-Ser, Val-Thr-Ser-Gly, Gly-Gly-Ser, Asp-Glu-Gly, Arg-Gly-Asp-Asp, Val-Thr-Asp-Gly, Gly-Gly-Asp, Glu-Glu-Gly, Arg-Gly-Asp-Glu, Val-Thr-Glu-Gly, Gly-Gly-Glu, etc, pressinoic acid, small acid molecules such as 3-mercapto-1-propanesulfonic acid, mercaptopropionic acid, mercapto succinic acid; small alcohols such as 1-thio-beta-D-glucose, 3-mercapto-1,2-propanediol; small amines, including for example, primary, secondary and tertiary alkyl-, aryl- and aralkyl substituted amines; and heteroaromatic compounds such as 5-mercapto-1-tetrazolacetic acid, 2-mercaptopyridine, and 2-aminopyridine.

In one embodiment, A is a tripeptide. For example, A may be glutathione and in one form the compound may be represented by Formula (II):

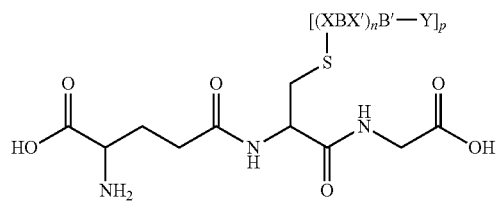

wherein $(XBX')_n B'$ comprises any suitable linker group, and Y comprises an arsenoxide or an arsenoxide equivalent.

In one embodiment, p is an integer selected from 1 to 5. For example, p may be 1, 2, 3, 4, or 5. In one embodiment p is 1 or 2. In another embodiment, p is 1.

In one embodiment, n is an integer from 0 to 15. For example, n may be 0, 1, 2, 3, 4, 5, 6, 7, 8, 9, 10, 11, 12, 13, 14, or 15. In one embodiment n is an integer selected from 0 to 10. In another embodiment n is an integer selected from 0 to 5, for example, n may be 0, 1, 2, 3, 4, or 5.

In one embodiment, X is selected from the group consisting of —NR, —S(O)—, —S(O)O—, —S(O)$_2$—, —S(O)$_2$O—, —C(O)—, —C(S)—, —C(O)O—, C(S)O—, —C(S)S—, —P(O)(R$_1$)—, and —P(O)(R$_1$)O—, or is absent;

B is selected from the group consisting of C$_1$-C$_{10}$ alkylene, C$_2$-C$_{10}$ alkenylene, C$_2$-C$_{10}$ alkynylene, C$_3$-C$_{10}$ cycloalkylene, C$_5$-C$_{10}$ cycloalkenylene, C$_3$-C$_{10}$ heterocycloalkylene, C$_5$-C$_{10}$ heterocycloalkenylene, C$_6$-C$_{12}$ arylene, heteroarylene and C$_2$-C$_{10}$ acyl;

X' is selected from the group consisting of —NR—, —O—, —S—, —Se—, —S—S—, S(O)—, —OS(O)—, OS(O)O—, —OS(O)$_2$, —OS(O)$_2$O—, —S(O)O—, —S(O)$_2$—, —S(O)$_2$O—, —OP(O)(R$_1$)—, —OP(O)(R$_1$)O—, —OP(O)(R$_1$)OP(O)(R$_1$)O—, —C(O)—, —C(S)—, —C(O)O—, C(S)O—, —C(S)S—, —P(O)(R$_1$)—, —P(O)(R$_1$)O—, and

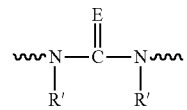

or is absent; wherein E is O, S, Se, NR or N(R)$_2$$^+$;

n is 0, 1 or 2; and

B' is selected from the group consisting of C$_1$-C$_{10}$ alkylene, C$_2$-C$_{10}$ alkenylene, C$_2$-C$_{10}$ alkynylene, C$_3$-C$_{10}$ cycloalkylene, C$_5$-C$_{10}$ cycloalkenylene, C$_3$-C$_{10}$ heterocycloalkylene, C$_5$-C$_{10}$ heterocycloalkenylene, C$_6$-C$_{12}$ arylene, and heteroarylene or is absent; and wherein each R is independently selected from the group consisting of hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_5$-C$_{10}$ cycloalkenyl, C$_3$-C$_{10}$ heterocycloalkyl, C$_5$-C$_{10}$ heterocycloalkenyl, C$_6$-C$_{12}$ aryl, heteroaryl, OR$_2$ and C$_2$-C$_{10}$ acyl;

R' is the same as R or two R' may be taken together with the nitrogen atoms to which they are attached to form a 5 or 6-membered saturated or unsaturated heterocyclic ring;

each R$_1$ is independently selected from the group consisting of hydrogen, C$_1$-C$_{10}$ alkyl, C$_2$-C$_{10}$ alkenyl, C$_2$-C$_{10}$ alkynyl, C$_3$-C$_{10}$ cycloalkyl, cycloalkenyl, C$_3$-C$_{10}$ heterocycloalkyl, C$_5$-C$_{10}$ heterocycloalkenyl, C$_6$-C$_{12}$ aryl, heteroaryl, halo, OR$_2$ and N(R)$_2$;

each R$_2$ is independently selected from the group consisting of hydrogen, C$_1$-C$_{10}$ alkyl, C$_2$-C$_{10}$ alkenyl, C$_2$-C$_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl and —C(O)$R_5$;

each $R_5$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy, $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio, OH, SH and N(R)$_2$;

wherein for each instance that B and/or B' is arylene, the substituents directly attached to the respective arylene rings (including arsenoxide or arsenoxide equivalent) may be at any available position, and for example, may be in a para-, meta- or ortho-relationship; and wherein each alkylene, alkenylene, alkynylene, cycloalkylene, cycloalkenylene, heterocycloalkylene, heterocycloalkenylene, arylene, heteroarylene and acyl may be independently substituted with hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, cyano, cyanate, isocyanate, OR$_{2a}$, SR$_6$, nitro, arsenoxide, —S(O)$R_3$, —OS(O)$R_3$, —S(O)$_2R_3$, —OS(O)$_2R_3$, —P(O)$R_4R_4$, —OP(O)$R_4R_4$, —N(R")$_2$, —NRC(O)(CH$_2$)$_m$Q, —C(O)$R_5$;

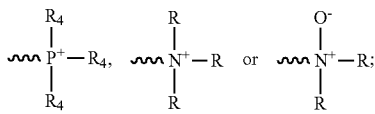

wherein R, $R_1$ and $R_5$ are as defined above; and $R_{2a}$ is selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, —S(O)$R_3$, —S(O)$_2R_3$, —P(O)(R$_4$)$_2$, N(R)$_2$ and —C(O)$R_5$;

each $R_3$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy, $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio and N(R)$_2$;

each $R_4$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy, $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio, halo and N(R)$_2$;

$R_6$ is selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio, —S(O)$R_3$, —S(O)$_2R_3$ and —C(O)$R_5$, R" is the same as R or two R" taken together with the N atom to which they are attached may form a saturated, unsaturated or aromatic heterocyclic ring system;

Q is selected from halogen and —OS(O)$_2Q_1$; wherein $Q_1$ is selected from $C_1$-$C_4$ alkyl, $C_1$-$C_4$ perfluoroalkyl, phenyl, p-methylphenyl; and m is 1, 2, 3, 4, or 5.

In another embodiment, X is selected from the group consisting of NH, —C(O)—, —C(S)—, —C(O)O—, C(S)O—, and —C(S)S—, or is absent;

B is selected from the group consisting of $C_1$-$C_5$ alkylene, $C_2$-$C_5$ alkenylene, $C_2$-$C_5$ alkynylene, $C_3$-$C_{10}$ cycloalkylene, $C_5$-$C_{10}$ cycloalkenylene, $C_6$-$C_{12}$ arylene and $C_2$-$C_5$ acyl;

X' is selected from the group consisting of —O—, —S—, —NR—, —S—S—, —S(O)—, —S(O)$_2$—, —P(O)(R$_1$)—, —OP(O)(R$_1$)—, OP(O)(R$_1$)O—, —OP(O)(R$_1$)OP(O)(R$_1$)O—, —C(O)—, —C(S)—, —C(O)O—, C(S)O—, —C(S)S—, —Se—,

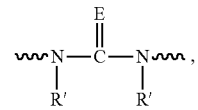

or is absent; wherein E is O, S or N(R)$_2^+$;

n is 0, 1 or 2; and

B' is $C_1$-$C_5$ selected from the group consisting of alkylene, $C_2$-$C_5$ alkenylene, $C_2$-$C_5$ alkynylene, $C_3$-$C_{10}$ cycloalkylene, $C_5$-$C_{10}$ cycloalkenylene, and $C_6$-$C_{12}$ arylene, or is absent; and wherein each R is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, OR$_2$ and $C_2$-$C_{10}$ acyl;

R' is the same as R;

each $R_1$ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, halo, OR$_2$ and N(R)$_2$;

each $R_2$ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, and —C(O)$R_5$;

each $R_5$ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $C_1$-$C_5$ alkoxy, $C_3$-$C_5$ alkenyloxy, $C_3$-$C_5$ alkynyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_5$ alkynylthio, $C_3$-$C_{10}$ cycloalkylthio, $C_5$-$C_{10}$ cycloalkenylthio, $C_6$-$C_{12}$ arylthio, OH, SH, and N(R)$_2$;

wherein for each instance that B and/or B' is arylene, the substituents directly attached to the respective arylene rings (including arsenoxide or arsenoxide equivalent), may be at any available position, and for example, may be in a para-, meta- or ortho-relationship, and wherein each alkylene, alkenylene, alkynylene, cycloalkylene, cycloalkenylene, arylene, and acyl may be independently substituted with hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, cyano, halo, cyanate, isocyanate, $OR_{2a}$, $SR_6$, nitro, arsenoxide, —S(O)$R_3$, —OS(O)$R_3$, —S(O)$_2R_3$, —OS(O)$_2R_3$, —P(O)$R_4R_4$, —OP(O)$R_4R_4$, —N(R″)$_2$, NRC(O)(CH$_2$)$_m$Q, —C(O)$R_5$,

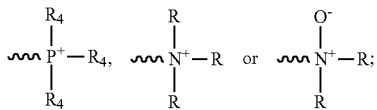

wherein R, $R_1$ and $R_5$ are as defined above; and $R_{2a}$ is selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, —S(O)$R_3$, —S(O)$_2R_3$, —P(O)($R_4$)$_2$, N(R)$_2$ and —C(O)$R_5$;

each $R_3$ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $C_1$-$C_5$ alkoxy, $C_3$-$C_5$ alkenyloxy, $C_3$-$C_5$ alkynyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_5$ alkynylthio, $C_3$-$C_{10}$ cycloalkylthio, $C_5$-$C_{10}$ cycloalkenylthio, $C_6$-$C_{12}$ arylthio and N(R)$_2$;

each $R_4$ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $C_1$-$C_5$ alkoxy, $C_3$-$C_5$ alkenyloxy, $C_3$-$C_5$ alkynyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_5$ alkynylthio, $C_3$-$C_5$ cycloalkylthio, $C_5$-$C_5$ cycloalkenylthio, $C_6$-$C_{12}$ arylthio, halo and N(R)$_2$;

$R_6$ is independently selected from the group consisting of $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $C_1$-$C_5$ alkylthio, $C_3$-$C_5$ alkenylthio, $C_3$-$C_5$ alkynylthio, $C_3$-$C_{10}$ cycloalkylthio, $C_5$-$C_{10}$ cycloalkenylthio, $C_6$-$C_{12}$ arylthio, —S(O)$R_3$, —S(O)$_2R_3$ and —C(O)$R_5$, R″ is the same as R;

Q is selected from the group consisting of halogen and —OS(O)$_2Q_1$; wherein $Q_1$ is selected from $C_1$-$C_4$ alkyl, $C_1$-$C_4$ perfluoroalkyl, phenyl, p-methylphenyl; and m is 1, 2, 3, 4 or 5.

In another embodiment, X is absent;

B is selected from the group consisting of $C_1$-$C_5$ alkylene, $C_6$-$C_{12}$ arylene and $C_2$-$C_5$ acyl;

X' is selected from the group consisting of —O—, —S—, —NR—, —S—S—, —S(O)—, —S(O)$_2$—, —P(O)($R_1$)—, —C(O)—, —C(S)—, —C(O)O—, C(S)O—, —Se—, and

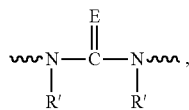

or absent; wherein E is O, S or N(R)$_2^+$;

n is 0, 1 or 2; and

B' is $C_1$-$C_5$ alkylene, $C_6$-$C_{12}$ arylene or is absent; and wherein each R is independently selected from the group consisting of hydrogen, $C_1$-$C_5$ alkyl, $C_3$-$C_{10}$ cycloalkyl, $C_6$-$C_{12}$ aryl, $OR_2$ and $C_2$-$C_5$ acyl;

R' is the same as R;

each $R_1$ is independently selected from the group consisting of hydrogen, $C_1$-$C_5$ alkyl, $C_3$-$C_{10}$ cycloalkyl, $C_6$-$C_{12}$ aryl, halo, $OR_2$ and N(R)$_2$;

each $R_2$ is independently selected from the group consisting of hydrogen, $C_1$-$C_5$ alkyl, $C_3$-$C_{10}$ cycloalkyl, $C_6$-$C_{12}$ aryl and —C(O)$R_5$;

each $R_5$ is independently selected from the group consisting of hydrogen, $C_1$-$C_5$ alkyl, $C_2$-$C_5$ alkenyl, $C_3$-$C_{10}$ cycloalkyl, $C_5$-$C_{10}$ cycloalkenyl, $C_6$-$C_{12}$ aryl, $C_1$-$C_5$ alkoxy, $C_3$-$C_5$ alkenyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_{10}$ cycloalkylthio, $C_5$-$C_{10}$ cycloalkenylthio, $C_6$-$C_{12}$ arylthio, OH, SH and N(R)$_2$;

wherein for each instance that B and/or B' is arylene, the substituents directly attached to the respective arylene rings (including arsenoxide or arsenoxide equivalent) may be at any available position on the respective ring(s) and, for example, may be in a para-, meta- or ortho-relationship, and wherein each alkylene, alkenylene, alkynylene, cycloalkylene, cycloalkenylene, arylene, and acyl may be independently substituted with hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, halo, cyano, cyanate, isocyanate, $OR_{2a}$, $SR_6$, nitro, arsenoxide, —S(O)$R_3$, —OS(O)$R_3$, —S(O)$_2R_3$, —OS(O)$_2R_3$, —P(O)$R_4R_4$, —OP(O)$R_4R_4$, —N(R″)$_2$, —NRC(O)(CH$_2$)$_m$Q, —C(O)$R_5$,

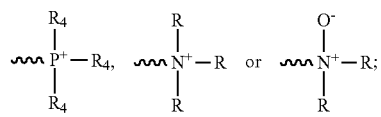

wherein R, $R_1$ and $R_5$ are as defined above; and $R_{2a}$ is selected from the group consisting of hydrogen, $C_1$-$C_6$ alkyl, $C_3$-$C_{10}$ cycloalkyl, $C_6$-$C_{12}$ aryl, —S(O)$R_3$, —S(O)$_2R_3$, —P(O)($R_4$)$_2$ and —C(O)$R_5$;

each $R_3$ is independently selected from the group consisting of hydrogen, $C_1$-$C_5$ alkyl, $C_3$-$C_{10}$ cycloalkyl, $C_6$-$C_{12}$ aryl, $C_1$-$C_5$ alkoxy, $C_3$-$C_{10}$ cycloalkyloxy, $C_6$-$C_{12}$ aryloxy, $C_1$-$C_5$ alkylthio, $C_3$-$C_{10}$ cycloalkylthio, $C_6$-$C_{12}$ arylthio and N(R)$_2$;

each $R_4$ is independently selected from the group consisting of hydrogen, $C_1$-$C_5$ alkyl, $C_3$-$C_{10}$ cycloalkyl, $C_6$-$C_{12}$ aryl, $C_1$-$C_5$ alkoxy, $C_3$-$C_{10}$ cycloalkyloxy, $C_6$-$C_{12}$ aryloxy, halo and N(R)$_2$;

$R_6$ is selected from the group consisting of $C_1$-$C_5$ alkyl, $C_3$-$C_{10}$ cycloalkyl, $C_6$-$C_{12}$ aryl, $C_1$-$C_5$ alkylthio, $C_3$-$C_{10}$ cycloalkylthio, $C_6$-$C_{12}$ arylthio, —S(O)$R_3$, —S(O)$_2R_3$ and —C(O)$R_5$, R″ is the same as R;

Q is selected from halogen and —OS(O)$_2Q_1$; wherein $Q_1$ is selected from $C_1$-$C_4$ alkyl, $C_1$-$C_4$ perfluoroalkyl, phenyl, p-methylphenyl; and m is 1, 2, 3, 4, or 5, In a further embodiment, X is absent;

B is selected from the group consisting of $C_1$-$C_5$ alkylene, $C_6$-$C_{12}$ arylene and $C_2$-$C_5$ acyl;

X' is selected from the group consisting of —O—, —S—, —NR—, —C(O)—, and —C(O)O—, or is absent;

n is 1; and

B' is $C_1$-$C_5$ alkylene, $C_6$-$C_{12}$ arylene or is absent; and

R is selected from the group consisting of hydrogen, $C_1$-$C_5$ alkyl, $C_6$-$C_{12}$ aryl and $C_2$-$C_5$ acyl;

wherein for each instance that B and/or B' is arylene, the substituents directly attached to the respective arylene rings (including arsenoxide or arsenoxide equivalent), may be at any available position on the respective ring(s) and, for example, may be in a para-, meta- or ortho-relationship, and wherein each alkylene, arylene, and acyl may be independently substituted with hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, halo, cyano, cyanate, isocyanate, $OR_{2a}$, $SR_6$, nitro, arsenoxide, —S(O)$R_3$, —S(O)$_2R_3$, —P(O)$R_4R_4$, —N(R'')$_2$, —NRC(O)(CH$_2$)$_m$Q, —C(O)$R_5$,

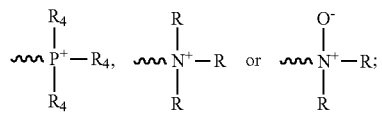

wherein each R is independently selected from the group consisting of hydrogen, $C_1$-$C_5$ alkyl, $C_6$-$C_{12}$ aryl and $C_2$-$C_5$ acyl;

$R_{2a}$ is selected from the group consisting of hydrogen, $C_1$-$C_5$ alkyl, $C_6$-$C_{12}$ aryl, —S(O)$R_3$, —S(O)$_2R_3$, —P(O)(R$_4$)$_2$ and —C(O)$R_5$;

each $R_3$ is independently selected from the group consisting of hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, and $C_6$-$C_{12}$ arylthio;

each $R_4$ is independently selected from the group consisting of hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, $C_6$-$C_{12}$ arylthio, halo and N(R)$_2$;

each $R_5$ is independently selected from the group consisting of hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, $C_6$-$C_{12}$ arylthio, OH, SH and N(R)$_2$;

$R_6$ is selected from the group consisting of $C_1$-$C_5$ alkyl, $C_6$-$C_{12}$ aryl, $C_1$-$C_5$ alkylthio, $C_6$-$C_{12}$ arylthio, —S(O)$R_3$, —S(O)$_2R_3$ and —C(O)$R_5$, R'' is the same as R above;

Q is selected from halogen and —OS(O)$_2Q_1$; wherein $Q_1$ is selected from $C_1$-$C_4$ alkyl, $C_1$-$C_4$ perfluoroalkyl, phenyl, p-methylphenyl; and m is 1, 2, 3, 4, or 5.

In yet another embodiment, X is absent;
B is $C_2$-$C_5$ acyl;
X' is NR;
n is 1;
B' is phenylene; and
R is H;

wherein the substituents directly attached to the phenylene ring may be at any available position, as illustrated, for example, by Formula (III):

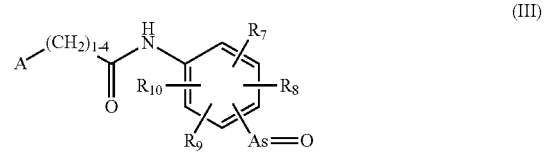

wherein $R_7$ to $R_{10}$ are independently selected from the group consisting of hydrogen, $C_1$-$C_5$ alkyl, $C_6$-$C_{12}$ aryl, halogen, hydroxy, amino, nitro, carboxy, $C_1$-$C_5$ alkoxy, —OS(O)$_2R_3$ and —NHC(O)CH$_2$Q wherein Q is halogen, —OS(O)$_2$CH$_3$, —OS(O)$_2C_6H_5$ and —OS(O)$_2$-p tolyl; and wherein, when any one of $R_7$ to $R_{10}$ is $C_1$-$C_5$ alkyl, $C_6$-$C_{12}$ aryl, $C_1$-$C_5$ alkoxy, —OS(O)$_2R_3$ it is capable of forming a fused ring with the phenylene; and further wherein, at least one of $R_7$ to $R_{10}$ is $C_1$-$C_5$ alkyl, $C_6$-$C_{12}$ aryl, $C_1$-$C_5$ alkoxy, or —OS(O)$_2R_3$, in combination with at least any one other of $R_7$ to $R_{10}$, is capable of forming a fused ring with the phenylene.

More typically, $R_7$ to $R_{10}$ are independently selected from the group consisting of hydrogen, halogen, hydroxy, amino, nitro, cyano, carboxy, $C_1$-$C_5$ alkoxy, methyl, ethyl, isopropyl, tert-butyl, phenyl and —NHC(O)CH$_2$Q wherein Q is halogen, —OS(O)$_2$CH$_3$, —OS(O)$_2C_6H_5$ and —OS(O)$_2$-p tolyl.

For example, when the pendant group A is glutathione, the compound of formula (III) may be represented as

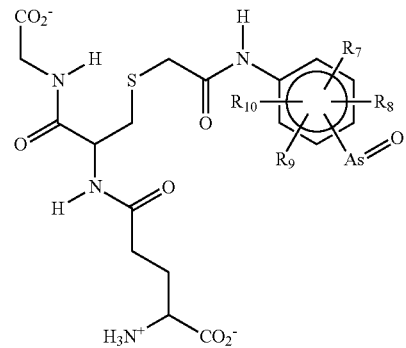

Further, when B' is arylene, the substituents attached to the arylene ring may be at any available position on the arylene ring. For example, the substituents may be in a meta- or para-relationship relative to the —As=O group.

In another embodiment, an arsenoxide compound identified in accordance with the present invention is selected from the following compounds:

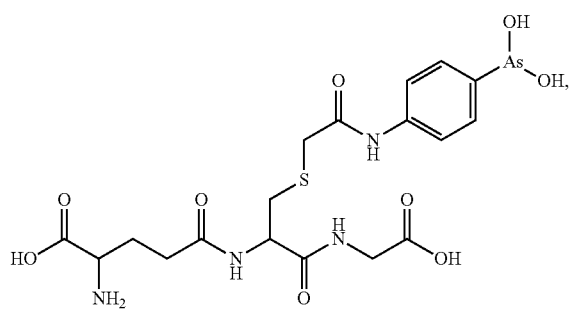

"GSAO"

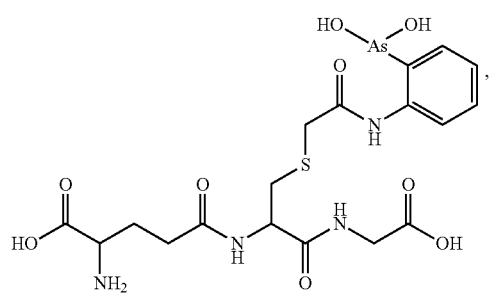

("o-GSAO")

-continued
2
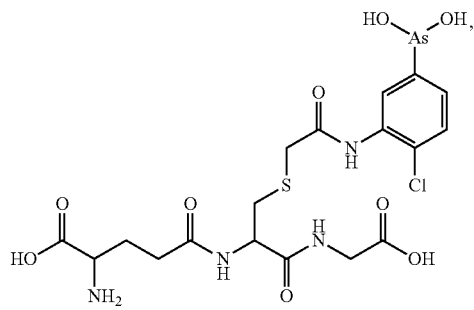
3
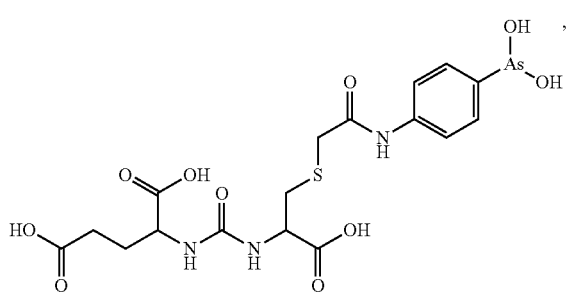
4
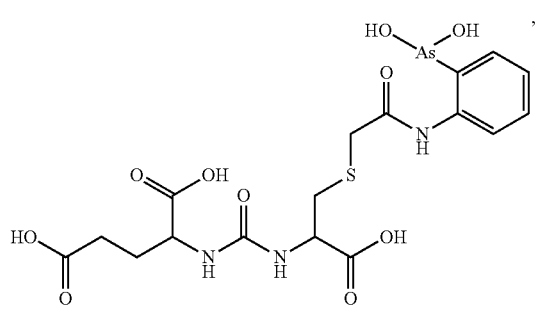
5
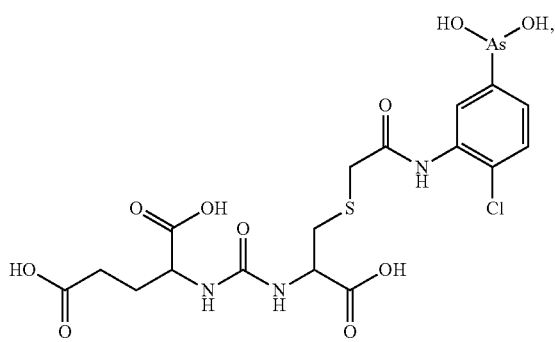
6
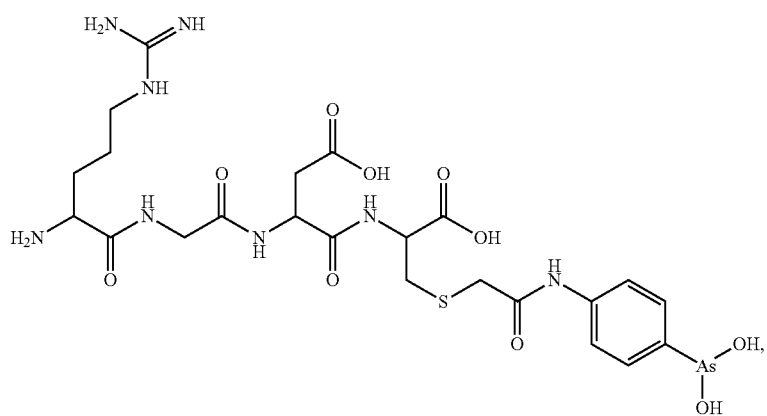
7
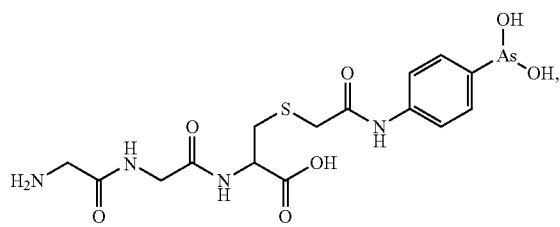
8
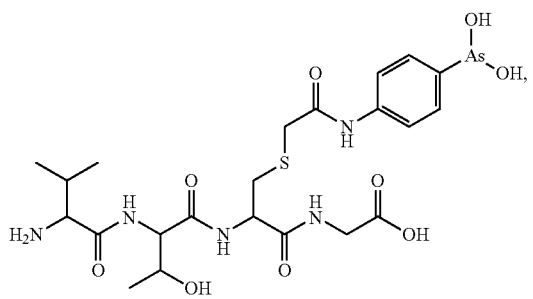

-continued
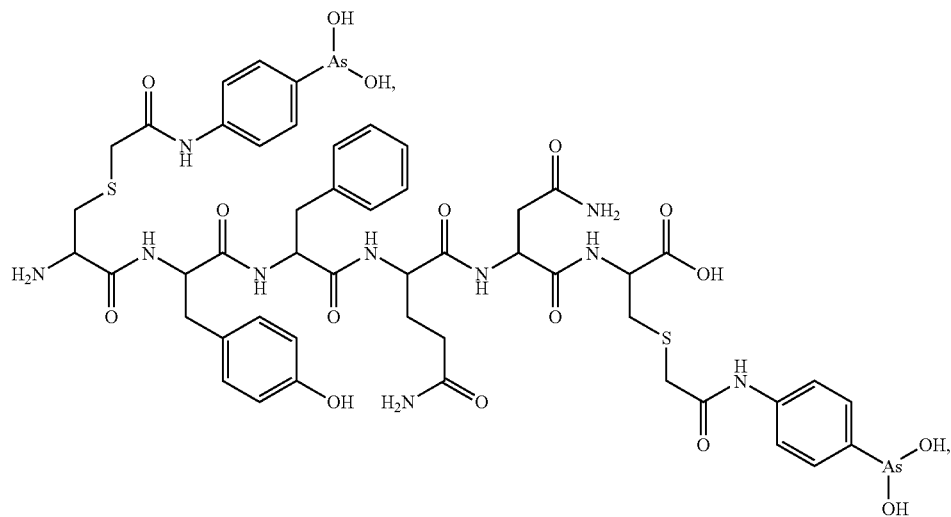
9
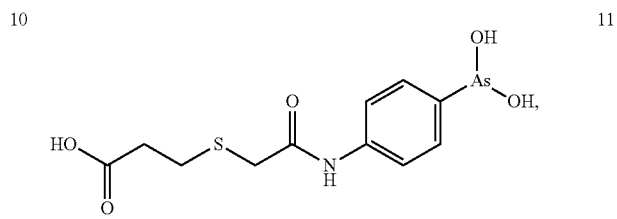
10
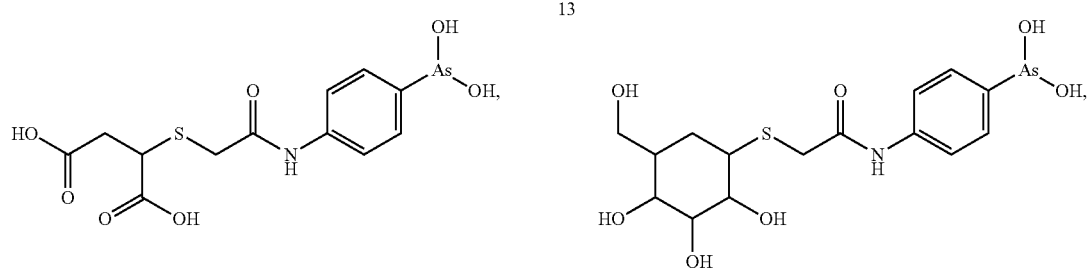
11 13 14
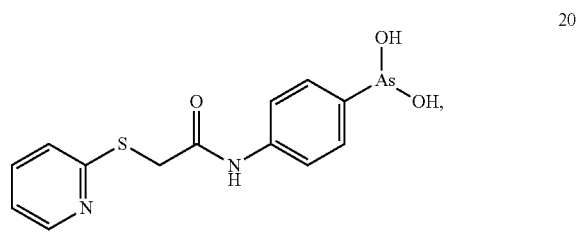
15 20
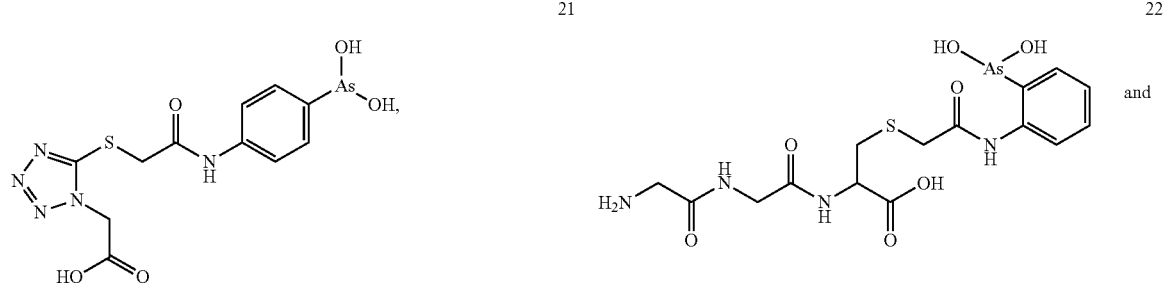
21 22 and -continued

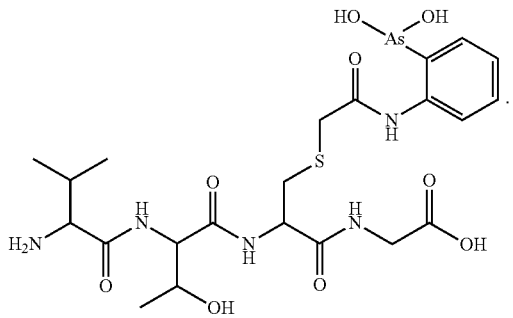

23

The compound "GSAO" (4-(N—(S-glutathionylacetyl)amino)-phenylarsenoxide) has been previously described in International patent application WO 01/21628, the entire contents of which are incorporated herein by cross-reference.

Other compounds which may interact with ANT include compounds according to Formula (V) illustrated below:

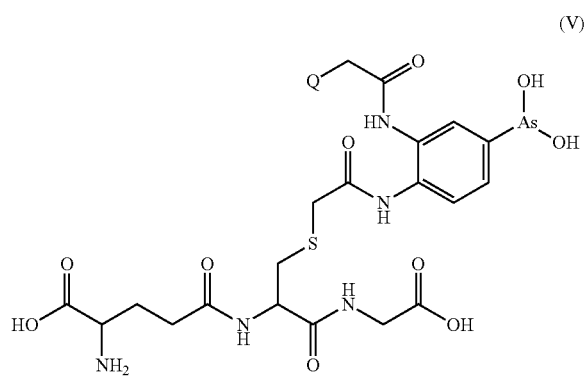

(V)

wherein Q is any halogen.

Another form of an arsenoxide compound which may interact with ANT is a compound according to Formula (VI):

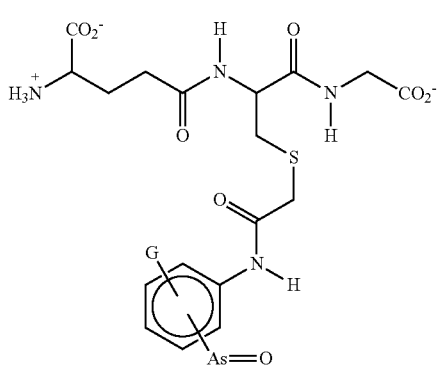

(VI)

wherein G is selected from the group consisting of hydrogen, halogen, hydroxy, amino, nitro, cyano, carboxy, $C_1$-$C_5$ alkoxy, $C_1$-$C_5$ alkyl and $C_6$-$C_{12}$ aryl and —NHC(O)CH$_2$Q, wherein Q is halogen, —OS(O)$_2$CH$_3$, —OS(O)$_2$C$_5$H$_5$ or —OS(O)$_2$-p tolyl.

Typically, G is selected from the group consisting of hydrogen, halogen, hydroxy, amino, nitro, carboxy, $C_1$-$C_5$ alkoxy, methyl, ethyl, isopropyl, tert-butyl, phenyl, and —NHC(O)CH$_2$Q, wherein Q is the group consisting of halogen, —OS(O)$_2$CH$_3$, —OS(O)$_2$C$_6$H$_5$ and —OS(O)$_2$-p tolyl.

In one embodiment, in a compound of Formula VI, G is hydroxy, fluorine, amino, or nitro.

In another embodiment, group G is in an ortho-, meta-, or para-relationship to the arsenoxide group. For example, in another embodiment G is in an ortho- or para-relationship to the arsenoxide group.

Typically the activity of the arsenic atom may be modified by the group G, when G and the arsenic atom are in an ortho or para relationship to one another. For example, when G is an electron donating group such as OH (ionised to O— at physiological pH), the arsenic atom may be deactivated towards dithiols and may become more selective, for example, only reacting with very reactive dithiols. Alternatively, when G is an electron withdrawing group, such as NO$_2$, electron density may be drawn away from the arsenic atom, making it more reactive to dithiols. Selective inhibition of some redox proteins and not others may be achieved by manipulation of G.

Typically, in the arsenoxide compounds capable of interacting with ANT, the arsenoxide group (—As═O) may be replaced by an arsenoxide equivalent.

An arsenoxide equivalent is defined herein as any dithiol reactive species that shows essentially the same affinity towards dithiols as —As═O. Typically, arsenoxide equivalent includes dithiol reactive entities, such as As, Ge, Sn and Sb species. More typically an arsenoxide equivalent can be represented by -D($Z_1$)($Z_2$). Arsenoxide equivalents are expected to exhibit identical or substantially identical activity to that of the corresponding arsenoxide.

Typically, for arsenoxide equivalents of the form -D($Z_1$)($Z_2$), D will be, for example, As, RSn, Sb, or RGe, and $Z_1$ and $Z_2$ will be labile groups (i.e. groups easily displaced under physiological conditions). $Z_1$ and $Z_2$, may be identical or different, and may either be connected or independent from each other (bound only to the arsenic atom).

Suitable arsenoxide equivalents include the following:

-D($Z_1$)($Z_2$), wherein $Z_1$ and $Z_2$ are selected from the group consisting of OH, $C_1$-$C_{10}$ alkoxy, $C_6$-$C_{10}$ aryloxy, $C_1$-$C_{10}$ alkylthio, $C_6$-$C_{10}$ arylthio, $C_1$-$C_{10}$ alkylseleno, $C_6$-$C_{10}$ arylseleno, F, Cl, Br and I;

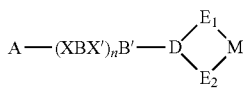

wherein $E_1$=$E_2$=O, $E_1$=O and $E_2$=S or $E_1$=$E_2$=S; M is R''' and R'''' are independently selected from the group consisting of hydrogen, $C_1$-$C_{10}$ alkyl, $C_6$-$C_{12}$ aryl, halogen, $C_1$-$C_{10}$ alkoxy, $C_6$-$C_{10}$ aryloxy, hydroxy and carboxy; and n=1 to 10.

For arsenoxide equivalents of the form $D(Z_1)(Z_2)$, when D is As and $Z_1$ and $Z_2$ are OH, the arsenoxide equivalent may be in equilibrium with polymeric species, as depicted below.

wherein $X_3=Y_1=O$, or $X_3=NH$, $Y_1=O$; and $R_{11}$ to $R_{14}$ are selected from the group consisting of hydrogen, $C_1$-$C_{10}$ alkyl, $C_6$-$C_{12}$ aryl, halogen, $C_1$-$C_{10}$ alkoxy, and $CO_2H$.

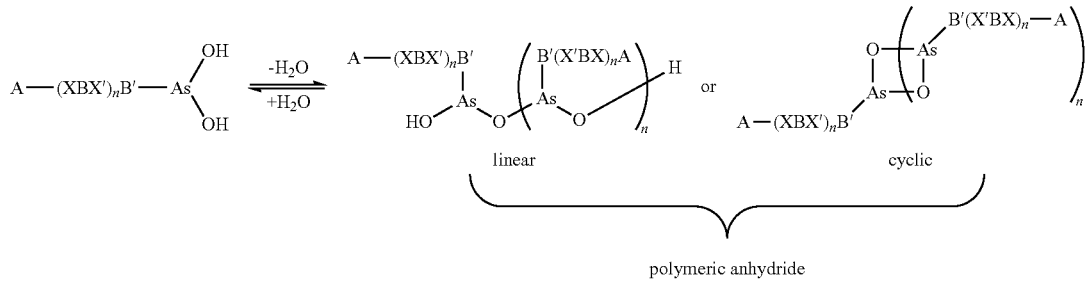

polymeric anhydride

In respect of the equilibrium depicted above, arsenic is one of many elements whose hydroxy species exist in equilibrium with the corresponding polymeric anhydrides (Doak & Freedman, 1970). Therefore, arsenoxide compounds may actually exist as low or medium molecular weight polymers (eg n=3 to 6). However, the dehydration reaction is reversible, and therefore soluble polymeric anhydrides are expected to behave as arsenoxide equivalents, that is, they are expected to bind to closely spaced dithiols in substantially the same way as the monomeric —As(OH)$_2$ species.

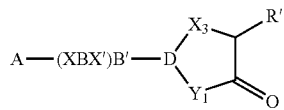

wherein $X_3=NH$, $Y_1=O$; $X_3=Y_1=O$ or $X_3=S$, $Y_1=O$, and R' is selected from the group consisting of hydrogen, $C_1$-$C_{10}$ alkyl, $C_6$-$C_{12}$ aryl, and carboxy, or is one of the twenty amino acid side chains;

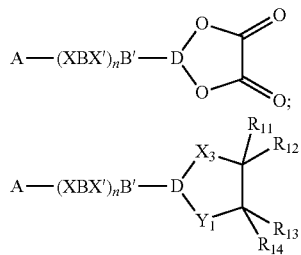

wherein $X_3=Y_1=O$; $X_3=NH$, $Y_1=O$; $X_3=S$, $Y_1=O$; $X_3=Y_1=NH$; or $X_3=S$, $Y_1=NH$; or $X_3=S$, $Y_1=NH$ and $R_{11}$ to $R_{14}$ are selected from the group consisting of hydrogen, $C_1$-$C_{10}$ alkyl, $C_6$-$C_{12}$ aryl, and $CO_2H$;

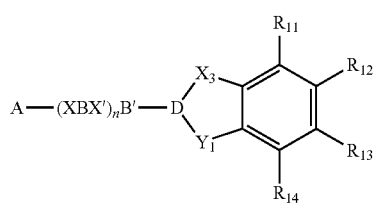

Typically, (XBX')B' is as defined above.

ABBREVIATIONS AND DEFINITIONS

In the context of this specification, the abbreviation MPT stands for Mitochondrial Permeability Transition.

In the context of this specification, the abbreviation MPTP stands for Mitochondrial Permeability Transition Pore.

In the context of this specification, the abbreviation ANT stands for adenine nucleotide translocator.

In the context of this specification EGTA is ethylene glycol-bis(beta-aminoethyl ether)-N,N,N'N'-tetraacetic acid.

In the context of this specification, PAO stands for phenyl arsenoxide.

In the context of this specification, the term "comprising" means "including principally, but not necessarily solely". Furthermore, variations of the word "comprising", such as "comprise" and "comprises", have correspondingly varied meanings.

In the context of this specification, the term "arsenoxide" refers to the group —As=O.

In the context of this specification, the groups written —As=O and —As(OH)$_2$ are to be considered synonymous.

In the context of this specification, the term "arsenoxide equivalent" refers to any dithiol reactive species that shows essentially the same affinity towards dithiols as —As=O or As(OH)$_2$, and the term includes, for example, groups comprising a transition element, and any trivalent arsenical that is either hydrolysed to —As=O or —As(OH)$_2$ when dissolved in an aqueous medium (such as cell culture buffers and the fluids contained in the organism being treated).

In the context of this specification the term "substantially cell membrane impermeable group" refers to any group which limits the rate at which a compound passes through a cell membrane and into the cell. A substantially cell membrane impermeable group may limit the rate of entry of a compound into a cell by virtue of one or more properties such as, for example, charge, size (molecular weight), polarity, lipophilicity, hydrophilicity, etc.

The term "arsenical" as used herein, includes any compound that contains arsenic.

The term "acyl" as used herein, includes monovalent and divalent alkyl, alkenyl, alkynyl, cycloalkyl and cycloalkenyl moieties possessing a terminal carbonyl substituent wherein attachment may occur at the hydrocarbon moiety, the carbonyl moiety or both.

The term "alkyl" as used herein, includes within its meaning monovalent, saturated, straight and branched chain hydrocarbon radicals.

The term "alkenyl" as used herein, includes within its meaning, monovalent, straight and branched chain hydrocarbon radicals having at least one double bond.

The term "alkynyl" as used herein, includes within its meaning, monovalent, straight and branched chain hydrocarbon radicals having at least one triple bond.

The term "alkylene" as used herein, includes within its meaning divalent, saturated, straight chain hydrocarbon radicals.

The term "alkenylene" as used herein, includes within its meaning, divalent, straight chain hydrocarbon radicals having at least one double bond.

The term "alkynylene" as used herein, includes within its meaning, divalent, straight chain hydrocarbon radicals having at least one triple bond.

The term "aryl" as used herein, includes within its meaning monovalent, single, polynuclear, conjugated and fused aromatic hydrocarbon radicals.

The term "arylene" as used herein, includes within its meaning divalent, single, polynuclear, conjugated and fused aromatic hydrocarbon radicals.

The term "closely spaced dithiol" as used herein, includes within its meaning thiols that are chemically vicinal, as well as thiols brought into spatial apposition by virtue of molecular conformation.

The term "cycloalkyl" as used herein, includes within its meaning monovalent, saturated, monocyclic, bicyclic, polycyclic or fused polycyclic hydrocarbon radicals.

The term "cycloalkylene" as used herein, includes within its meaning divalent, saturated, monocyclic, bicyclic, polycyclic or fused polycyclic hydrocarbon radicals.

The term "cycloalkenyl" as used herein, includes within its meaning monovalent, saturated, monocyclic, bicyclic, polycyclic or fused polycyclic hydrocarbon radicals having at least one double bond.

The term "cycloalkenylene" as used herein, includes within its meaning divalent, saturated, monocyclic, bicyclic, polycyclic or fused polycyclic hydrocarbon radicals having at least one double bond.

The term "halo" as used herein, includes fluoro, chloro, bromo and iodo.

The term "heteroaryl" as used herein, includes within its meaning monovalent, single, polynuclear, conjugated and fused aromatic radicals having 1 to 12 atoms wherein 1 to 6 atoms are heteroatoms selected from O, N and S.

The term "heteroarylene" as used herein, includes within its meaning divalent, single, polynuclear, conjugated and fused aromatic radicals having 1 to 12 atoms wherein 1 to 6 atoms are heteroatoms selected from O, N and S.

The term "heterocycloalkyl" as used herein, includes within its meaning monovalent, saturated, monocyclic, bicyclic, polycyclic or fused radicals wherein 1 to 5 atoms are heteroatoms selected from O, N or S.

The term "heterocycloalkylene" as used herein, includes within its meaning divalent, saturated, monocyclic, bicyclic, polycyclic or fused polycyclic radicals wherein 1 to 5 atoms are heteroatoms selected from O, N or S.

The term "heterocycloalkenyl" as used herein, includes within its meaning monovalent, saturated, monocyclic, bicyclic, polycyclic or fused polycyclic radicals having at least 1 double bond and wherein 1 to 5 atoms are heteroatoms selected from O, N or S.

The term "heterocycloalkenylene" as used herein, includes within its meaning divalent, saturated, monocyclic, bicyclic, polycyclic or fused polycyclic radicals having at least one double bond and wherein 1 to 5 atoms are heteroatoms selected from O, N or S.

The term "phenylarsonic acid" as used herein, is to be considered synonymous with "benzene arsonic acid".

DETAILED DESCRIPTION

Figure 1A:
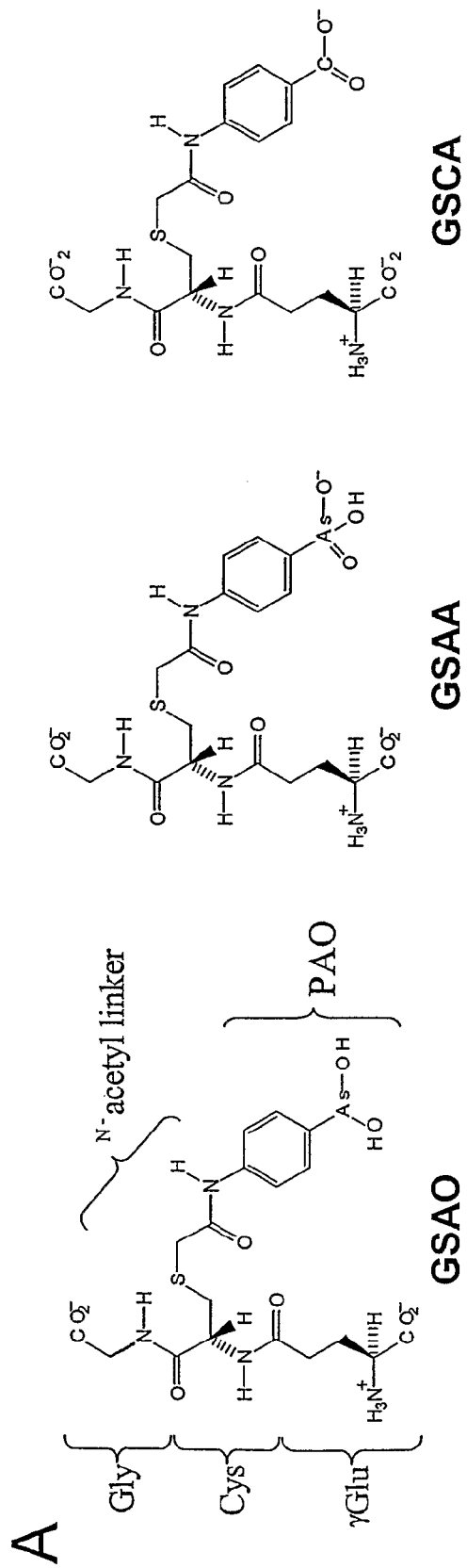
FIG. 1. GSAO triggered MTP opening by reacting with and perturbing ANT. A Structure of GSAO, GSAA, and GSCA. B GSAO triggered swelling of mitochondria. Swelling was measured by monitoring the associated decrease in light scattering at 520 nm over 60 min. The traces are representative of a minimum of three experiments on at least two different mitochondrial preparations. In part i, mitochondria were incubated with nil (●), 25 (○), 50 (▲), 100 (Δ) or 200 (■) μM GSAO. The positive control for pore opening was 150 μM $Ca^{2+}$ and 6 mM Pi (□). In part ii, mitochondria were incubated with nil (●), 100 μM GSCA (Δ), 100 μM GSAA (▲) or 100 μM GSAO (■). The positive control for pore opening was 25 μM PAO (○). In part iii, mitochondria were incubated with 100 μM GSAO in the absence (■) or presence of 3 mM $Mg^{2+}$ (▼), 100 μM EGTA (Δ), 10 μM BKA (▲), 5 μM CsA (∇), or 8 mM ADP (○). No treatment (●) is shown for comparison. C Increasing $Ca^{2+}$ concentration sensitises the MPTP to GSAO. Mitochondria were incubated with 50 (●), 75 (○), 100 (■) or 200 μM (□) GSAO in the absence or presence of increasing $Ca^{2+}$ concentration and the time for half-maximal swelling was measured. D Labelling of ANT with GSAO-B. Isolated rat mitochondria were labelled with GSAO-B in the absence (lane 1) or presence (lane 2) of a 4-fold molar excess of 2,3-dimercaptopropanol (DMP) and the biotin-labelled proteins were collected on streptavidin-agarose beads, resolved on SDS-PAGE and Western blotted for ANT. E GSAO competed for alkylation of $Cys^{160}$ in ANT by eosine-maleimide. Rat sub-mitochondrial particles were labelled with eosin-5-maleimide in the absence (lane 1) or presence (lane 2) of GSAO and the eosin-labelled ANT was resolved on SDS-PAGE and detected by transillumination.

The present invention relates to processes for identifying compounds which bind to ANT in mitochondria and selectively induce the MPT in proliferating cells, relative to non-proliferating cells.

ANT is a 30 kD protein that spans the inner mitochondrial membrane and is central to the MPTP (Crompton et al., 1988). There are three unpaired cysteines on the matrix side of ANT—$Cys^{57}$, $Cys^{160}$ and $Cys^{257}$. (Halestrap et al., 1997). ANT activity is controlled by the binding of $Ca^{2+}$, cyclophilin D and adenine nucleotides. Cyclophilin D (Crompton et al., 1988) and adenine nucleotides (Haworth & Hunter, 1979a,b;

Haworth & Hunter, 2000) bind to the matrix side of ANT, while the site(s) for interaction of $Ca^{2+}$ has yet to be determined. There are several known regulators of the MPTP that appear to act by modulating binding of these three compounds. The primary trigger for opening of the MPTP is a rise in matrix $Ca^{2+}$ concentration. Chelation of $Ca^{2+}$ with EGTA blocks pore opening. The specificity of the trigger site (presumably on ANT) for $Ca^{2+}$ appears to be absolute as other divalent metal ions such as $Mg^{2+}$ act as inhibitors (Haworth & Hunter, 1979a). Binding of cyclophilin D to ANT is necessary for pore opening at sub-millimolar $Ca^{2+}$ concentrations (Halestrap et al., 2002). Cyclosporin A (CsA) blocks pore opening by binding to cyclophilin D and displacing it from ANT (Crompton et al., 1988). Matrix ADP is also an important modulator of pore opening that binds to ANT and decreases the sensitivity of the trigger site to $Ca^{2+}$ (Haworth & Hunter, 1979a,b). Bonkrekic acid (BKA) also interacts with ANT and decreases sensitivity to $Ca^{2+}$ (Hunter & Haworth, 1979).

Generally, the process for identifying a compound which induces the MPT in proliferating cells in accordance with the invention comprises contacting a cell or cell extract with a candidate compound, determining whether the compound binds to ANT, and then determining whether the compound selectively induces the MPT in proliferating cells. Assessing whether a compound selectively induces the MPT in proliferating cells may be determined by comparing the effect of a compound identified as binding to ANT on the MPT in proliferating cells with the effect of the compound on the MPT in non-proliferating or growth quiescent cells.

Monitoring induction of MPT can be done using standard techniques known to those in the art. For example, spectrophotometrically monitoring the change in light scattering at a given wavelength, for differing concentrations of compound. A suitable wavelength is typically 520 nm.

Detecting the uptake of a compound into the mitochondria of a cell can be carried out using standard techniques. For example, fluorescent labelled compounds can be used or a fluorophore can be attached to a compound. Examples of suitable fluorophores include fluorescein and Cy™5.5. Subcellular localisation of compounds can be detected by standard techniques including confocal fluorescence microscopy. Alternatively, compounds can be attached to other detectable groups, eg biotin, and detected by staining with streptavidin, such as Streptavidin-Alexa Fluor 488.

Mitochondrial transmembrane potential can be assessed using standard techniques, including, for example, dyes, such as JC-1, and stains, such as annexin V-FITC. By such techniques it is possible to determine whether cells have undergone the MPT and assess whether apoptosis has been induced.

Reactive oxygen species, such as superoxide anion ($O_2^-$) and hydrogen peroxide ($H_2O_2$), are generated as a by-product of ATP production and play an important role as signalling intermediates in cellular proliferation, but at elevated concentrations they arrest proliferation and induce apoptosis by damaging lipids, proteins, DNA, and RNA (Zanetti et al., 2001). $O_2^-$ is converted in the mitochondria to $H_2O_2$ by Mn superoxide dismutase (SOD), but can also be released from mitochondria through anion channels, where it is dismuted to $H_2O_2$ by cytosolic Cu/Zn SOD (Vanden Hoek et al., 1998).

There is also disclosed herein a process for identifying a compound which may be capable of inducing apoptosis in proliferating cells, wherein the process comprises contacting a cell or cell extract with a candidate compound, determining whether there is an increase in cellular superoxide anion ($O_2^-$) concentration, and then determining whether the compound selectively induces apoptosis in proliferating cells relative to non-proliferating or growth quiescent cells. Assessing whether a compound selectively induces apoptosis in proliferating cells can be readily determined by those skilled in the art by comparing the effect of the compound on cellular superoxide anion levels in proliferating cells with the effect in non-proliferating or growth quiescent cells. Measurement of cellular superoxide levels can be carried out using assays well known to those skilled in the art.

Release of Cytochrome C from the inter-membrane space of mitochondria is also a known trigger of apoptosis in cells. Measuring changes in levels of Cytochrome C in proliferating cells (relative to non-proliferating cells), may be useful for identifying compounds which perturb mitochondrial function.

Also disclosed herein is a process for identifying a compound which may be an inhibitor of angiogenesis, wherein the process comprises contacting a cell or cell extract with a candidate compound, determining whether there is an increase in cellular superoxide anion ($O_2^-$) concentration, and thereby determining whether the compound may be an inhibitor of angiogenesis.

Angiogenesis refers to the sprouting of new capillaries from existing vessels and is driven by proliferating endothelial cells. Angiogenesis occurs during embryogenesis and in the adult (Carmeliet & Jain, 2001). In the normal adult mammal angiogenesis is confined to the female reproductive cycles, wound healing and several pathological situations. Angiogenesis is a key factor in diseases such as rheumatoid arthritis, psoriasis, diabetic retinopathy and cancer. Tumour expansion and metastasis is dependent on tumour angiogenesis (Hanahan & Folkman, 1996).

Therapeutic Applications

Perturbation of the MPT by compounds which bind to ANT may induce apoptosis. Reactive oxygen species such as superoxide anion ($O_2^-$) play an important role as signalling intermediates in cellular proliferation, however elevated concentrations can arrest proliferation and induce apoptosis. Accordingly, compounds which bind to ANT and selectively inhibit mitochondrial function, or compounds which increase cellular levels of superoxide anion in proliferating cells compared to non-proliferating cells, may have the potential to be therapeutically useful for treating various diseases and conditions in vertebrates.

Further, release of Cytochrome C from the inter-membrane space of mitochondria is a known trigger of apoptosis in cells. Cytochrome C is thought to directly facilitate activation of caspases. Accordingly, compounds which perturb mitochondrial function (eg, by binding to ANT and inducing the MPT) can result in increased cellular levels of Cytochrome C in proliferating cells (relative to non-proliferating cells), and may have the potential to be therapeutically useful for treating various diseases and conditions in vertebrates.

Examples of disorders and diseases may be grouped into broad categories such as the following: angiogenesis-dependent diseases, cellular proliferative diseases (e.g. psoriasis, IBD, malignancies, restenosis), inflammatory disorders, auto-immune diseases, blood vessel diseases, thrombosis, cancer, neurodegenerative disorders (e.g. Alzheimer's disease, Parkinson's disease), myelodysplastic syndromes, ischaemia/repurfusion injury and organ transplant injury.

Typically, the cancer is selected from the group consisting of carcinogenic tumours, tumours of epithelial origin, such as colo-rectal cancer, breast cancer, lung cancer, head and neck tumours, hepatic cancer, pancreatic cancer, ovarian cancer, gastric cancer, brain cancer, bladder cancer, prostate cancer and urinary/genital tract cancer; mesenchymal tumours, such as sarcoma; and haemopoietic tumours such as B cell lymphoma.

Typically, the cancer is a haematological tumour. More typically, the cancer is a solid tumour.

Other potential therapeutic applications of the present invention include treatment of inflammatory disorders and/or auto-immune diseases, examples of which include the following: rheumatoid arthritis, seronegative arthritides and other inflammatory arthritides, systemic lupus erythematosus, polyarteritis and related syndromes, systemic sclerosis, Sjögren's syndrome and other inflammatory eye disease, mixed connective tissue disease, polymyositis and dermatomyositis, polymyalgia rheumatica and giant cell arteritis, inflammatory joint disease, non-inflammatory arthropathies and soft tissue rheumatism, algodystrophy.

Examples of blood vessel disease and thrombosis include the following: progression of atherosclerosis; cerebrovascular accidents such as transient ischaemic, completed stroke, and after carotid surgery; acute myocardial infarction (primary and secondary); angina; occlusion of coronary artery bypass graft; occlusion following percutaneous transluminal coronary angioplasty; occlusion following coronary stenting; vascular occlusion in peripheral arterial disease; venous thromboembolic disease following surgery, or during pregnancy, or during immobilisation.

Examples of small vessel disease include the following: glomerulonephritis; thrombotic thrombocytopenic purpura; the haemolytic uraemic syndrome; placental insufficiency and preeclampsia.

The present invention may also have applications in the treatment of vascular syndromes and myeloproliferative diseases.

The present invention may also find use in identifying compounds which prevent thrombosis formation in the following situations: artificial/prosthetic vascular shunts and grafts; prosthetic heart valves; cardiopulmonary bypass procedures; haemoperfusion and haemodialysis.

Typically, compounds identified in accordance with the invention may be used in combination with other known treatments, such as surgery and/or therapeutic agents, including chemotherapeutic or radiotherapeutics. For example, when used in the treatment of solid tumours, compounds identified in accordance with the present invention may be administered with chemotherapeutic agents such as: adriamycin, taxol, fluorouricil, melphalan, cisplatin, alpha interferon, COMP (cyclophosphamide, vincristine, methotrexate and prednisone), etoposide, mBACOD (methotrexate, bleomycin, doxorubicin, cyclophosphamide, vincristine and dexamethasone), PROMACE/MOPP (prednisone, methotrexate (w/ leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; ethyenimines including thiotepa and hexamethylmelamine; folic acid analogues including methotrexate; pyrimidine analogues including 5-fluorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar.

Typically, the physiological system to be treated in accordance with the present invention (e.g, the hepatic system, pancreatic system) may be isolated by or during surgery prior to administration of the system of the invention.

Single or multiple administrations of the compounds or pharmaceutical compositions can be carried out with dose levels and pattern being selected by the treating physician. Regardless, the compounds or pharmaceutical compositions identified according to the present invention should be administered so as to provide a quantity of the compound sufficient to effectively treat the patient.

One skilled in the art would be able, by routine experimentation, to determine an effective, non-toxic amount of the compounds or pharmaceutical compositions used in accordance with the invention which would be required to detect apoptotic cells and/or treat or prevent the disorders and diseases. Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

In relation to the arsenoxide (or arsenoxide equivalent) compound disclosed herein, an effective dosage may be in the range of about 0.0001 mg to about 100 mg compound per kg body weight per 24 hours. For example, an effective dosage may be in the range of about 0.001 mg to about 100 mg compound per kg body weight per 24 hours. For example, an effective dosage may be in the range of about 0.01 mg to about 50 mg compound per kg body weight per 24 hours. For example, an effective dosage may be in the range of about 0.1 mg to about 20 mg compound per kg body weight per 24 hour. For example, an effective dosage may be in the range of about 0.1 mg to about 10 mg compound per kg body weight per 24 hours.

In relation to an additional active agent used together with a compound identified in accordance with the present invention, an effective dosage may be in the range of about 0.0001 mg to about 100 mg agent per kg body weight per 24 hours, preferably about 0.001 mg to about 100 mg agent per kg body weight per 24 hours, more preferably about 0.01 mg to about 50 mg agent per kg body weight per 24 hours, even more preferably about 0.1 mg to about 20 mg agent per kg body weight per 24 hours, even more preferably still about 0.1 mg to about 10 mg agent per kg body weight per 24 hours.

Delayed release formulations are also included in the scope of the present invention.

Typically the compound(s) may be administered for the duration of the condition being treated.

Further, it will be apparent to one of ordinary skill in the art that the optimal quantity and spacing of individual dosages of a compound used in accordance with the present invention will be determined by the nature and extent of the condition being treated, the form, route and site of administration, and the nature of the particular vertebrate being treated. Also, such optimum conditions can be determined by conventional techniques.

It will also be apparent to one of ordinary skill in the art that the optimal course of treatment, such as, the number of doses of the compound given per day for a defined number of days, can be ascertained by those skilled in the art using conventional course of treatment determination tests.

Whilst the compounds identified in accordance with the process(es) of the present invention may be administered alone, it is generally preferable that the compound be administered as a pharmaceutical composition/formulation. In general pharmaceutical formulations may be prepared according to methods which are known to those of ordinary skill in the art and accordingly may include a pharmaceutically acceptable carrier, diluent and/or adjuvant.

The invention will now be illustrated with reference to the following examples.

Example 1

Synthesis of Compounds

Methods

Synthesis of GSAA

BRAA was prepared by a modification of the method described in Donoghue et al (2000) and WO 01/21628. p-Arsanilic acid (20.6 g, 95 mmol) was added in portions to a solution of sodium carbonate (20 g, 189 mmol) in water (200 mL). When all solids had dissolved, the solution was found to be pH 10, and was chilled at 4° C. for 2 hours. Bromoacetyl bromide (15 mL, 173 mmol) in dry dichloromethane (35 mL) was added in two portions, each addition followed by vigorous shaking for 2 to 3 min. The mixture was allowed to stand for a few minutes, and the lower organic layer was drained off. 4-(N-(Bromoacetyl)amino)benzenearsonic acid (BRAA) was precipitated by acidification of the solution to about pH 2-3 with the dropwise addition of 98% sulfuric acid, collected by vacuum filtration, and dried, giving BRAA as a white solid.

BRAA (3.38 g, 10 mmol), reduced glutathione (3.23 g, 10.5 mmol) and sodium bicarbonate (3.15 g, 37.5 mmol) were mixed together, and the solid mixture was dissolved in portions in 0.5 M bicarbonate buffer (100 mL). The clear solution was found to be pH 9, and was thoroughly mixed and left overnight at room temperature. On the following day, the solution was acidified to neutral pH with the dropwise addition of 32% hydrochloric acid, and the product precipitated from absolute ethanol (1 L) by dropwise addition of the acidified solution to the well-stirred alcohol. The mixture was stirred at room temperature for 1 hour, and then left for 3 hours until the precipitate had settled. The clear ethanolic solution was decanted until ~300 mL were left, and then this was swirled and centrifuged at 2000 g for 5 min. The product 4-(N—((S-glutathionyl)acetyl)amino)-benzenearsonic acid (GSAA) was washed by re-suspension in fresh absolute ethanol and centrifuged again. The washing was repeated two more times, and the final suspension was dried to a white solid, GSAA, by rotary evaporation. The GSAA was characterised by $^1$H-NMR (D$_2$O, 300 MHz) and $^{13}$C-NMR (D$_2$O, 75 MHz) and has a molecular weight of 564.

Synthesis of GSAO

The complete synthesis of GSAO is described in International patent application WO 01/21628, the entire contents of which are incorporated herein by cross-reference. BRAA was prepared as described above. BRAA was then converted to 4-(N-(bromoacetyl)amino)-benzenearsonous acid (BRAO) using the method described in Donoghue et al (2000). The procedure for the conversion of BRAO to GSAO is a modification of that described in Donoghue et al. (2000), as follows. Reduced glutathione (16 g, 52 mmol) was dissolved in deoxygenated water (1 L) under a nitrogen atmosphere (deoxygenated water was prepared by boiling followed by cooling to room temperature, all the time under an atmosphere of nitrogen). BRAO (25 g, 77 mmol) was suspended in the solution, and vigorous stirring of the mixture was applied until the undissolved BRAO had lost all tendency to float, at which point the rate of stirring was decreased. Triethylamine (16 mL, 11.6 g, 115 mmol) was added, and the mixture was stirred for at least 18 hours, all the time under nitrogen. Some colourless solid was removed by rapid vacuum filtration, and the filtrate was concentrated to a viscous gel on a rotary evaporator. The gel was diluted with ethanol (250 mL), the rate of stirring was increased, and then acetone (250 mL) was added, with formation of a white solid. After stirring for 2 hours under nitrogen, the solid was collected by vacuum filtration, and dried at room temperature under vacuum to a constant weight. Analysis of the material by $^1$H-NMR allowed the amount of triethylamine to be determined. An equivalent amount of sodium hydroxide (ie. 1 mmol NaOH per mmol triethylamine) was added in the form of a 10 M aqueous solution to a solution of the material in the minimum amount of deoxygenated water. The solution was stirred under nitrogen for 2 hours, and GSAO (as the sodium salt) was obtained by removal of the solvent on a rotary evaporator. The GSAO was characterised by the following methods: $^1$H-NMR (D$_2$O, 400 MHz), $^{13}$C-NMR (D$_2$O, 100 MHz), HPLC, and infrared spectroscopy (nujol mull). The elemental analysis was consistent with a composition of GSAO.2H$_2$O, and the mass spectrum gave the parent molecular ion at 549.1 m.u. [GSAO+H]$^+$. The purity of GSAO was >94% by HPLC.

Synthesis of GSCA

GSCA was prepared in a similar manner to GSAA, using 4-aminobenzoic acid instead of p-arsanilic acid as follows. A chilled alkaline solution of 4-aminobenzoic acid (13 g, 95 mmol) was prepared as described above for p-arsanilic acid, and reacted in an identical manner with bromoacetyl bromide. The lower organic layer was drained off, and 4-(N-(bromoacetyl)amino)-benzoic acid (BRCA) precipitated directly from solution by itself. Following the rest of the procedure for GSAA exactly using BRCA (2.58 g, 10 mmol) in place of BRAA gave GSCA as a white solid after rotary evaporation. The GSCA was characterised by $^1$H-NMR (D$_2$O, 300 MHz) and $^{13}$C-NMR (D$_2$O, 75 MHz) and the disodium salt has a molecular weight of 528.

Synthesis of Biotin and Fluorescein Derivatives of GSAO and GSAA

GSAO-B was produced as described by Donoghue et al. (2000) and has a molecular weight of 1001. A solution of fluorescein-5-EX succinimidyl ester (Molecular Probes, Eugene, Oreg.) (2.4 mg, 4.1 µmol) in DMSO (240 µL) was added to GSAO or GSAA (33.8 mM) in Mes buffer, pH 5.5 (5 mM, 473 µL), the mixture was diluted with bicarbonate buffer, pH 9 (0.5 M, 3.287 mL) and allowed to stand at room temperature for 80 min. The reaction was then diluted with glycine (100 mM) in PBS (4 mL), and allowed to stand at room temperature overnight. The final solution contained trivalent arsenical (2.00 mM) and glycine (50 mM). The molar ratio of fluorescein-5× to GSAO or GSAA was ~1.5:1. The molecular weights of GSAO- and GSAA-fluorescein (GSAO-F and GSAA-F) are 1024 and 1040, respectively.

Synthesis of 2-(2-Bromoacetyl-o-amino)benzenearsonic acid o-Arsanilic acid (4.70 g, 21.7 mmol) was dissolved in 1.85 M KOH (25 mL) then treated with $Na_2CO_3$ (6 g) and diluted with $H_2O$ (25 mL). The solution was cooled in ice for 30 min then added to a 250 mL separating funnel. A solution of bromoacetyl bromide (4 mL, 46.0 mmol) in $CH_2Cl_2$ (20 mL) was added cautiously to the separating funnel over approximately 30 mins with frequent shaking and release of $CO_2$ (g). After $CO_2$ evolution had ceased, the $CH_2Cl_2$ was separated and the aqueous layer was acidified with conc. $H_2SO_4$. A white precipitate resulted which was collected by filtration (6 g, 82% yield).

Synthesis of 2-(2-Bromoacetyl-o-amino)benzenearsonous acid 2-(2-Bromoacetylamino)benzenearsonic acid (6 g, 17.8 mmol) was dissolved in HBr/MeOH (1:1). NaI (80 mg) was added and the reaction was purged with $N_2$ and cooled to 0° C. $SO_2$ was bubbled through at ca. 4 bubbles/second and after 15 min a white precipitate started to form. $SO_2$ was bubbled through for a further 2.5 h as the reaction was warmed to room temperature. The reaction was purged with $N_2$ for 10 min, and the solid was collected by filtration washing with $H_2O$ (×3), ether (×2) to give 1.35 g of 2-(2-bromoacetylamino)benzenearsonous acid. A further 0.25 g was obtained from the initial filtrate. Total yield (1.60 g, 28%).

Synthesis of 2-(2-Bromoacetyl-p-amino)benzenearsonic acid p-Arsanilic acid (20 g, 92 mmol) was dissolved in 1.85 M KOH (100 mL) then treated with $Na_2CO_3$ (30 g) and $H_2O$ (100 mL). The solution was cooled in ice for 30 min then added to a 500 mL separating funnel. A solution of bromoacetyl bromide (16 mL, 184 mmol) in $CH_2Cl_2$ (60 mL) was added cautiously to the separating funnel with frequent shaking and release of $CO_2$ (g). Addition took about 2 h. After $CO_2$ (g) evolution had ceased, the $CH_2Cl_2$ was separated and the aqueous layer was acidified with 98% $H_2SO_4$. A white precipitate resulted which was collected by filtration and dried for 18 h in a desiccator. Obtained 24 g (72 mmol, 78% yield).

Synthesis of 2-(2-Bromoacetyl-p-amino)benzenearsonous acid 2-(2-Bromoacetyl-p-amino)benzenearsonic acid (15 g, 45 mmol) was dissolved in 150 mL 48% HBr(aq)/MeOH (1:1). NaI (200 mg, 13 mmol) was added and the reaction was purged with N2 and cooled on ice. $SO_2$ (g) was bubbled through at ca. 2 bubbles/second and after 5 h a white precipitate started to form. $SO_2$ (g) was bubbled through for a further 2 h as the reaction was warmed to 25° C. The reaction was purged with N2 for 10 min, and the solid was collected by filtration washing with $H_2O$ (×3), ether (×2) to give 1.35 g of 2-(2-Bromoacetylamino)-benzenearsonous acid. Obtained 5.5 g (17 mmol, 38% yield).

Synthesis of $NH_2$-Glu-Cys-($CH_2CONH$—$C_6H_4$-o-As{OH}$_2$)-Gly-OH "o-GSAO" (1)

2-(2-Bromoacetylamino)benzenearsonous acid (288 mg, 0.90 mmol) was suspended in degassed $H_2O$ (5 mL). $NEt_3$ (250 µL, 1.7 mmol) was added followed by glutathione (160 mg, 0.521 mmol). The pH of the reaction mixture was confirmed to be pH≥8. The white suspension was stirred vigorously under $N_2$ for 20 h. The reaction was filtered through a glass-fritted filter and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The supernatant was centrifuged and decanted leaving a white solid, which was decanted and further dried under vacuum. The dried powdery o-GSAO was dissolved in $H_2O$ (4 mL) and injected into the semi-preparative HPLC, $C_{18}$ Vydac Protein & Peptide column. Buffer A: 0.1% TFA in filtrated and degassed water; Buffer B: 0.1% TFA in filtrated and degassed acetonitrile-filtrated and degassed water (9:1). Fractions were collected and freeze-dried. The structure of o-GSAO was confirmed by LC-MS ($M^+$ 548.4) and by $^1$H-NMR. Purity by HPLC was 96.9% to 98.8% for 4 batches.

Synthesis of retro-HO-Cys-($CH_2CONHC_6H_4$-p-As{OH}$_2$)-carbonyl-Glu-OH (3)

2-(2-Bromoacetyl-p-amino)benzenearsonous acid (80 mg, 0.25 mmol) was suspended in degassed $H_2O$ (2 mL). $NEt_3$ (70 µL, 0.5 mmol) was added followed by retro-HO-Cys-carbonyl-Glu-OH (50 mg, 0.17 mmol). The pH of the solution was confirmed to be pH≥8. The white suspension was stirred vigorously under $N_2$ for 16 h. The reaction was filtered through a disposable 0.45 µM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of retro-HO-Cys-($CH_2CONHC_6H_4$-p-As{OH}$_2$)-carbonyl-Glu-OH (4)

2-(2-Bromoacetyl-p-amino)benzenearsonous acid (80 mg, 0.25 mmol) was suspended in degassed $H_2O$ (2 mL). $NEt_3$ (70 µL, 0.5 mmol) was added followed by retro-HO-Cys-carbonyl-Glu-OH (50 mg, 0.17 mmol). The pH of the solution was confirmed to be pH≥8. The white suspension was stirred vigorously under $N_2$ for 16 h. The reaction was filtered through a disposable 0.45 µM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS.

The product was purified by semi-preparative RP-HPLC. The fractions were dried on speed-vac.

Synthesis of H-Arg-Gly-Asp-Cys(CH$_2$CONHC$_6$H$_4$-p-As{OH}$_2$)—OH (6)

2-(2-Bromoacetyl-p-amino)benzenearsonous acid (80 mg, 0.25 mmol) was suspended in degassed H$_2$O (4 mL). NEt$_3$ (70 μL, 0.5 mmol) was added followed by H-Arg-Gly-Asp-Cys-OH (50 mg, 0.11 mmol). The pH of the solution was confirmed to be pH≥8. The white suspension was stirred vigorously under N$_2$ for 16 h. The reaction was filtered through a disposable 0.45 μM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of H-Gly-Gly-Cys(CH$_2$CONHC$_6$H$_4$-p-As{OH}$_2$)—OH (7)

2-(2-Bromoacetyl-p-amino)benzenearsonous acid (288 mg, 0.90 mmol) was suspended in degassed H$_2$O (4 mL). NEt$_3$ (220 μL, 1.6 mmol) was added followed by H-Gly-Gly-Cys-OH (141.2 mg, 0.6 mmol). The pH of the solution was confirmed to be pH≥8. The white suspension was stirred vigorously under N2 for 16 h. The reaction was filtered through a disposable 0.45 μM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of H-Val-Thr-Cys(CH$_2$CONHC$_6$H$_4$-p-As{OH}$_2$)-Gly-OH (8)

2-(2-Bromoacetyl-p-amino)benzenearsonous acid (80 mg, 0.25 mmol) was suspended in degassed H$_2$O (4 mL). NEt$_3$ (70 μL, 0.5 mmol) was added followed by H-Val-Thr-Cys-Gly-OH (50 mg, 0.13 mmol). The pH of the solution was confirmed to be pH≥8. The white suspension was stirred vigorously under N$_2$ for 16 h. The reaction was filtered through a disposable 0.45 μM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of H-Cys-(CH$_2$CONHC$_6$H$_4$-p-As{OH}$_2$)-Tyr-Phe-Gln-Asn-Cys-(CH$_2$CONHC$_6$H$_4$-p-As{OH}$_2$)—OH (9)

Reduction of pressionoic acid: dissolve the peptide in 10 mL 0.1 M sodium bicarbonate, DTT solution (99 mg, 0.65 mmol) degazed with N$_2$. The pH of the solution was confirmed to be pH≥8 and blanket mixture with N$_2$. After 2 h acidify solution with AcOH, freeze-dry mixture. Purify by semi-preparative RP-HPLC after dissolving in 0.1% aqueous TFA solution. Freeze-dry.

2-(2-Bromoacetyl-p-amino)benzenearsonous acid (26 mg, 0.081 mmol, 1.4 eq.) was suspended in degassed H$_2$O (3 mL). Net$_3$ (20 μL, 0.14 mmol) was added followed by pressionoic acid (22 mg, 0.028 mmol). The pH of the solution was confirmed to be pH≥8. The white suspension was stirred vigorously under N$_2$ for 16 h. The reaction was filtered through a disposable 0.45 μM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of 3-S—(CH$_2$CONHC$_6$H$_4$-p-As{OH}$_2$)-1-propanesulfonic acid (10)

2-(2-Bromoacetyl-p-amino)benzenearsonous acid (288 mg, 0.90 mmol) was suspended in degassed H$_2$O (4 mL). Net$_3$ (220 μL, 1.6 mmol) was added followed by 3-mercaptopropanesulfonic acid (106.9 mg, 0.6 mmol). The pH of the solution was confirmed to be pH≥8. The white suspension was stirred vigorously under N$_2$ for 16 h. The reaction was filtered through a disposable 0.45 μM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of 3-S—(CH$_2$CONHC$_6$H$_4$-p-As{OH}$_2$)-1-propionic acid (11)

2-(2-Bromoacetyl-p-amino)benzenearsonous acid (288 mg, 0.90 mmol) was suspended in degassed H$_2$O (4 mL). Net$_3$ (210 μL, 1.5 mmol) was added followed by mercaptopropionic acid (53 μL, 0.6 mmol). The pH of the solution was confirmed to be pH≥8. The white suspension was stirred vigorously under N$_2$ for 16 h. The reaction was filtered through a disposable 0.45 μM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of 1-S—(CH$_2$CONHC$_6$H$_4$-p-As{OH}$_2$)-mercaptosuccinic acid (13)

2-(2-Bromoacetyl-p-amino)benzenearsonous acid (288 mg, 0.90 mmol) was suspended in degassed H$_2$O (4 mL). Net$_3$ (210 μL, 1.5 mmol) was added followed mercaptosuccinic acid (90 mg, 0.6 mmol). The pH of the solution was confirmed to be pH≥8. The white suspension was stirred vigorously under N$_2$ for 16 h. The reaction was filtered through a disposable 0.45 μM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of 1-S—(CH$_2$CONHC$_6$H$_4$-p-As{OH}$_2$)-β-D-glucose (14)

2-(2-Bromoacetyl-p-amino)benzenearsonous acid (288 mg, 0.90 mmol) was suspended in degassed H$_2$O (4 mL). Net$_3$ (210 μL, 1.5 mmol) was added followed by 1-thio-β-D-glucose (130.9 mg, 0.6 mmol). The pH of the solution was confirmed to be pH≥8. The white suspension was stirred vigorously under N$_2$ for 16 h. The reaction was filtered through a disposable 0.45 μM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of 3-S—(CH$_2$CONHC$_6$H$_4$-p-As{OH}$_2$)-1,2-propanediol (15)

2-(2-Bromoacetyl-p-amino)benzenearsonous acid (288 mg, 0.90 mmol) was suspended in degassed H$_2$O (4 mL). Net$_3$ (210 μL, 1.5 mmol) was added followed by 3-mercapto-1,2-propanediol (65 μL, 0.6 mmol). The pH of the solution was confirmed to be pH≥8. The white suspension was stirred vigorously under N$_2$ for 16 h. The reaction was filtered through a disposable 0.45 μM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of 5-S—(CH$_2$CONHC$_6$H$_4$-p-As{OH}$_2$)-1-tetrazolacetic acid (21)

2-(2-Bromoacetyl-p-amino)benzenearsonous acid (288 mg, 0.90 mmol) was suspended in degassed H$_2$O (5 mL). Net$_3$ (210 μL, 1.5 mmol) was added followed by 5-mercapto-tetrazolacetic acid (110 mg, 0.6 mmol). The pH of the solution was confirmed to be pH≥8. The white suspension was stirred vigorously under N$_2$ for 16 h. The reaction was filtered through a disposable 0.45 μM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of H-Gly-Gly-Cys(CH$_2$CONHC$_6$H$_4$-o-As{OH}$_2$)—OH (22)

2-(2-Bromoacetyl-o-amino)benzenearsonous acid (160 mg, 0.5 mmol) was suspended in degassed H$_2$O (1 mL). Net$_3$ (140 μL, 1.0 mmol) was added followed by H-Gly-Gly-Cys-OH (61 mg, 0.26 mmol). The pH of the solution was confirmed to be pH≥8. The white suspension was stirred vigorously under N$_2$ for 20 h. The reaction was filtered through a disposable 0.45 μM disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Synthesis of H-Val-Thr-Cys(CH$_2$CONHC$_6$H$_4$-o-As{OH}$_2$)-Gly-OH (23)

2-(2-Bromoacetyl-o-amino)benzenearsonous acid (80 mg, 0.25 mmol) was suspended in degassed H$_2$O (1 mL). Net$_3$ (70 μL, 0.50 mmol) was added followed by H-Val-Thr-Cys-Gly-OH (50 mg, 0.13 mmol). The pH of the solution was confirmed to be pH≥8. The white suspension was stirred vigorously under N$_2$ for 20 h. The reaction was filtered through a disposable 0.45 μM a disk and the filtrate concentrated on a rotary evaporator. The residue was transferred to a plastic tube and 2 mL EtOH/acetone (1:1) was added resulting in a white precipitate. The tube was capped and stored at 4° C. for 1.5 h. The solution was centrifuged and decanted leaving a white solid, which was redissolved in MeCN-Water. The crude sample was analysed by RP-HPLC and LCMS. The product was purified by semi-preparative RP-HPLC. The fractions were dried on speed-vac.

Assay of Arsenical Concentration

The concentrations of GSAO, GSAO-B and GSAO-F were measured by titrating with dimercaptopropanol and calculating the remaining free thiols with 5,5'-dithiobis(2-nitrobenzoic acid) (Sigma, St. Louis, Mo.) (Donoghue et al., 2000). The conjugates were sterile filtered and stored at 4° C. in the dark until use. There was no significant loss in the active concentration of stock solutions of the arsenicals for at least a week when stored under these conditions.

Example 2

GSAO Triggered MTP Opening by Reacting with and Perturbing ANT

Methods

Mitochondria Swelling Assay

Mitochondria were isolated from the livers of ~250 g male Wistar rats using differential centrifugation as described previously (Schnaitman & Greenawalt, 1968). The final mitochondrial pellet was resuspended in 3 mM HEPES-KOH, pH 7.0 buffer containing 213 mM mannitol, 71 mM sucrose and 10 mM sodium succinate at a concentration of 30 mg of protein per mL. MPT induction was assessed spectrophotometrically by suspending the liver mitochondria at 0.5 mg of protein per mL at 25° C. in 3 mM HEPES-KOH, pH 7.0 buffer containing 75 mM mannitol, 250 mM sucrose, 10 mM sodium succinate, and 2 μM rotenone. All buffer components were from Sigma, St. Louis, Mo. The arsenical derivatives and GSCA were dissolved in phosphate-buffered saline (PBS) containing 100 mM glycine. ANT-binding compounds employed were CsA, BKA and ADP (Sigma, St. Louis, Mo.). Reagent concentrations are indicated in the figure legends. Swelling was measured by monitoring the associated decrease in light scattering at 520 nm using a Molecular Devices Thermomax Plus (Palo Alto, Calif.) microplate reader.

Binding of GSAO to ANT

Rat liver mitochondria were suspended at 1 mg of protein per mL at 25° C. in 3 mM HEPES-KOH, pH 7.0 buffer containing 213 mM mannitol, 71 mM sucrose and 10 mM sodium succinate and incubated with 100 μM GSAO-B in absence or presence of 400 μM 2,3-dimercaptopropanol (Fluka, Buchs, SG, Switzerland) at room temperature on a rotating wheel for 1 h. The labelled mitochondria were washed three times with PBS and sonicated in 0.3 mL of ice-cold 25 mM Tris, pH 7.4 buffer containing 140 mM NaCl, 2.7 mM KCl, 0.5% Triton X-100, 0.05% Tween-20, 10 μM leupeptin, 10 μM aprotinin, 50 μg·mL$^{-1}$ 4,2-(aminoethyl)-benzene sulfonyl fluoride and 5 mM EDTA. Lysate was clarified by centrifugation at 18000 g for 10 min at 4° C. and incubated with 30 μL of streptavidin-dynabeads (Dynal, Oslo, Norway) for 60 min at 4° C. on a rotating wheel to isolate the biotin-labelled proteins. The beads were washed 5 times with sonication buffer and the biotin-labelled proteins were released from the beads by boiling in 30 μl of SDS-Laemmli buffer for 2 minutes. Samples were resolved on 8-16% gradient iGels under reducing conditions and transferred to PVDF membrane. Proteins were detected by Western blot using a 1:500 dilution of goat anti-human ANT polyclonal antibody (Santa Cruz Biotechnology, Santa Cruz, Calif.) and 1:2000 dilution of rabbit anti-goat peroxidase-conjugated antibodies (Dako, Carpinteria, Calif.).

Labelling of ANT with Eosin-5-Maleimide

Rat liver sub-mitochondrial particles were prepared by sonication and differential centrifugation according to Majima et al. (1998). The particles were suspended at 20 mg of protein per mL in 10 mM Tris, pH 7.2 buffer containing 250 mM sucrose and 0.2 mM EDTA and incubated without or with 200 nmol GSAO per mg of protein for 10 min at 25° C., followed by 20 nmol of eosin-5-maleimide per mg of protein for 1 min at 0° C. in the dark. The labelling was terminated by addition of 10 μmol of dithiothreitol per mg of protein. The proteins were resolved on 4-20% gradient iGels and the eosin-labelled ANT was visualised by UV transillumination using a Fluor-S™ MultiImager (Bio-Rad, Hercules, Calif.).

Results

Figure 1B:
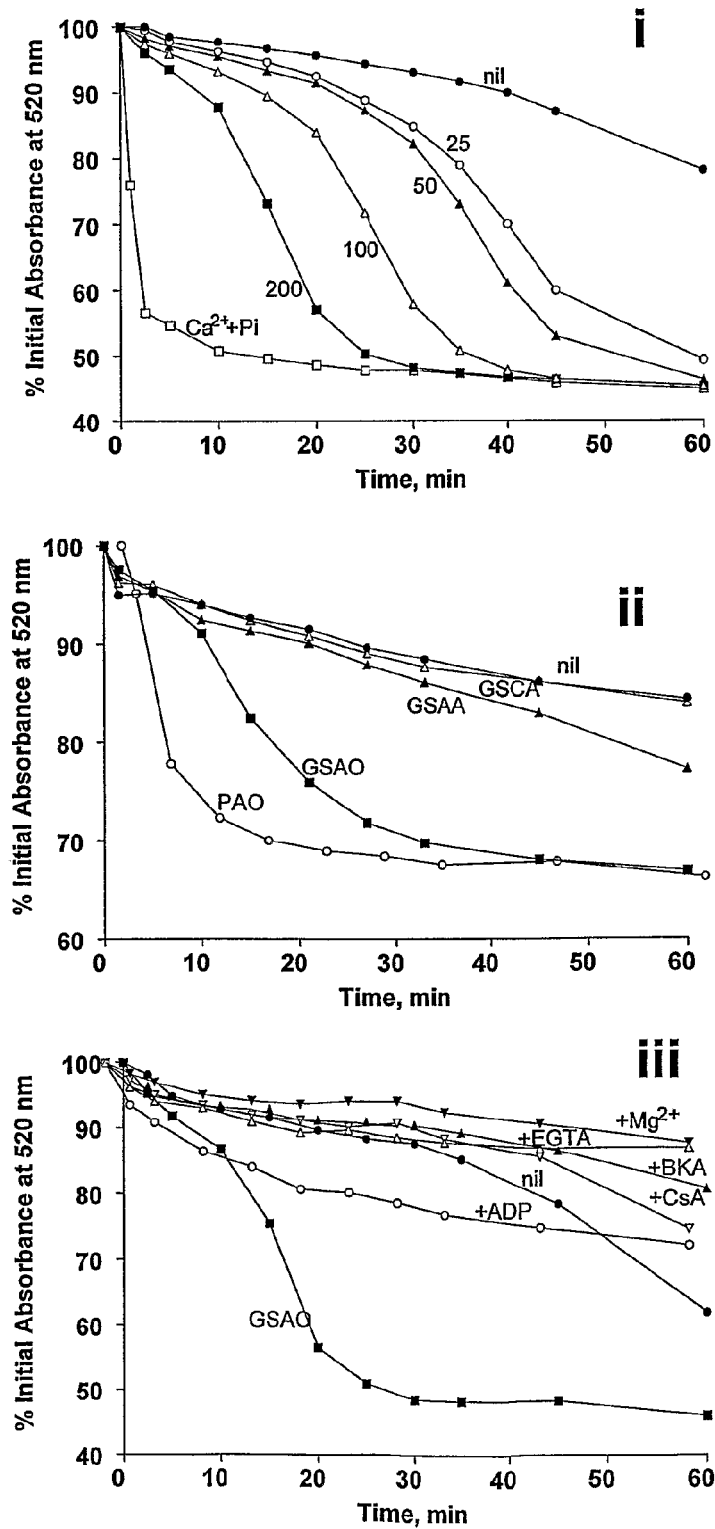

GSAO (FIG. 1A) triggered swelling of isolated rat liver mitochondria (FIG. 1Bi). The rate of swelling increased with increasing GSAO concentration and time of incubation. The trivalent arsenical moiety of GSAO was responsible for this activity as the corresponding pentavalent arsenical (4-(N—((S-glutathionyl)acetyl)amino)benzenearsonic acid, GSAA) or carboxylic acid (4-(N—((S-glutathionyl)acetyl)amino) benzoic acid, GSCA) compounds (FIG. 1A) were without effect (FIG. 1Bii). Positive controls for pore opening were Ca$^{2+}$ and Pi ions (FIG. 1Bi) and PAO (FIG. 1Bii).

ANT activity is controlled by the binding of Ca$^{2+}$, cyclophilin D and adenine nucleotides. Cyclophilin D (Crompton et al., 1988) and adenine nucleotides (Haworth & Hunter, 1979a,b) bind to the matrix side of ANT, while the site(s) for interaction of Ca$^{2+}$ has yet to be determined. The primary trigger for opening of the MPTP is a rise in matrix Ca$^{2+}$ concentration. Chelation of Ca$^{2+}$ with EGTA blocks pore opening. The specificity of the trigger site for Ca$^{2+}$ appears to be absolute as other divalent metal ions such as Mg$^{2+}$ act as inhibitors (Haworth & Hunter, 1979a). Binding of cyclophilin D to ANT is necessary for pore opening at sub-millimolar Ca$^{2+}$ concentrations (Halestrap et al., 2002). Cyclosporin A (CsA) blocks pore opening by binding to cyclophilin D and displacing it from ANT (Crompton et al., 1988). Matrix ADP is also an important modulator of pore opening that binds to ANT and decreases the sensitivity of the trigger site to Ca$^{2+}$ (Haworth & Hunter, 1979a,b). Bonkrekic acid (BKA) also interacts with ANT and decreases sensitivity to Ca$^{2+}$ (Hunter & Haworth, 1979).

Mg$^{2+}$, EGTA, CsA, ADP, and BKA all blocked the effect of GSAO on pore opening (FIG. 1Biii). These observations are consistent with a specific effect of GSAO on pore opening and support ANT as its target.

Figure 1C:
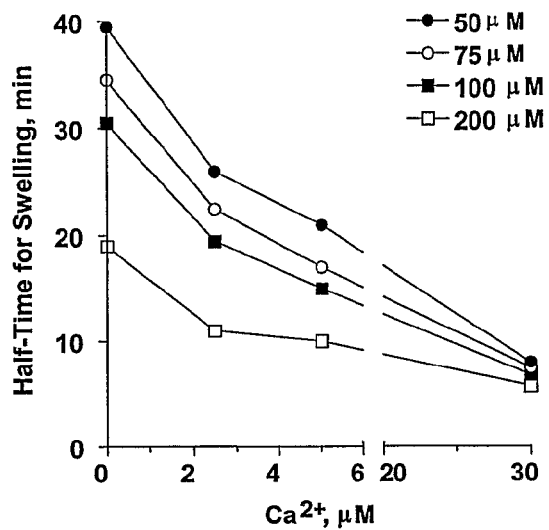

The half-time for GSAO mediated swelling of the mitochondria was reduced by added Ca$^{2+}$ (FIG. 1C). This result is consistent with GSAO cross-linking two of the three cysteine residues on ANT that protrude into the mitochondrial matrix.

Figure 1D:
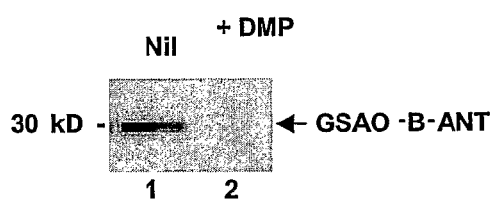
Figure 1E:
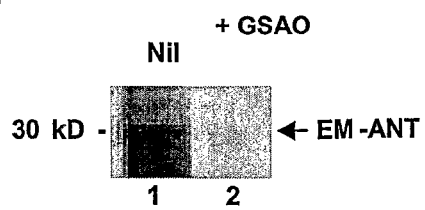

Direct interaction of ANT with a biotin-tagged GSAO (4-(N—(S—(N-(6-((6-((biotinoyl)amino)hexanoyl)amino)hexanoyl)-glutathionyl)acetyl)amino) phenylarsenoxide, GSAO-B) is shown in FIG. 1D. The labeling of ANT with GSAO-B was specific as it was competed for by a 4-fold molar excess of the small synthetic dithiol, dimercaptopropanol. Eosine-maleimide alkylates Cys$^{160}$ in ANT (Majima et al., 1998) and blocks ADP binding (Halestrap et al., 1997). GSAO competed for eosine-maleimide alkylation of ANT Cys$^{160}$ (FIG. 1E), which implied that GSAO cross-links Cys$^{160}$ and Cys$^{257}$.

Example 3

GSAO Concentrated in Mitochondria in Viable Cells

Methods

Cell Culture

Bovine aortic endothelial (BAE) cells (ATCC, Rockville, Md.) were cultured in DMEM supplemented with 10% foetal calf serum (FCS), 2 mM L-glutamine, and 5 U·mL$^{-1}$ penicillin/streptomycin (Gibco, Gaithersburg, Md.). The human microvascular endothelial cell line, HMEC-1 (Ades et al., 1992), was cultured in MCDB131 medium (Gibco) supplemented with 10% FCS, 2 mM L-glutamine, 5 U·mL$^{-1}$ penicillin/streptomycin, 10 ng·mL$^{-1}$ epidermal growth factor (Sigma, St. Louis, Mo.) and 1 μg·mL$^{-1}$ hydrocortisone (Sigma). Cell culture plasticware was purchased from Corning Costar (Corning, N.Y.). Trypsin/EDTA solution was from Gibco.

Immunocytochemistry and Confocal Microscopy

BAE cells were seeded at a density of 10$^4$ cells per well into 8-well Labtek glass chamber slides (Nunc, Naperville, Ill.) and allowed to adhere overnight. The cells were washed once and the medium was replaced with Hanks Balanced Salt Solution (HBSS) (Gibco). The cells were then incubated for 1 h with 50 μM GSAO-F, 50 μM GSAO-F and 250 μM dimercaptopropanol, or 50 μM GSAA-F. All cells were counterstained with 100 nM Mitotracker™ Red CMXRos (Molecular Probes, Eugene, Oreg.). The cells were then washed three times with HBSS, fixed for 10 min with 80% acetone and 20% methanol, and washed three times with HBSS. Slides were mounted in VectaShield antifade agent (Vector Laboratories, Burlingame, Calif.) and sealed with nail polish. Images were captured using a Leica DM IRB inverted microscope and confocal system, with Leica confocal software.

Results

Figure 2:
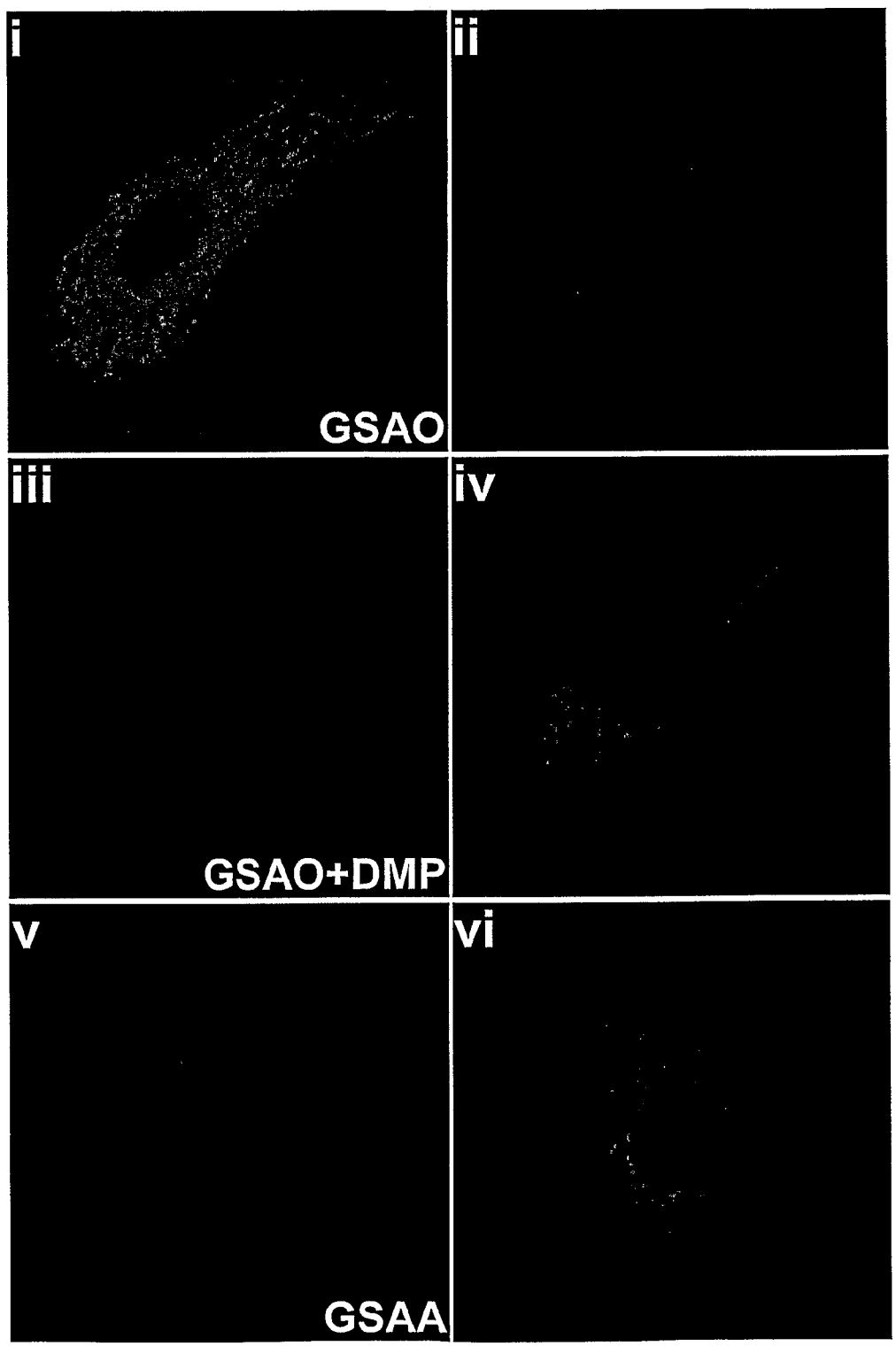
FIG. 2. GSAO concentrated in mitochondria in viable cells. Confocal microscopy of BAE cells incubated with GSAO-F (i) and Mitotracker Red (ii), showing colocalisation of the compounds in the mitochondria of a single cell. GSAO-F did not stain cells when incubated with DMP (iii and iv). The pentavalent arsenical, GSAA-F, also did not stain cells (v and vi).

A striking feature of GSAO was that it rapidly localised to mitochondria in viable bovine aortic (BAE) (FIG. 2) and human dermal microvascular (HMEC-1) (data not shown)

endothelial cells, GSAO was conjugated to fluorescein (GSAO-F) and its sub-cellular localisation was determined by confocal fluorescence microscopy. Mitochondrial staining was confirmed by colocalisation of GSAO-F with the red-fluorescent Mitotracker probe, which accumulates in the mitochondria of actively respiring cells (FIGS. 2ii, iv and vi). The mitochondrial accumulation of GSAO-F was specific for the dithiol reactivity of GSAO as it was abolished in the presence of a five-fold molar excess of the small synthetic dithiol, dimercaptopropanol (FIG. 2iii), and the corresponding pentavalent arsenical, GSAA-F, did not stain the cells (FIG. 2v). Mitochondrial localisation was also seen in BAE cells incubated with GSAO-B, followed by staining with streptavidin-Alexa Fluor 488 (data not shown).

ANT is abundant in the inner mitochondrial membrane. Sequestration of GSAO on the matrix face of ANT would drive entropic import of GSAO into the matrix. This mechanism is supported by the finding that GSAA, which has effectively the same charge and size as GSAO, did not react with ANT or accumulate in mitochondria.

Example 4

GSAO Inhibited ATP Production, Increased Superoxide Levels and Triggered Mitochondrial Depolarisation and Apoptosis in Proliferating, but not Growth-Quiescent, Endothelial Cells Methods
ATP Assays BAE cells in six-well culture plates were arrested for 24 h in 0.5% serum or left in 10% serum, then treated for 24 h with 0, 60 or 150 µM GSAO. The cells were washed once then resuspended in 0.4 mL PBS containing 0.3% bovine serum albumin. A 50 µl sample of cells was mixed with 50 µL water and 100 µL ATP releasing agent (Sigma) and ATP concentration was measured using a luciferin/luciferase ATP assay mix (Sigma). Light units were converted to ATP concentrations using an ATP standard in place of the 50 µL water. Cell number was counted using a Beckman Coulter Counter and mol of ATP was expressed per million cells.

Cell Proliferation Assays

BAE or HMEC-1 cells were seeded at a density of $10^4$ cells per cell into 96 well plates and allowed to adhere overnight and then treated as indicated. For experiments involving arrest of cell proliferation in 0.25% serum, the cells were seeded in medium containing 10% serum, allowed to adhere overnight, then washed with PBS and arrested for 24 h in medium containing 0.25% serum. Attached cells remaining after treatments were measured using methylene blue (Oliver et al., 1989).

Superoxide, Mitochondrial Membrane Potential, Mitochondrial Mass and Apoptosis Assays For measurements of superoxide levels with dihydroethidine, mitochondrial membrane potential with JC-1, mitochondrial mass with nonyl acridine orange, and apoptosis with annexin V, proliferating or growth-quiescent BAE cells were treated for 24 or 48 h with GSAO in six-well culture plates, then detached with trypsin/EDTA, washed once, and resuspended at $2\times10^6$ cells per mL in serum-free medium. Cells were then incubated for 15 min at room temperature with dihydroethidine (5 µM, Molecular Probes) or 30 min at room temperature with JC-1 (0.5 µg·mL$^{-1}$, Molecular Probes), annexin V-FITC (50 µl·mL$^{-1}$) (Pharmingen, La Jolla, Calif., USA), or acridine orange 10-nonyl bromide (5 µM, Molecular Probes). Cells were then washed once, resuspended in 0.5 mL serum-free medium, transferred to ice, and fluorescence was quantitated immediately by flow cytometry.

Results

GSAO concentrated in mitochondria in viable cells and perturbed mitochondrial function and cell viability. Proliferating cells having a greater mitochondrial mass and respiration than growth-quiescent cells. To test whether GSAO might have selective effects on proliferating cells, proliferating or growth-quiescent BAE cells were incubated for 48 h with increasing concentrations of GSAO.

Figure 3A:
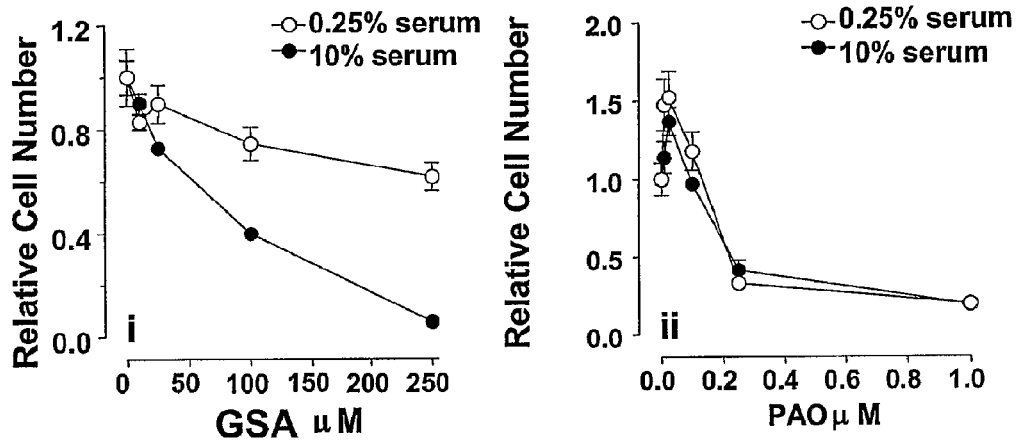
FIG. 3. GSAO triggered mitochondrial depolarisation and apoptosis in proliferating, but not growth-quiescent, endothelial cells. A GSAO reduced the viability of proliferating, but not growth-quiescent, endothelial cells. In contrast, PAO was equally toxic to both types of cell. BAE cells were arrested for 24 h in medium containing 0.25% serum, then cultured for a further 48 h in medium containing 0.25% or 10% serum, with GSAO (i) or PAO (ii). Number of attached cells after 48 h treatment was measured. Results are mean±SE of three experiments. B GSAO triggered mitochondrial depolarisation and induced apoptosis in BAE cells. Cells were cultured for 48 h in medium containing 10% serum and GSAO and then labelled with JC-1 or annexin V. The percent of cells positive for mitochondrial membrane depolarisation (JC-1 green/red fluorescence) and induction of apoptosis (annexin V binding) was measured. The same result was observed in two different experiments. C BAE cells were arrested for 24 h in medium containing 0.25% serum, then cultured for a further 48 h in medium containing 0.25% or 10% serum, with GSAO. In part i, cellular ATP levels were measured using a luciferin/luciferase assay. In part ii, mitochondrial mass was measured from uptake of nonyl acridine orange (NAO). D Superoxide level, measured with dihydroethidine, in BAE cells that had been cultured for 24 hr in medium containing 0.25% or 10% serum and then for a further 24 hr in the presence of GSAO.
Figure 3B:
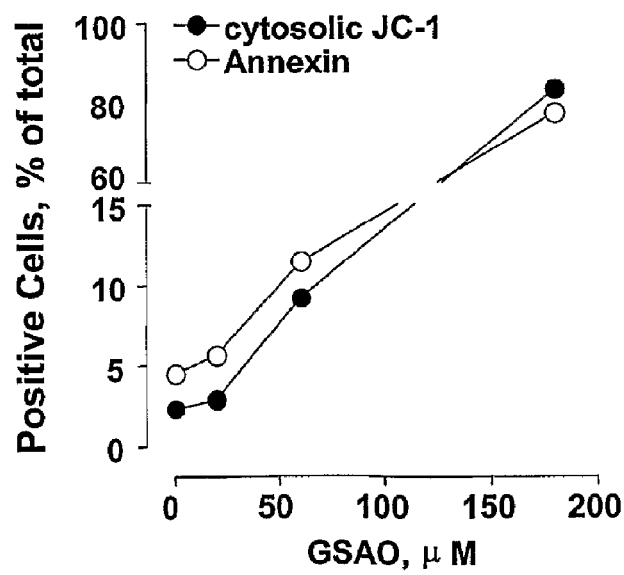
Figure 3C:
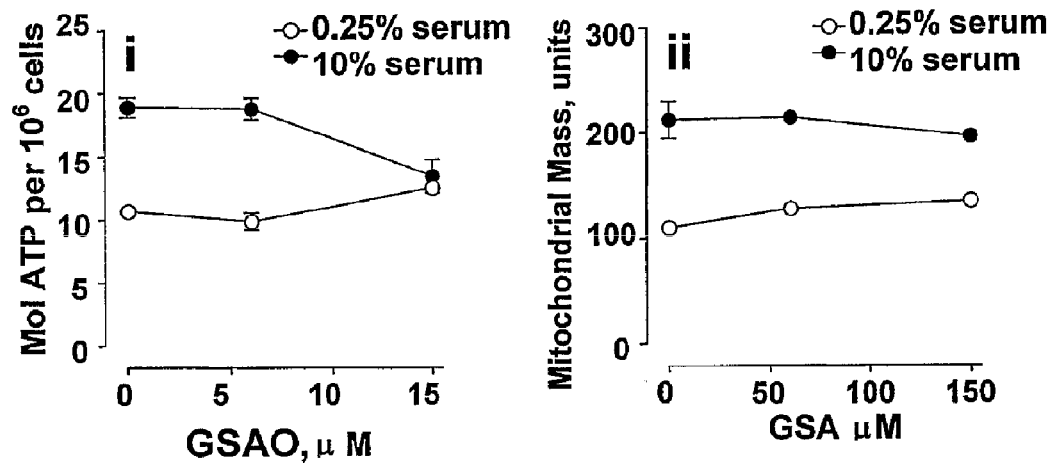
Figure 3D:
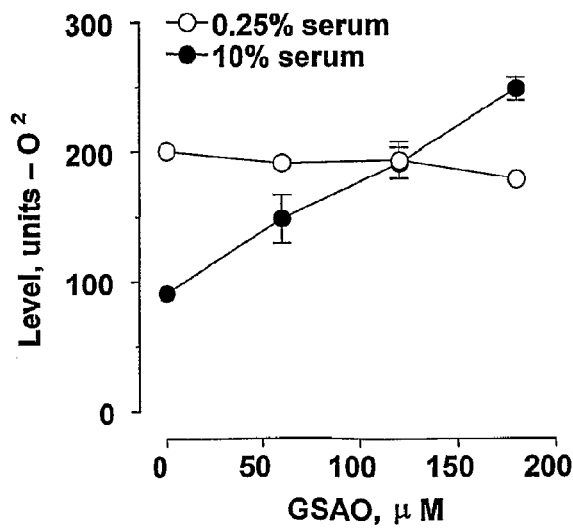

The GSAO $IC_{50}$ for reduction in viability of proliferating BAE cells was ~75 µM (FIG. 3Ai), whereas the compound had little effect on growth-quiescent cells. The control compounds, GSAA and GSCA, had no significant effect on the viability of proliferating BAE cells at concentrations up to 1.0 mM (data not shown). The effect of GSAO on proliferating cell viability was time-dependent. The GSAO $IC_{50}$ decreased from ~75 µM to ~25 µM when the incubation time increased from 48 to 72 h (data not shown). PAO, in contrast, was equally toxic to both proliferating and growth-quiescent BAE cells with an $IC_{50}$ of ~200 nM (FIG. 3A(ii)). The same results were observed with HMEC-1 cells (data not shown). GSAO's effect on proliferating endothelial cell viability was closely associated with loss of mitochondrial transmembrane potential and apoptosis (FIG. 3B). These parameters were measured using the JC-1 dye and FITC-conjugated annexin V, respectively. The ratio of distribution of JC-1 between the cytosol (green fluorescence) and mitochondria (red fluorescence) reflects mitochondrial transmembrane potential (Smiley et al., 1991) while annexin V binds to phosphatidylserine exposed on the surface of apoptotic cells.

Figures 4A, 4B:
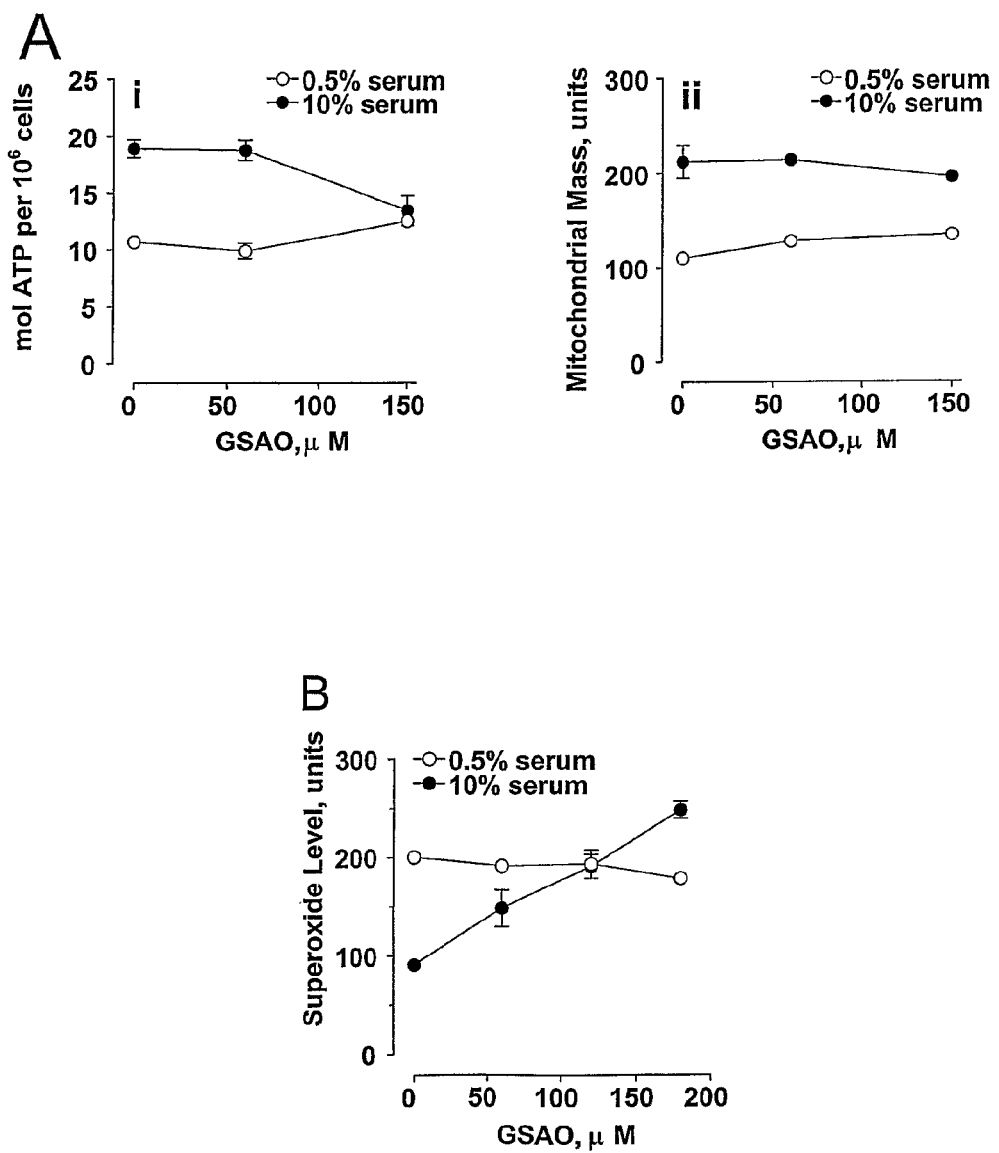
FIG. 4. GSAO inhibited ATP production and increased superoxide levels in proliferating, but not growth-quiescent, endothelial cells. A. BAE cells were cultured for 24 hr in medium containing 0.5% or 10% serum and then for a further 24 hr in the presence of GSAO. In part i, cellular ATP levels were measured using a luciferin/luciferase assay. Results are mean±SEM of four experiments. In part ii, mitochondrial mass was measured from uptake of nonyl acridine orange (NAO). Results are mean±range of two experiments. B. Superoxide level, measured with dihydroethidine, in BAE cells that had been cultured for 24 hr in medium containing 0.5% or 10% serum and then for a further 24 hr in the presence of GSAO. Results are mean±range of two experiments. C. Simultaneous measurement of $O_2^-$ (y axis) in BAE cells cultured in medium containing 10% serum and GSAO for 24 hr. Percentage of cells in each quadrant is shown in the outermost corner.

The binding of GSAO to ANT in proliferating endothelial cells affected ATP production. The ATP content of proliferating BAE cells was approximately twice that of growth-quiescent cells and incubation with 150 µM GSAO for 24 h reduced ATP levels in proliferating cells to that of growth-quiescent cells (FIG. 4ai). This result mirrors the selective effects of GSAO on proliferating cell viability (FIG. 4ai). To confirm that the decreased cellular ATP was due to an effect of GSAO on mitochondrial ATP synthesis rather than mitochondrial biogenesis, mitochondrial mass was measured using nonyl acridine orange. This dye binds to cardiolipin in the mitochondrial membrane (Petit et al., 1992). The mitochondrial mass of proliferating cells was approximately twice that of growth-quiescent cells, which was unchanged by GSAO treatment (FIG. 4aii).

Figure 4C:
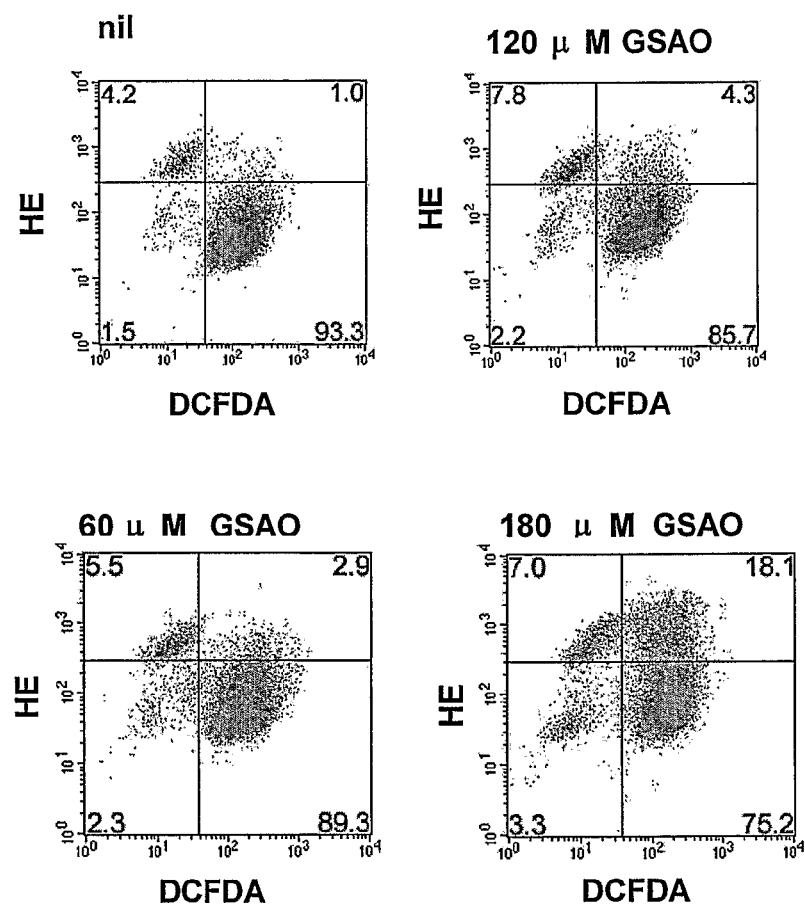

At high concentrations, reactive oxygen species such as superoxide anion ($O_2^-$) can arrest cellular proliferation and induce apoptosis. To test the effect of GSAO on cellular levels of $O_2^-$, BAE cells were treated for 24 h with GSAO and the cellular levels of $O_2^-$ and $H_2O_2$ were measured using the dyes dihydroethidium and CM-$H_2$-DCFDA, respectively. Cellular levels of $O_2^-$ increased linearly with GSAO concentration in proliferating, but not growth-quiescent, BAE cells (FIG. 4b). This effect of GSAO was not due to inhibition of SOD activity as there was only a small decline in $H_2O_2$ levels (FIG. 4c). For instance, treatment with 120 µM GSAO for 24 h resulted in a 30% decrease in $H_2O_2$, but a 100% increase in the level of $O_2^-$. This finding was confirmed using two-channel flow cytometric analysis of cellular $O_2^-$ and $H_2O_2$ levels. $O_2^-$ levels were increased in the majority of cells without a corresponding decrease in $H_2O_2$ (data not shown). In contrast, GSAA had no effect on $O_2^-$ or $H_2O_2$ levels. The linear increase in $O_2^-$ levels with GSAO treatment is consistent with a disruption of mitochondrial integrity.

Example 5

GSAO Triggers Release of Cytochrome C from Mitochondria

To distinguish between the anti-proliferative and pro-apoptotic effects of GSAO, treated cells were stained with propidium iodide (PI) to detect late-apoptotic or dead cells. The total number of cells and the proportion of cells that were PI-positive following 48 h treatment with GSAO were measured by flow cytometry.

Figures 5A, 5B, 5C, 5D:
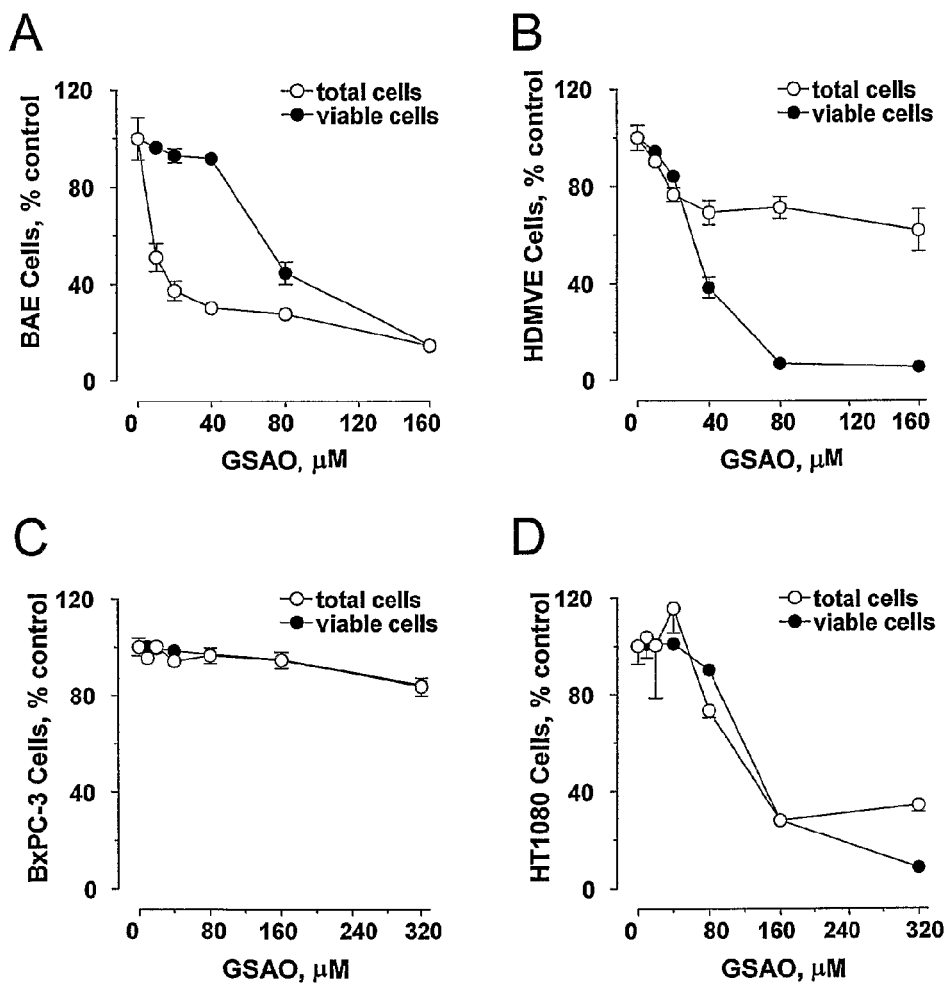
FIG. 5. GSAO was selectively toxic towards endothelial cells compared to tumour cells. Effect of GSAO on cell proliferation and viability for two types of primary endothelial cell (A and B) and five tumour cell lines (C-G). Four human (BxPC-3 pancreatic, HT1080 fibrosarcoma, A549 lung, and HL60 erythroid leukaemia) and one murine (LLC lung) carcinoma cell lines were tested. Results are mean±SEM of three treatments.

The $IC_{50}$ for proliferation arrest of BAE (FIG. 5a) or primary human dermal microvascular endothelial (FIG. 5b) cells was ~10 µM and ~15 µM, respectively. The $IC_{50}$ for loss of viability was ~75 µM and ~35 µM, respectively, indicating that GSAO arrested proliferation at lower concentrations than were necessary to induce apoptosis. The $IC_{50}$ for proliferation arrest of bovine vascular smooth muscle cells was ~30 µM. In contrast, all tumor cells tested were more resistant to GSAO (FIGS. 5c-g). The concentrations of GSAO that induce proliferation arrest and loss of viability are 3 to >32-fold and 2 to 9-fold higher, respectively, for tumor cells than for endothelial cells (Table 1). GSAO treatment caused Lewis lung carcinoma cells to disaggregate, which was the reason for the apparent increase in cell number for this tumor line (FIG. 5e).

TABLE 1

Effect of GSAO on proliferation and viability of endothelial and tumor cells.

| Cell Type | Proliferation Arrest $IC_{50}$, µM | Loss of Viability $IC_{50}$, µM |
| --- | --- | --- |
| BAE (bovine aortic endothelial) | 10 | 75 |
| HDMVE (human dermal endothelial) | 15 | 35 |
| BxPC-3 (human pancreatic carcinoma) | >320 | >320 |
| HT1080 (human fibrosarcoma) | 95 | 130 |
| LLC (murine lung carcinoma) | $ND^1$ | 140 |
| A549 (human lung carcinoma) | 80 | 150 |
| HL60 (human erythroid leukaemia) | 50 | 140 |

[1]Not determined. LLC cells aggregate in culture and GSAO treatment caused the cells to disaggregate, which compromised the estimation of total cell number.

Example 6

GSAO Triggers Release of Cytochrome C from Mitochondria

Methods

Rat liver mitochondria were suspended at 1 mg of protein per mL at 25° C. in 3 mM HEPES, pH 7.0 buffer containing 75 mM mannitol, 250 mM sucrose, 10 mM sodium succinate, and 2 µM rotenone and treated with the ANT-binding compounds for 0 to 60 min. Reagent concentrations are indicated in the figure legends. Mitochondria in 0.25 mL of reaction were pelleted by centrifugation at 8000 g for 5 min and the supernatants were concentrated 10-fold by ultrafiltration through a Microcon YM-3 membrane (Millipore, Bedford, Mass.). The concentrated supernatants were resolved on 8-16% gradient iGels from Gradipore (Sydney, Australia) under non-reducing conditions and transferred to PVDF membrane. Proteins were detected by Western blot using anti-human cytochrome c polyclonal antibodies (Product 556433, BD Pharmingen) and anti-rabbit peroxidase-conjugated antibodies (Dako, Carpinteria, Calif.). Chemiluminescence films were analyzed using a GS-700 Imaging Densitometer and Multi-Analyst software (Bio-Rad, Hercules, Calif.).

Results

Figure 6:
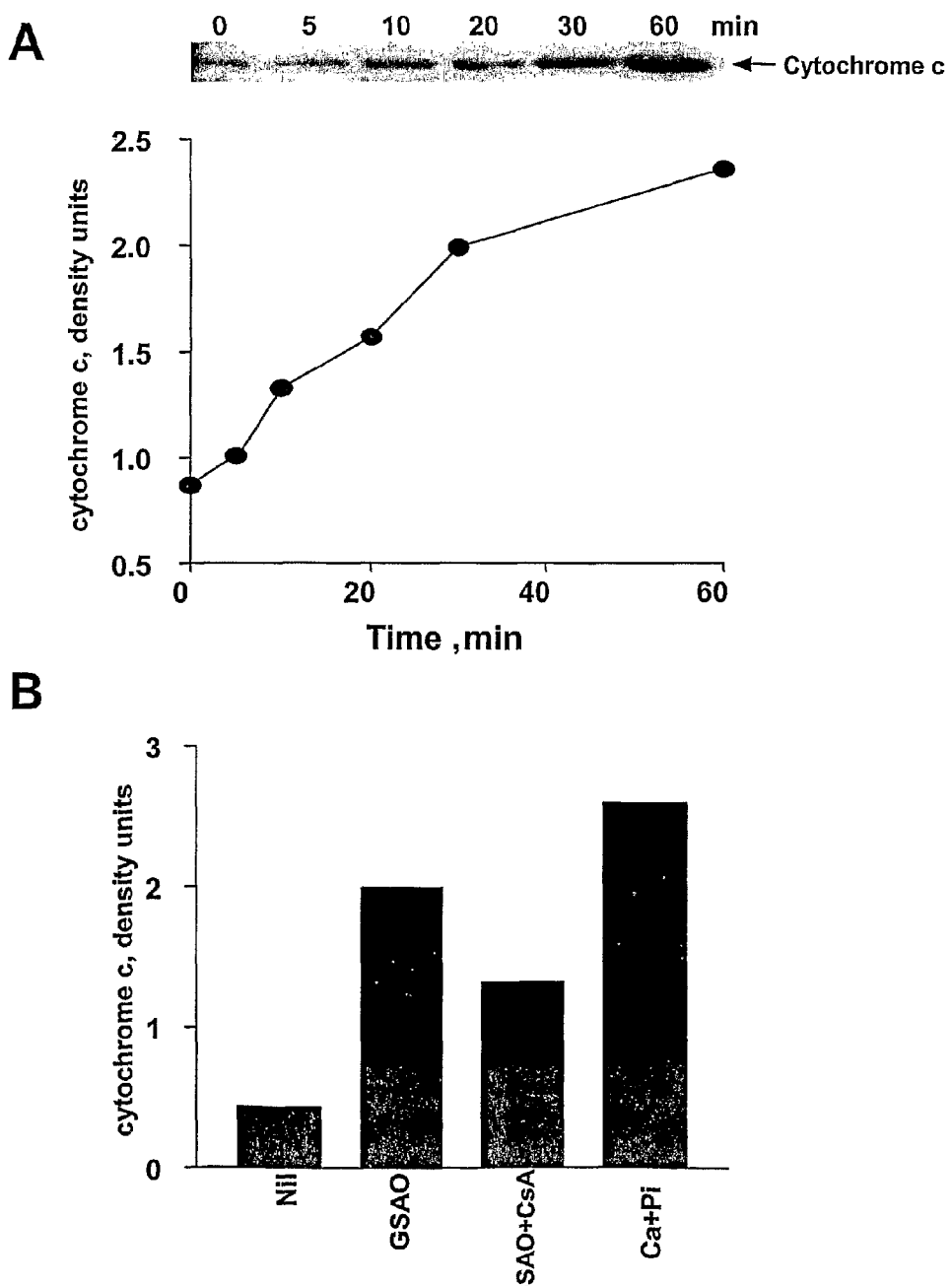
FIG. 6. GSAO induced cytochrome c release from mitochondria. A Rat liver mitochondria were incubated for 0-60 min with 100 μM GSAO and the cytochrome c released into the medium was measured by Western blot. The Western blot and corresponding quantification is shown. B Rat liver mitochondria were incubated for 30 min with nil, 100 μM GSAO, 100 μM GSAO and 5 μM cyclosporin A (CsA), or 150 μM $Ca^{2+}$ and 6 mM Pi as a positive control. The cytochrome c released into the medium was measured by Western blot.

Incubation of isolated mitochondria with GSAO triggered time-dependent release of Cytochrome C into the medium (FIG. 6A). The ANT ligand, cyclosporin A, partially inhibited this release (FIG. 6B).

Example 7

GSAO Inhibited Angiogenesis in the Chick Chorioallantoic Membrane (CAM)

Methods

Fertilised 3 day-old white Leghorn eggs (Spafas, Norwich, Conn.) were cracked, the embryos with intact yolks placed in 20×100 mm petri dishes and incubated for 3 days at 37° C. and 3% $CO_2$ (Folkman, 1985). Methylcellulose (Fisher Scientific, Fair Lawn, N.J.) discs containing 5, 10 or 50 µg of either GSAA or GSAO were then applied to the CAM of individual embryos and incubated for 48 h at 37° C. and 3% $CO_2$. The discs were made by desiccation of GSAA or GSAO in 10 µl of 0.45% methylcellulose on teflon rods. The CAMs were observed using a stereomicroscope and scored for no obvious affect or inhibition of CAM angiogenesis as defined by avascular zones. On some occasions CAM blood vessels were injected with India ink and photographed.

Results

In view of the ability of GSAO to selectively kill proliferating, but not growth-quiescent, endothelial cells in vitro, GSAO was tested to determine whether it was an effective inhibitor of angiogenesis in vivo.

Figure 7A:
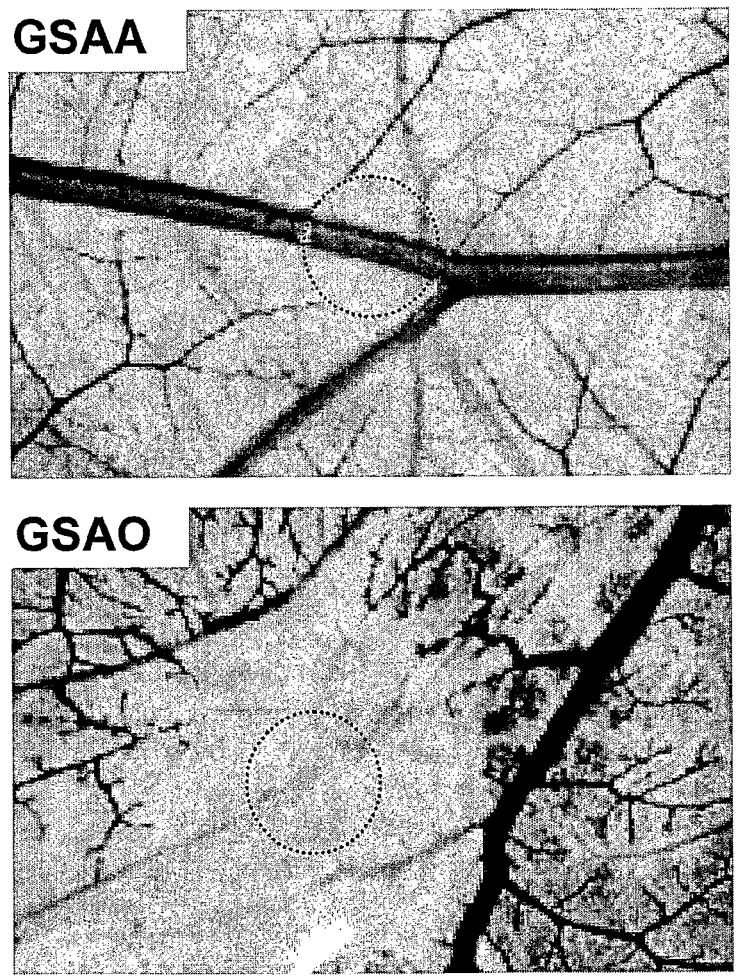
FIG. 7. GSAO inhibited CAM angiogenesis and tumour angiogenesis and tumour growth in mice. A Photographs of CAM's after incubation with methylcellulose discs containing 10 μg of either GSAA (top) or GSAO (bottom) for 48 h. The dotted circle indicates the placement of the disc. B The number out of 5 zones positive for angiogenesis indicated at 5, 10 or 50 μg of GSAO per pellet. GSAA did not inhibit CAM angiogenesis up to 50 μg per pellet. C-E SCID mice bearing ~0.1 g BxPC-3 (part C) or HT1080 (part D) tumours, or C57B16/J mice bearing ~0.1 g LLC tumours (part E), were randomised into two groups (n=4) and treated S.C. with either GSAA or GSAO at 10 mg/kg/day in 0.2 mL of PBS containing 100 mM glycine. The data points are the mean±SE of the tumour volumes. F Histological sections of the BxPC-3 tumours from the experiment shown in part C at day 31 of treatment with GSAA or GSAO were analysed for angiogenesis (CD31), proliferation (PCNA) and apoptosis (TUNEL).
Figure 7B:
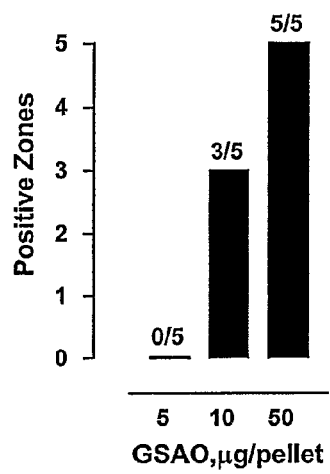

The chick chorioallantoic membrane (CAM) assay has been used for the detection and analysis of angiogenesis inhibition (Nguyen et al., 1994). GSAO inhibited CAM angiogenesis in a concentration-dependent manner (FIG. 7A). Angiogenesis inhibition was defined as avascular zones 48 h after implantation of methylcellulose pellets containing GSAO on the 6-day CAM (FIG. 7Ai). GSAA up to 50 µg per pellet had no affects on CAM angiogenesis.

Example 8

GSAO Inhibited Tumour Angiogenesis and Tumour Growth in Mice

Methods

Primary Tumour Growth Assays

Female 7 to 9 week old SCID or C57Bl6/J mice were used (Massachusetts General Hospital, Boston, Mass.). Mice were held in groups of 3 to 5 at a 12 hour day and night cycle and were given animal chow and water ad libitum. SCID or C57Bl6/J mice were anaesthetised by inhalation of isoflurane, the dorsal skin shaved and cleaned with ethanol, and a suspension of $2.5 \times 10^6$ BxPC-3, HT1080 or LLC cells in 0.2 mL of PBS, or saline for LLC cells, was injected S.C. in the proximal midline. LLC cells were prepared according to O'Reilly et al. (1997). Tumour volume was calculated using the relationship, $a \cdot b^2 \cdot 0.52$, where a is the longest and b the shortest diameter.

Immunohistochemistry

Tumours were fixed in Buffered Formalde-Fresh (Fisher Scientific, Fair Lawn, N.J.), embedded in paraffin and 5 µm thick sections were cut and placed on glass slides. Sections were stained with haematoxylin and eosin or for CD31, PCNA (Holmgren et al., 1995) or fragmented DNA (Gavrielli et al., 1992). Microvessels were counted in 3 tumours, including the smallest and largest, from the control and treatment groups and the density was graded in the most active areas of neovascularisation according to Weidner et al. (1991). The proliferative index was estimated by the percentage of cells scored under 400× magnification. A minimum of 1000 cells was counted in two separate sections. The apoptotic index was estimated by the percentage of cells scored under 400× magnification. A minimum of 1500 cells was counted in two separate sections.

Results

The growth of both human and murine primary tumours in immunocompromised and immunocompetent mice, respectively, was markedly suppressed by systemic administration of GSAO. Treatment of SCID mice bearing BxPC-3 (FIG. 7C) or HT1080 (FIG. 7D) tumours, or C57Bl6/J mice bearing LLC tumours (FIG. 7E), by subcutaneous administration of 10 mg/kg/day GSAO at a site remote from the tumour resulted in >90%, ~70% and ~50% inhibition of the rate of tumour growth, respectively. Administration of control GSAA caused <20% inhibition of the rate of tumour growth in all experiments when compared to administration of vehicle alone (data not shown). There was no apparent adverse affects of administration of either GSAO or GSAA to either SCID or C57Bl6/J mice. The average mice weights of the GSAO and GSAA treatment groups over the course of the experiments were the same, and there was no apparent macroscopic differences and no morphological changes in the heart, lungs, liver, kidneys, and spleen of GSAO or GSAA-treated mice (data not shown).

Figure 7C:
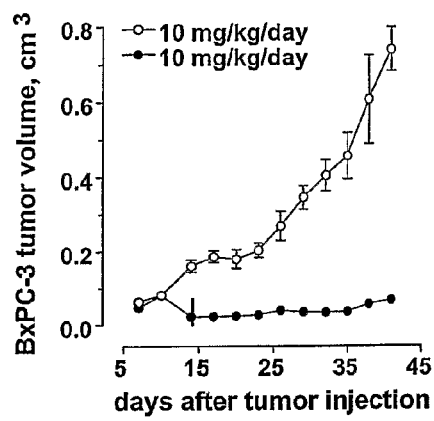
Figure 7D:
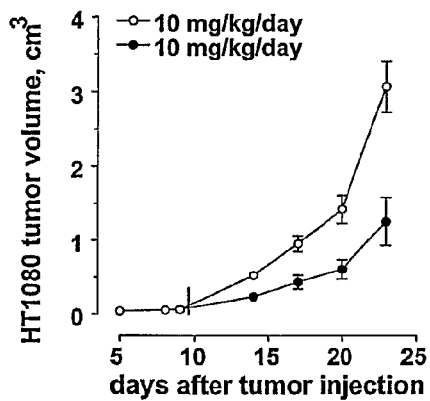
Figure 7E:
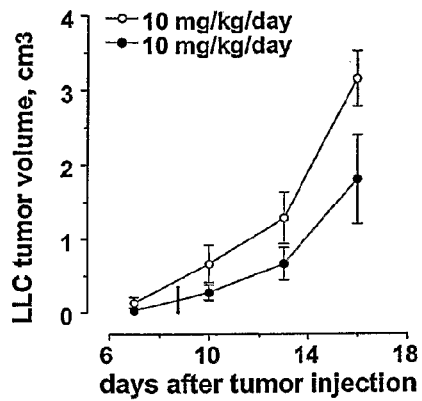
Figure 7F:
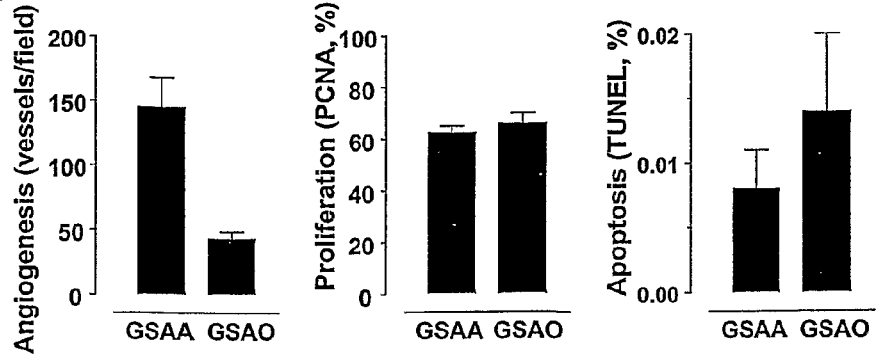

Immunohistochemical analysis of the tumours from the experiment described in FIG. 7C indicated a significant reduction in blood vessel density in the GSAO-treated tumours (p<0.001) (FIG. 7F). The proliferative indices of the GSAA- and GSAO-treated tumours were the same, while there was a significant increase in the apoptotic indices of GSAO- versus GSAA-treated tumours (p=0.05) (FIG. 6F). Inhibition of tumour angiogenesis has been associated with an increase in apoptosis of the tumour cells (O'Reilly et al., 1997). The high rate of apoptosis is thought to balance the high proliferative rate of the tumour cells resulting in no net gain in tumour size (Holmgren et al., 1995).

The effect of GSAO on tumor growth is consistent with inhibition of tumor angiogenesis. GSAO arrested proliferation of endothelial cells in vivo but had no effect on BxPC-3 proliferation at >30-fold higher concentrations (Table 1), and systemic administration of GSAO markedly reduced tumor vascularity in vivo but had no effect on the proliferative index of the BxPC-3 tumor cells (FIG. 7F).

Example 9

Comparison of Antiproliferative Activity of GSAO and Related Analogues on BAE Cells Methods Compounds 1-11, 12-15 and 20-23 were screened during 72 hours in 96 well plates with 1000 cells/well at day 1 in DMEM 10% FBS. At day 2 cells were treated by different concentrations of compounds. The cells growth was determined and compared to untreated cells at day 4 using MTT revelation (reading at 550 nm). The $IC_{50}$ values were determined and the increase of activity in comparison to GSAO was calculated as follows:

Increasing activity factor=$IC_{50}$(GSAO)/$IC_{50}$(GSAO Analogue)

Figure 8:
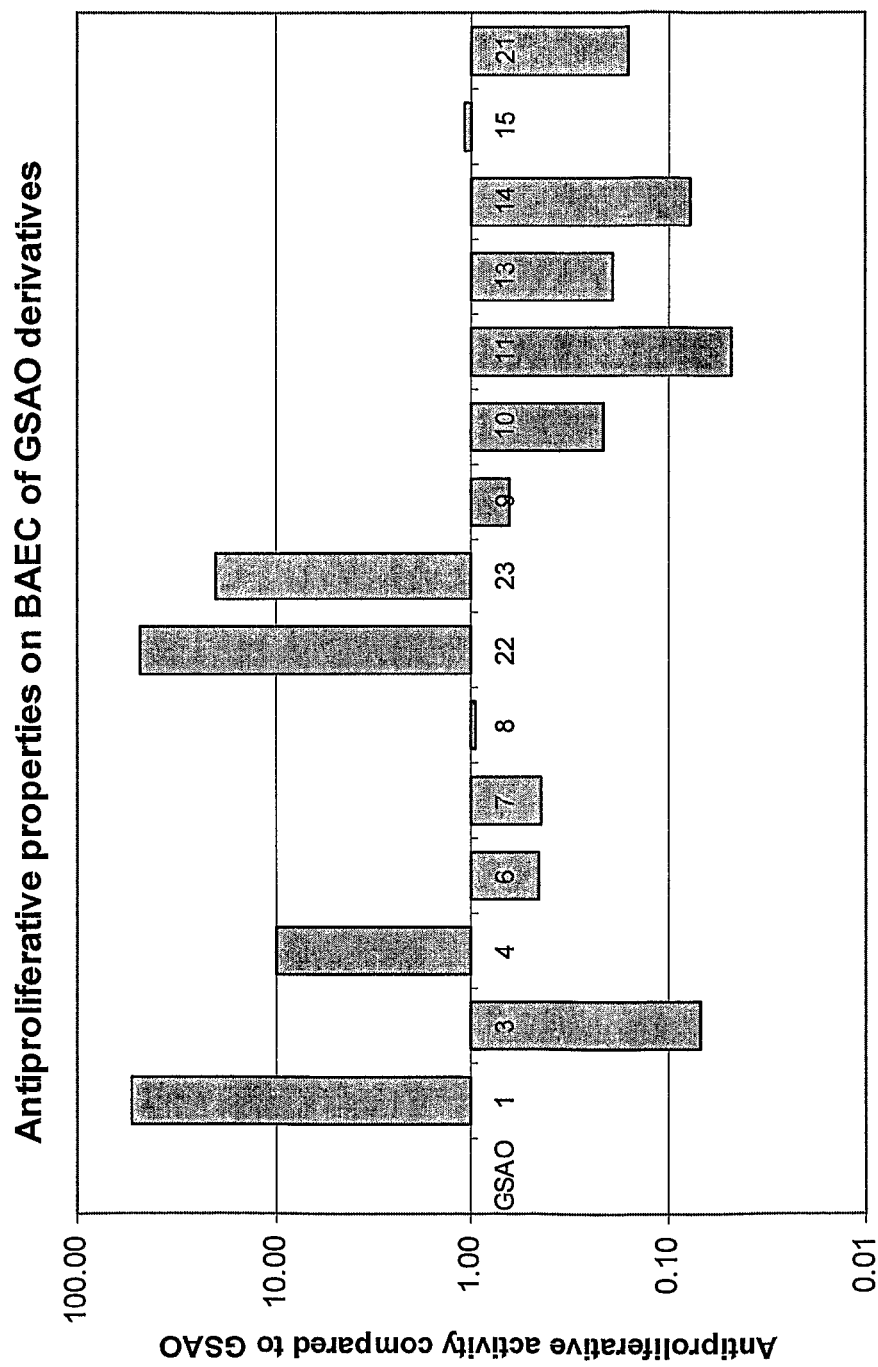
FIG. 8. Antiproliferative activities on BAE cells of compounds 1-11, 13-15 and 20-23 compared to GSAO.

The results are summarised in Table 2 and FIG. 8.

TABLE 2

Activity of GSAO and related analogues on proliferation of BAE cells

| Compound | $IC_{50}$ (µM)* | SD | Fold Increase |
|---|---|---|---|
| GSAO | 8.28 | 2.09 | — |
| 1 | 0.16 | 0.02 | 53.2 |
| 3 | 122 | 7.2 | 0.07 |
| 4 | 0.84 | 0.31 | 9.9 |
| 6 | 18.2 | 3.2 | 0.45 |
| 7 | 19.0 | 5.46 | 0.44 |
| 8 | 8.8 | 1.68 | 0.95 |
| 22 | 0.18 | 0.04 | 46.9 |
| 23 | 0.42 | 0.18 | 19.8 |
| 9 | 12.9 | — | 0.64 |
| 10 | 39.0 | 11.3 | 0.21 |
| 11 | 170 | 3.80 | 0.05 |
| 13 | 43.3 | 10.2 | 0.19 |
| 14 | 106 | 31.2 | 0.08 |
| 15 | 7.6 | 6.41 | 1.1 |
| 21 | 51.3 | 8.27 | 0.16 |

All $IC_{50}$ values are obtained from at least 2 distinct experiments except compound 9 which was measured once.

Results

The results presented in Table 2 suggest compounds where the arsenoxide group is in an ortho position (relative to the position of the linker group on the phenylene ring) are significantly more active than the analoguous compounds where the arsenoxide group is in a para position. For example, compound 1 ("o-GSAO") is 53.2 times more active than GSAO. Similarly, the "ortho-arsenoxide" compound 4 is approximately 140 times more active than the corresponding p-arsenoxide analogue (compound 3); compound 22 is approximately 106 times more active than the corresponding p-arsenoxide compound 7; and compound 23 is approximately 20 times more active than the corresponding p-arsenoxide compound 8. These results were entirely unexpected as it was believed that positioning the arsenical moiety at the ortho position would sterically hinder interaction of the arsenic residue with dithiols.

Figure 9:
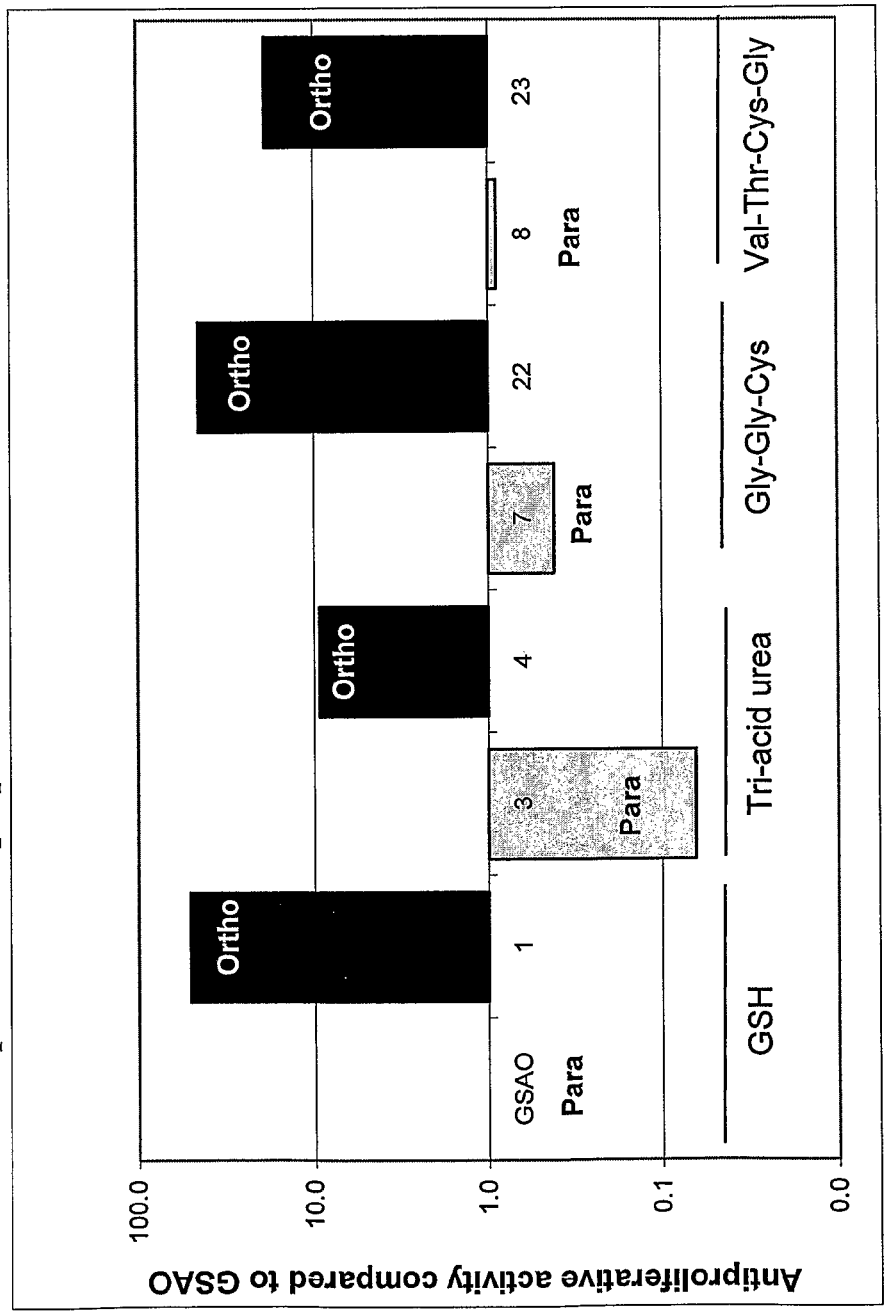
FIG. 9. Comparison of antiproliferative activity on BAE cells of compounds having an arsenoxide group in an ortho or para position of a phenylene ring.

A comparison of the antiproliferative effect on BAE cells of o-arsenoxide and p-arsenoxide compounds is presented in FIG. 9.

Figure 10:
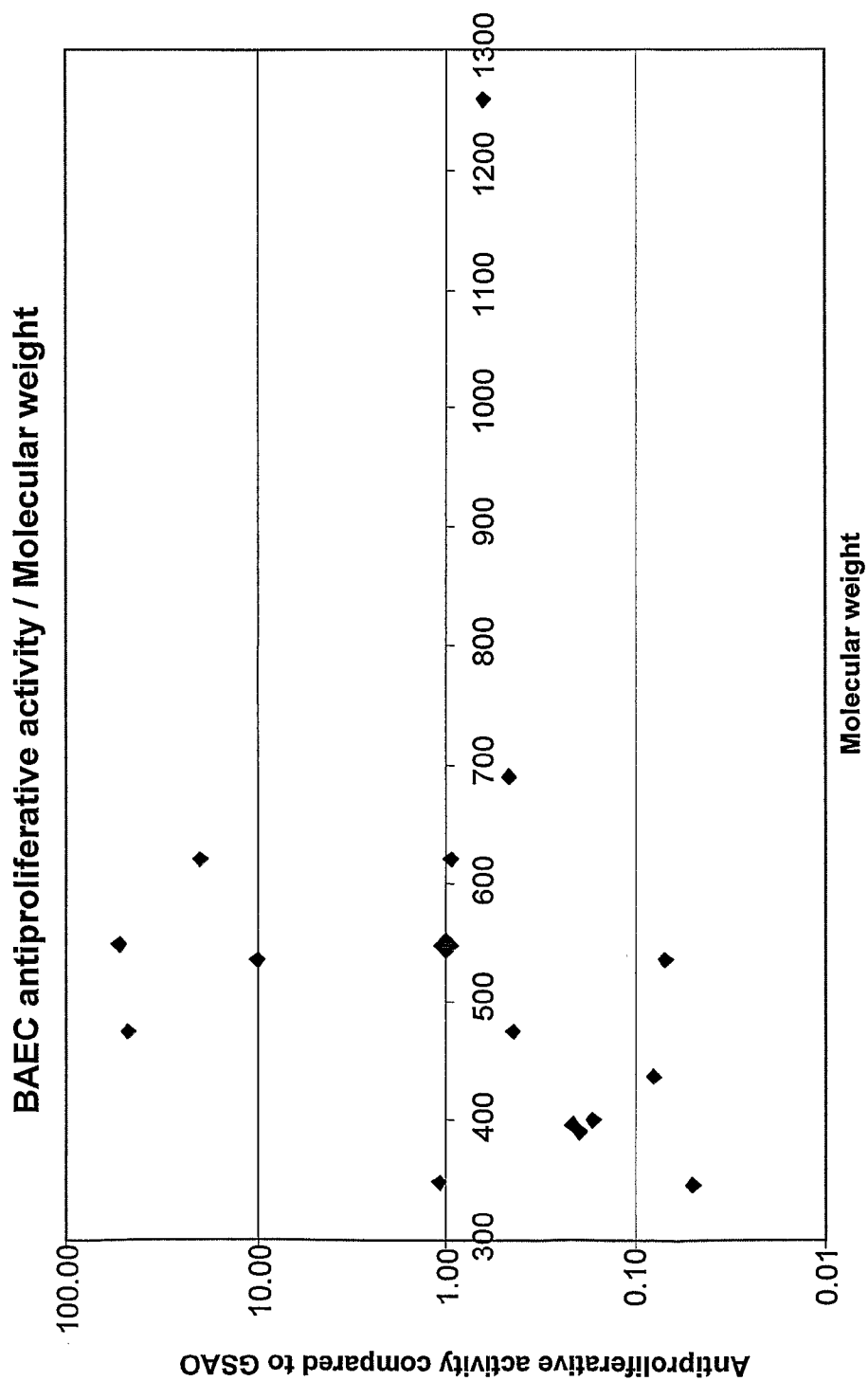
FIG. 10. Correlation of activity on BAE cells and molecular weight for GSAO and related analogues.

A comparison of antiproliferative effect on BAE cells versus molecular weight of the compounds is presented in FIG. 10.

Figure 11:
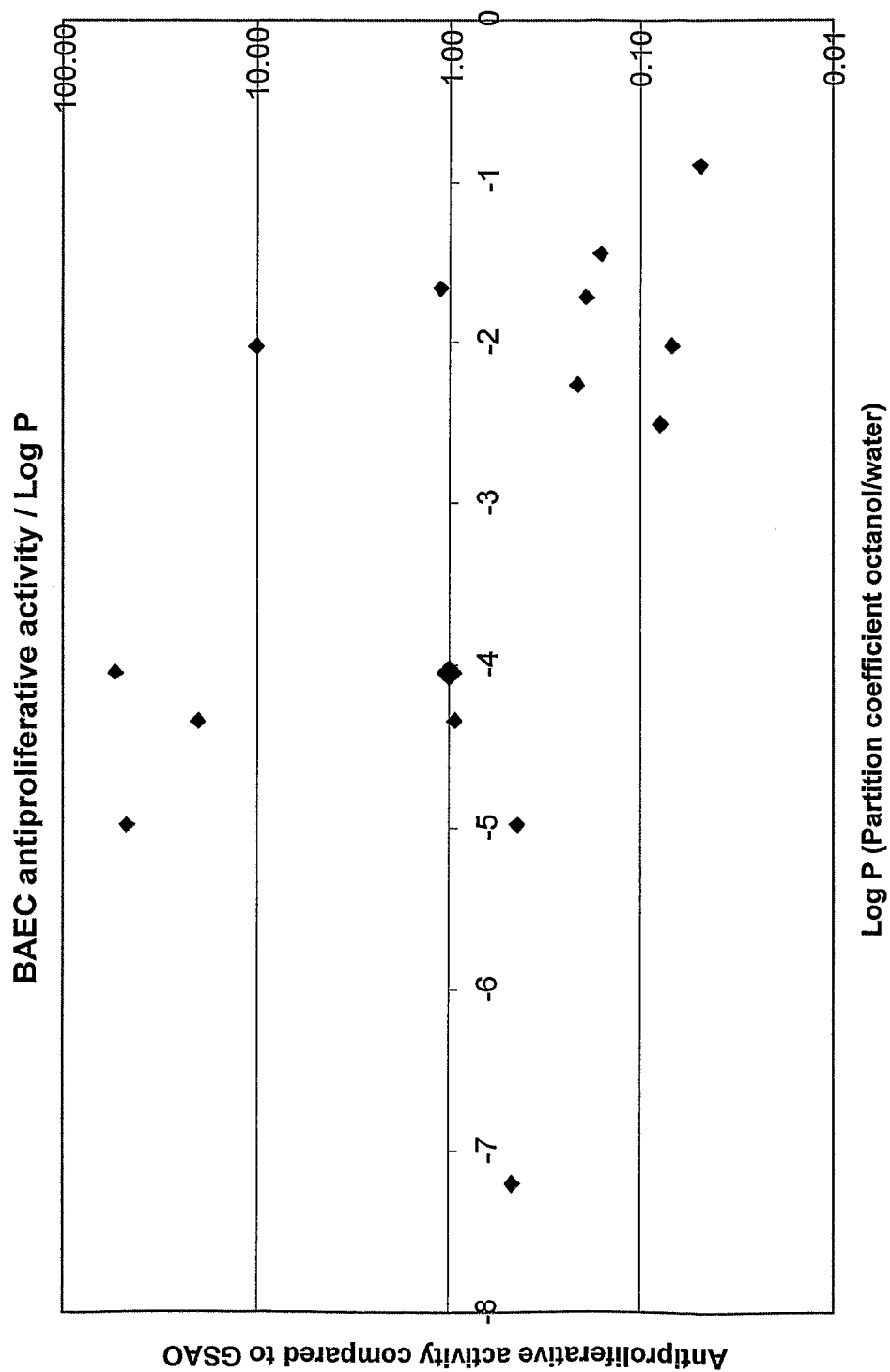
FIG. 11. Correlation of activity on BAE cells and Log P weight for GSAO and related analogues.

A comparison of antiproliferative effect on BAE cells versus Log P values of the compounds is presented in FIG. 11.

Example 10

Effect of GSAO and Related Analogues on Induction of the Mitochondrial Pore Transition Methods The screening was performed using rat liver mitochondria frozen for 1 or 2 days at −80° C. after isolation. The mitochondria swelling was measured by monitoring the decrease in light scattering at 520 nm using a microplate reader.

Figure 12:
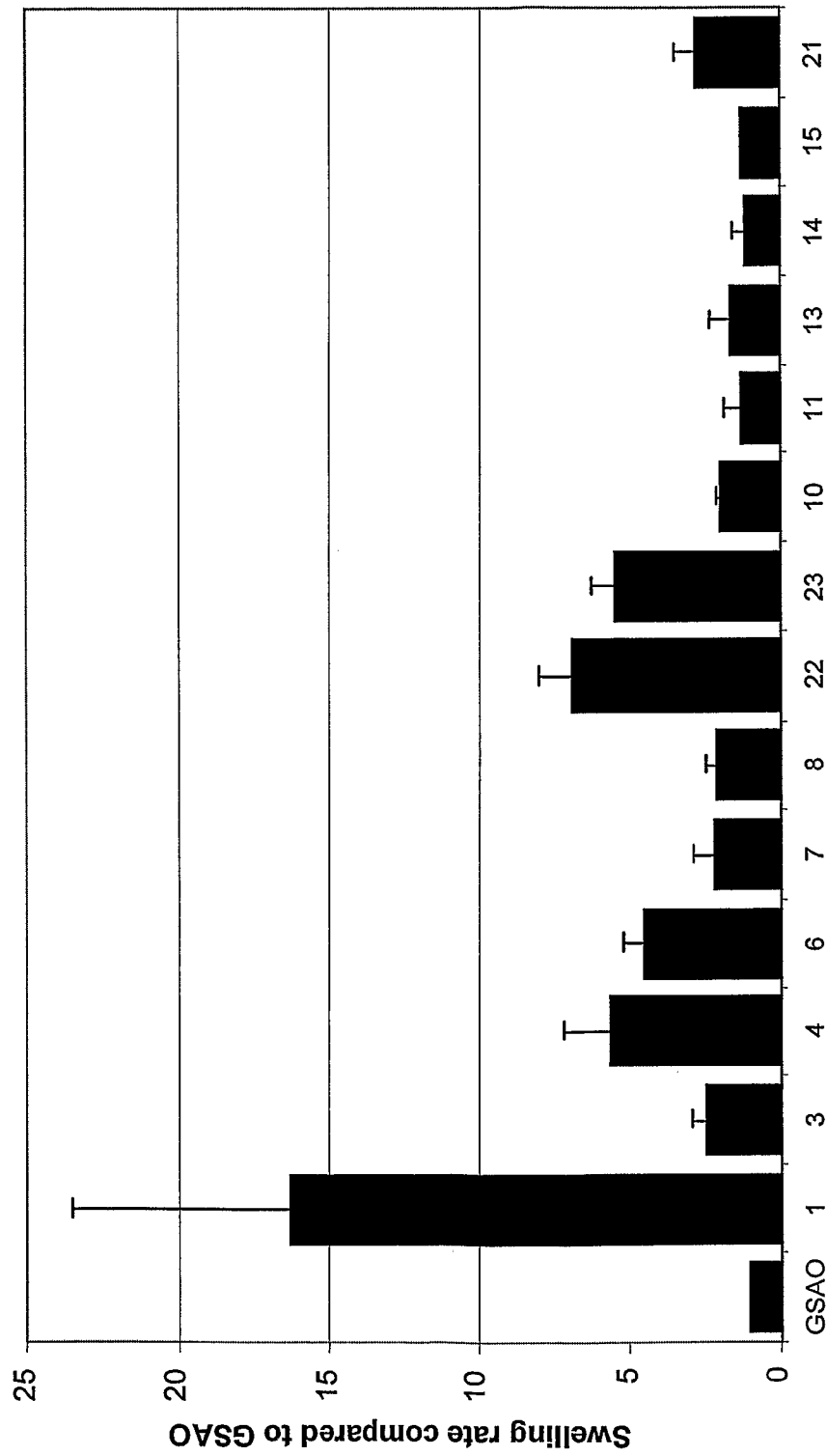
FIG. 12. Comparison of Induction of MPTP by GSAO analogues and GSAO.

In all experiments the time needed for half maximal swelling was determined for each compound. Then, the swelling rates were calculated and compared with GSAO. The increase of swelling rate as compared to GSAO was calculated as follows:

Increasing swelling factor=Swelling Rate$_{(GSAO\ Analogue)}$/Swelling Rate$_{(GSAO)}$ The results are summarised in Table 3 and presented in FIG. 12.

TABLE 3

Effect of GSAO and related analogues on MPTP induction

| Compound | MPTP Swelling Rate Increase/GSAO* | |
|---|---|---|
| | Mean | SD |
| GSAO | 1 | 0 |
| 1 | 16.3 | 7.2 |
| 3 | 2.4 | 0.5 |
| 4 | 5.6 | 1.5 |
| 6 | 4.5 | 0.8 |
| 7 | 2.2 | 0.6 |
| 8 | 2.1 | 0.4 |
| 22 | 6.9 | 1.1 |
| 23 | 5.4 | 0.7 |
| 10 | 2.0 | 0.2 |
| 11 | 1.3 | 0.4 |
| 13 | 1.6 | 0.7 |
| 14 | 1.1 | 0.4 |
| 15 | 1.3 | — |
| 21 | 2.8 | 0.7 |

All compounds were tested at least 2 times on different mitochondrial preparations for their MPTP induction properties, except compound 15 which was tested only once.

Results

All compounds tested showed similar or better induction activity than GSAO. The most active compounds were 1, 4, 22 and 23 which showed an increased activity relative to GSAO ranging from 5.4 to 16.3 fold (Table 3; FIG. 12). For the MPTP induction, as for antiproliferative activity on BAE cells, ortho-arsenoxide compounds (1, 4, 22 and 23) had increased activity relative to the corresponding para-arsenoxide compounds (GSAO, 3, 7 and 8, respectively).

Figure 13:
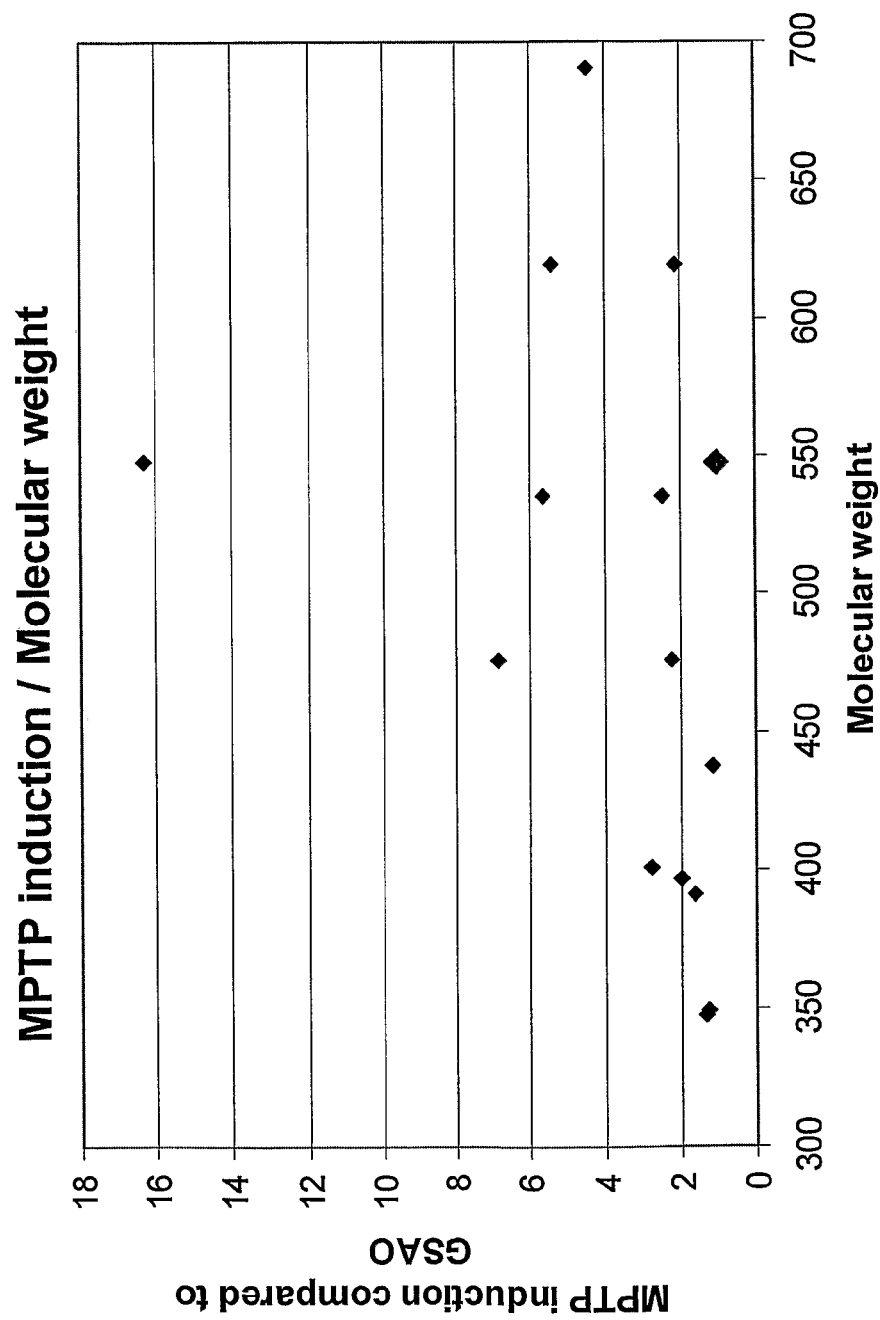
FIG. 13. Correlation of MPTP induction and molecular weight for GSAO and related analogues.

A comparison of MPTP induction versus molecular weight of the compounds is presented in FIG. 13.

Figure 14:
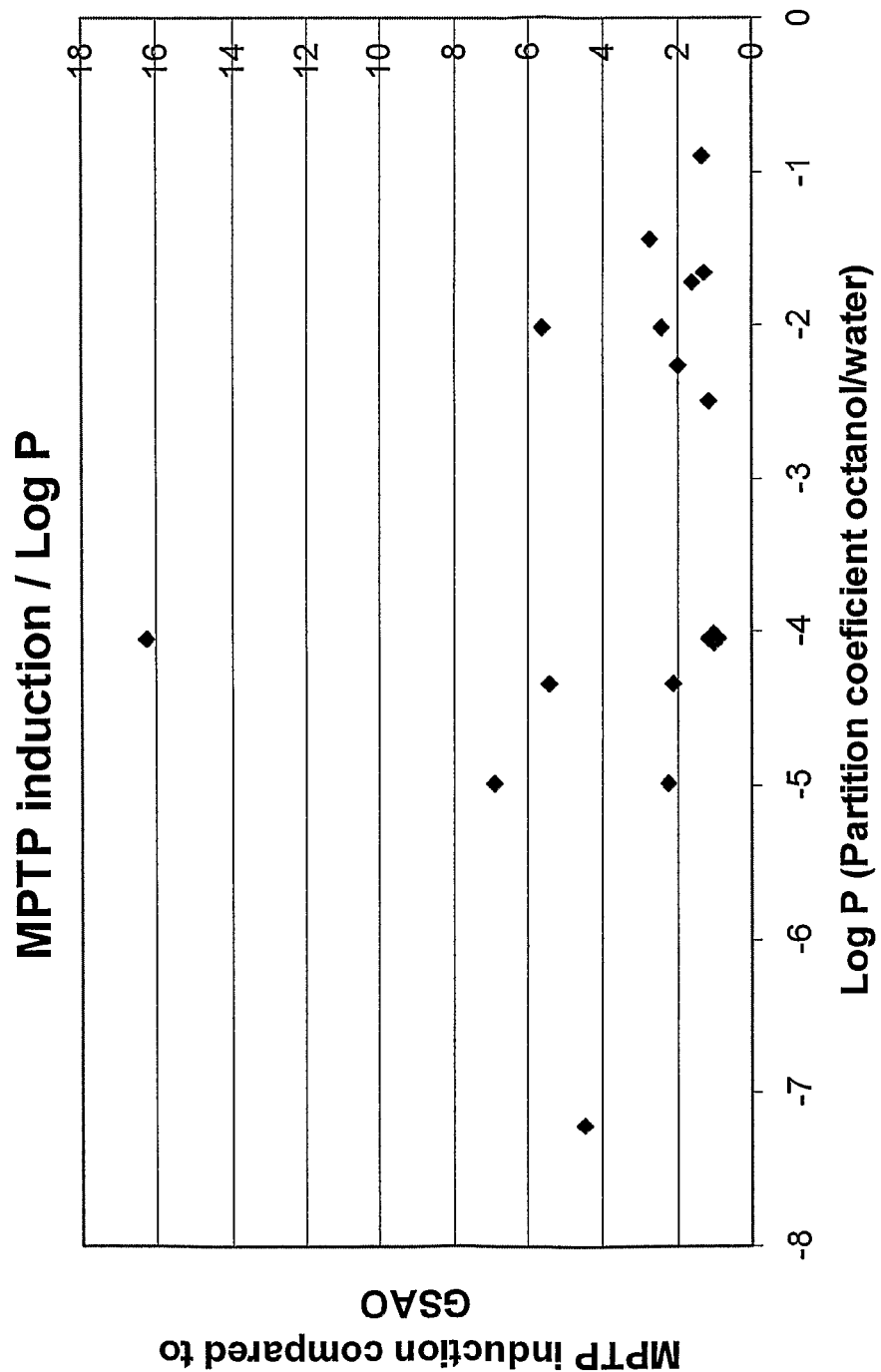
FIG. 14. Correlation of MPTP induction and Log P for GSAO and related analogues.

A comparison of MPTP induction versus Log P of the compound tested is presented in FIG. 14.

Figure 15:
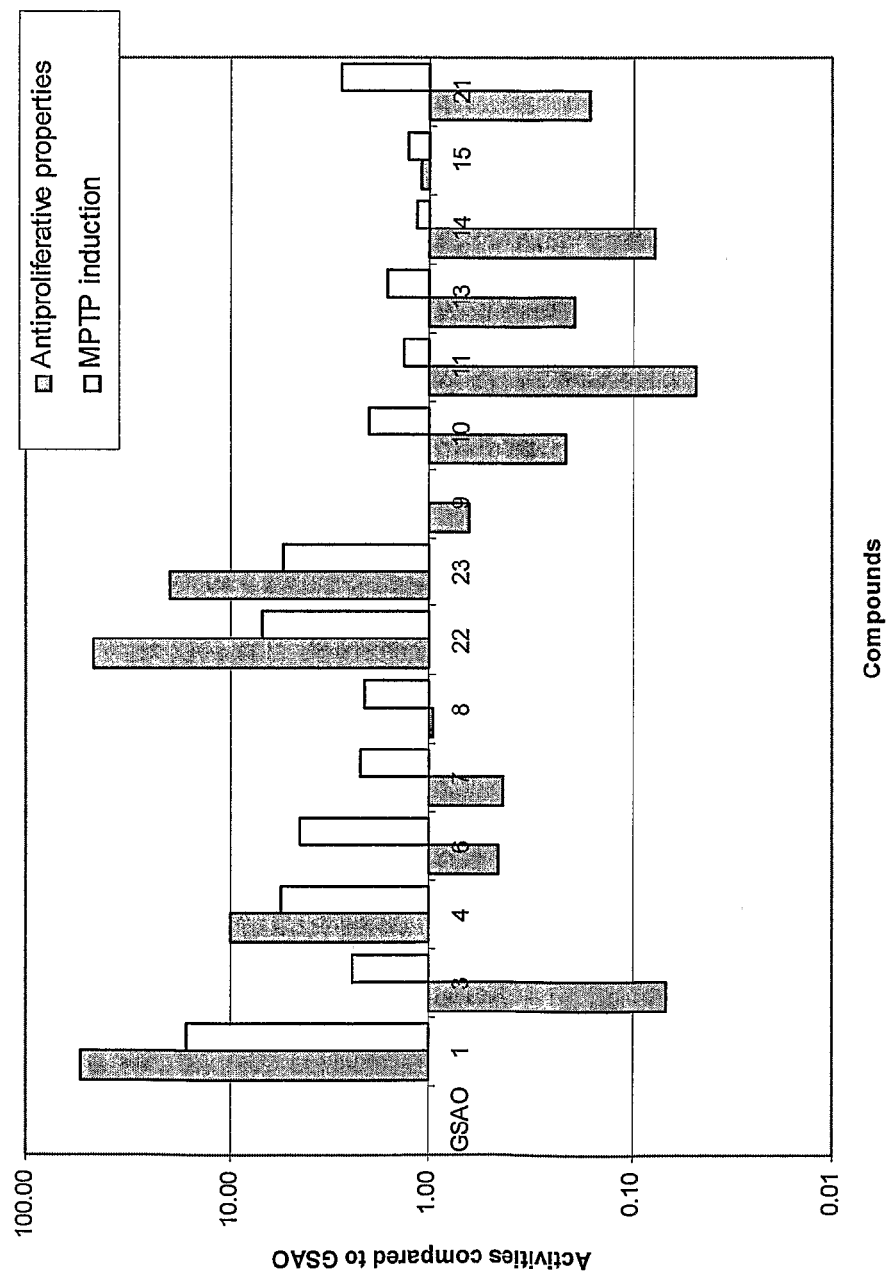
FIG. 15. Comparison of antiproliferative activity on BAE cells and MPTP induction.

The antiproliferative activity of GSAO and related analogues was compared to the ability of those compounds to induce the MPT. The results are presented in FIG. 15. Compounds which showed increased activity relative to GSAO in both tests were the ortho-arsenoxide compounds 1, 4, 22 and 23.

Example 10

Comparison of Affinity for Thiols of Ortho- and Para-Substituted Arsenoxide Compounds In order to determine if the ortho- or para-position of the arsenoxide moiety on the phenylene ring significantly influenced the compounds ability to bind dithiols, GSAO (pare-arsenoxide) and compound 1 (ortho-arsenoxide) were titrated with DTT.

Figure 16:
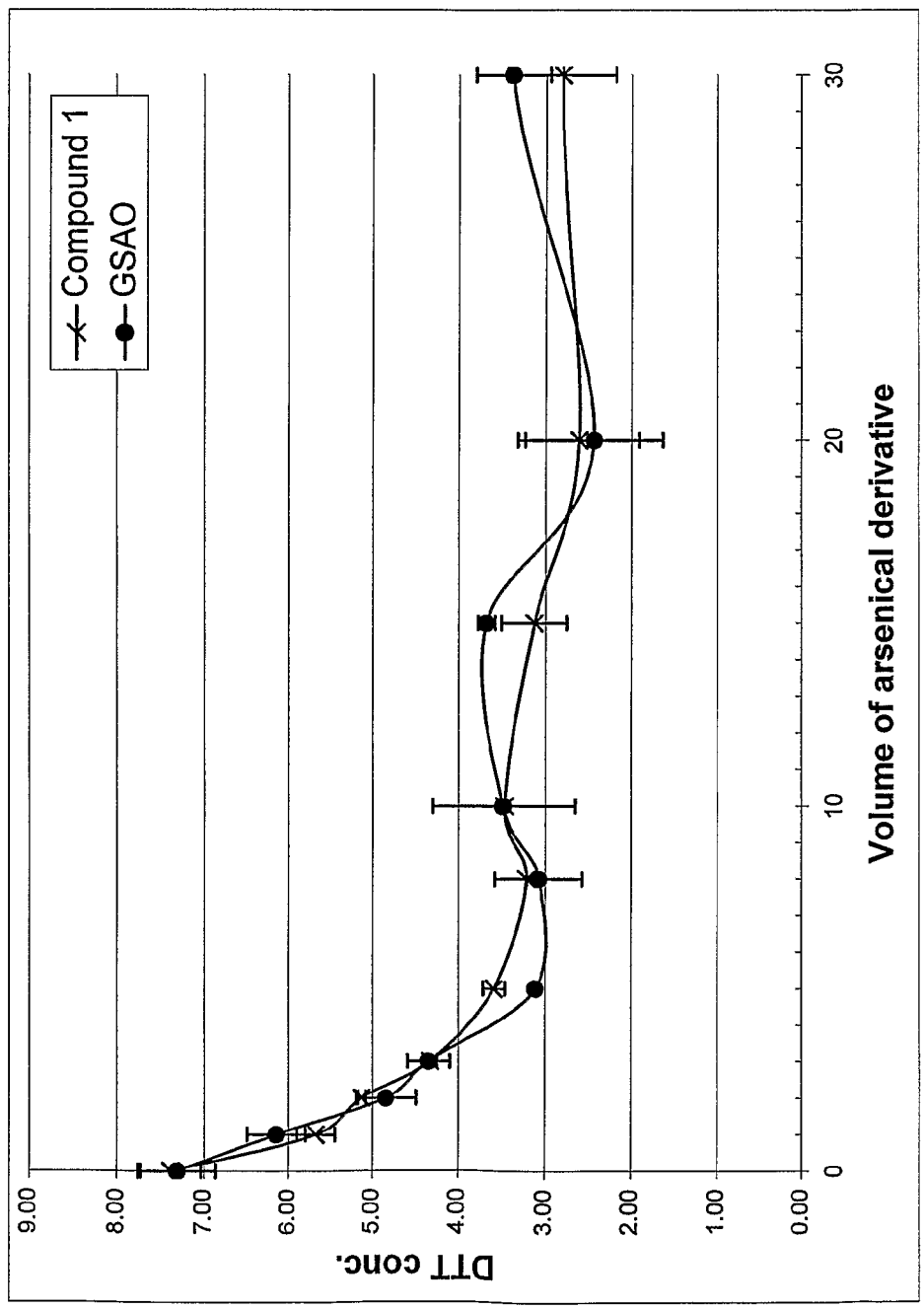
FIG. 16. Comparison of interaction of GSAO and compound 1 with DTT.

As shown in FIG. 16, there was no significant difference in arsenical reactivity for GSAO and Compound 1.

Example 11

Comparison of GSAO and o-GSAO

Mitochondrial Swelling Assay

Method

Mitochondria were isolated from the livers of ~250 g male Wistar rats using differential centrifugation as described previously (Don et al., 2003). The final mitochondrial pellet was resuspended in 3 mM HEPES-KOH, pH 7.0 buffer containing 213 mM mannitol, 71 mM sucrose and 10 mM sodium succinate at a concentration of 30 mg of protein per mL. Mitochondrial permeability transition induction was assessed spectrophotometrically by suspending the liver mitochondria at 0.5 mg of protein per mL at 25° C. in 3 mM HEPES-KOH, pH 7.0 buffer containing 75 mM mannitol, 250 mM sucrose, 10 mM sodium succinate, and 2 mM rotenone. Swelling was measured by monitoring the associated decrease in light scattering at 520 nm using a microplate reader.

Results

Figures 17A, 17B, 17C, 17D:
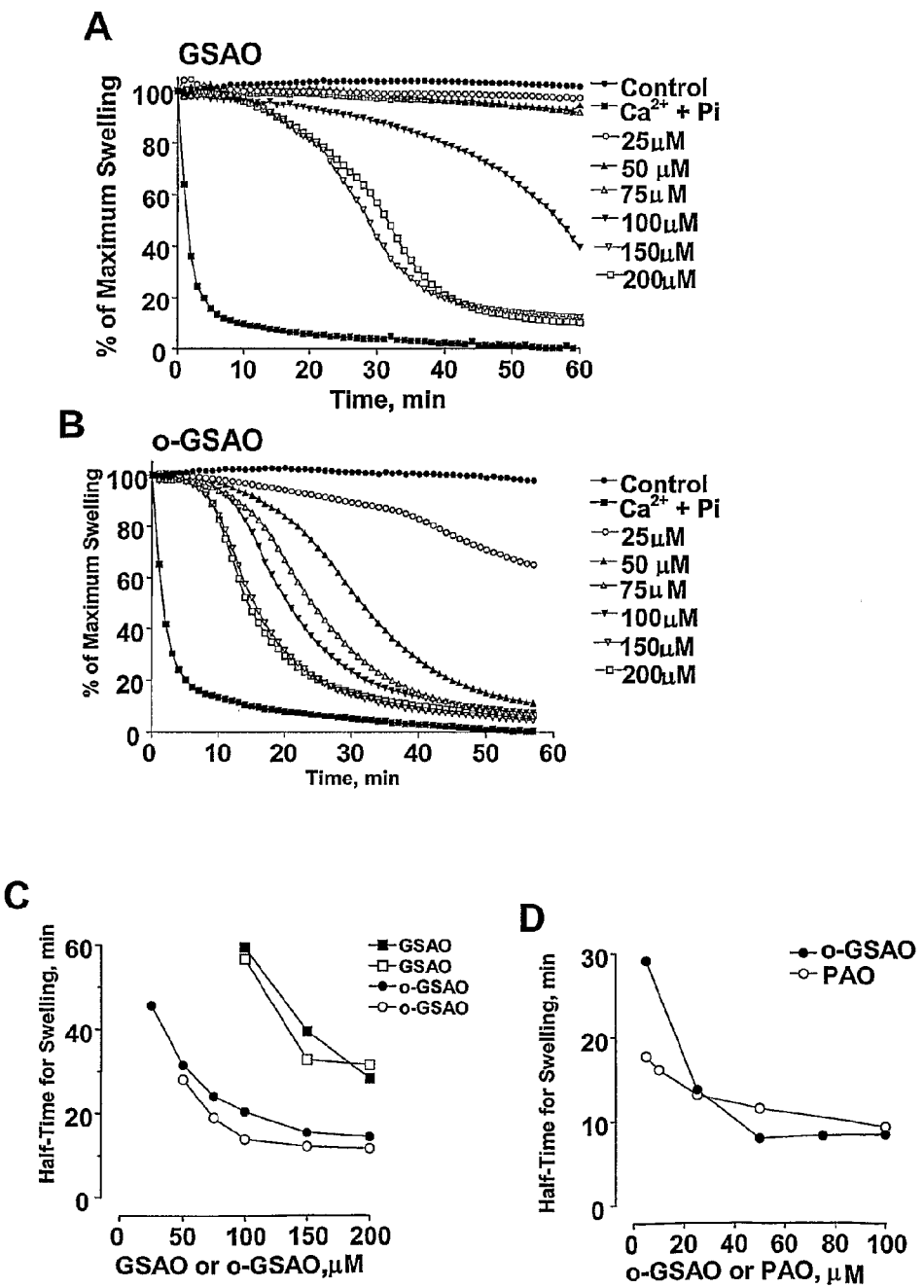
FIG. 17. Induction of the mitochondrial permeability transition by GSAO or o-GSAO. Swelling was measured by decrease in light scattering at 520 nm. Isolated mitochondria were incubated with different concentrations of GSAO (part A) or o-GSAO (part B). The half-time for swelling as a function of GSAO or o-GSAO concentration in two different experiments is shown in part C. The half-time for swelling as a function of GSAO or PAO concentration is shown in part D. The positive control in parts A and B was 150 μM $Ca^{2+}$ and 6 mM Pi (■).

The half-time for maximal swelling of isolated mitochondria was 3-5 times faster for a given concentration of o-GSAO compared to GSAO (FIG. 17). Indeed, o-GSAO was almost as efficient as the lipophilic PAO at inducing the mitochondrial permeability transition (FIG. 17D).

Figures 18A, 18B:
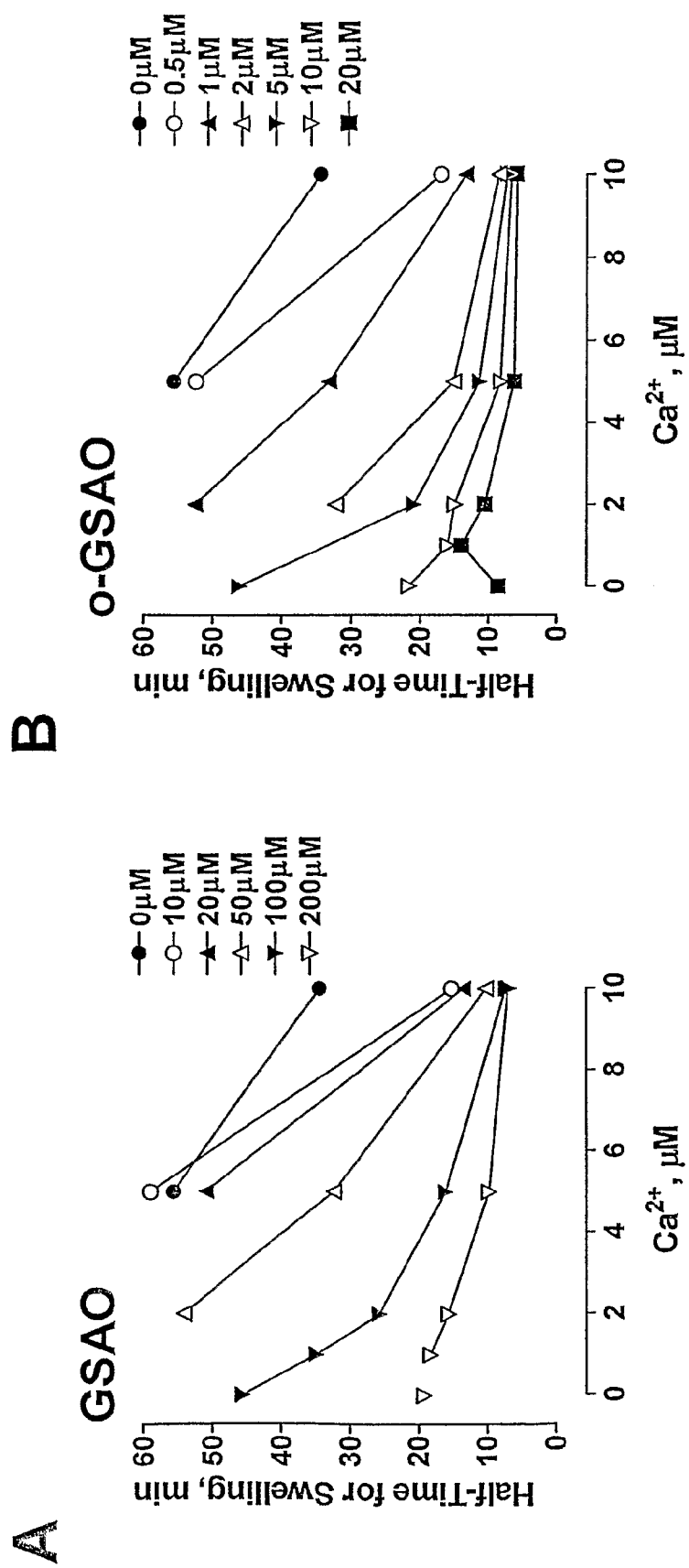
FIG. 18. Calcium dependence of the effect of GSAO or o-GSAO on the mitochondrial permeability transition. Mitochondria were incubated with different concentrations of GSAO (part A) or o-GSAO (part B) at increasing $Ca^{2+}$ concentrations and the time for half-maximal swelling was measured.
Figure 19:
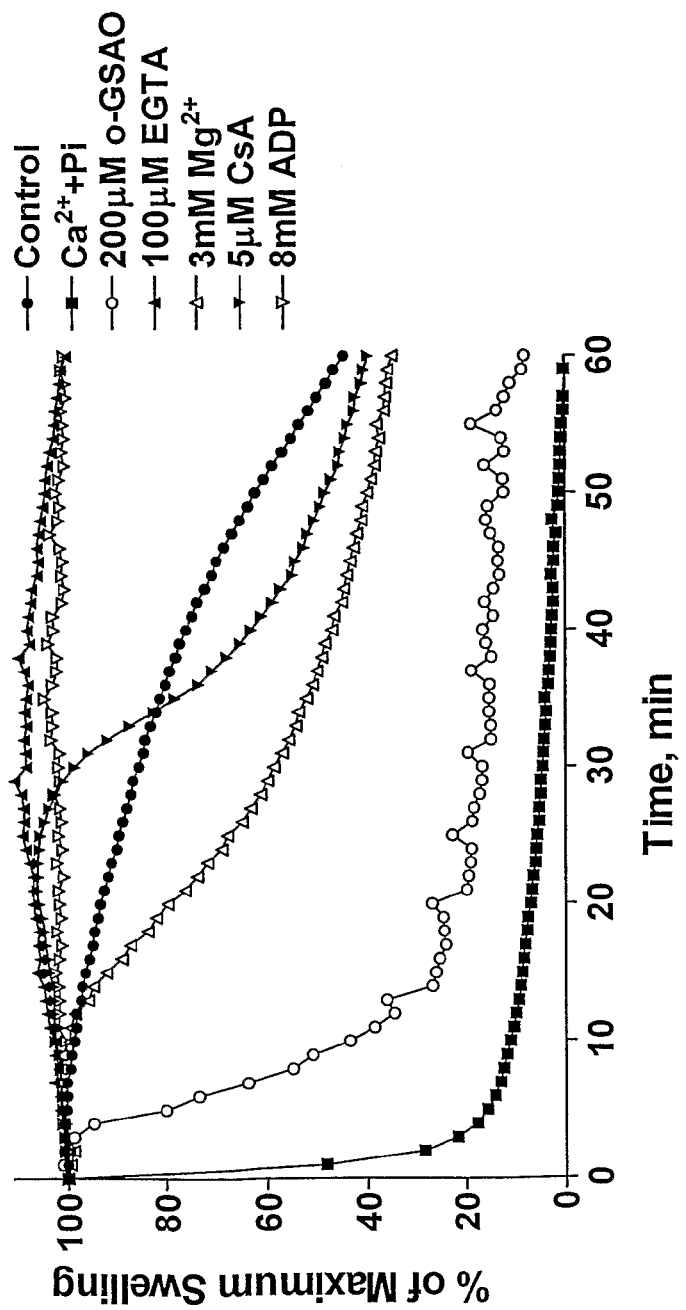
FIG. 19. ANT ligands block induction of the mitochondrial permeability transition by o-GSAO. Mitochondria were incubated with 200 μM o-GSAO in the absence or presence of EGTA, $Mg^{2+}$, CsA or ADP. The positive control was 150 μM $Ca^{2+}$ and 6 mM Pi (■).

ANT pore formation is controlled by the binding of $Ca^{2+}$, cyclophilin D and adenine nucleotides under physiological conditions. The primary trigger for opening of the mitochondrial permeability transition pore is a rise in matrix $Ca^{2+}$ concentration. Chelation of $Ca^{2+}$ with EGTA blocks pore opening, as does an excess of other divalent metal ions such as $Mg^{2+}$. Both EGTA and $Mg^{2+}$ blocked GSAO-dependent swelling (FIG. 18). Binding of cyclophilin D to ANT is necessary for pore opening at sub-millimolar $Ca^{2+}$ concentrations. Cyclosporin A (CsA) blocks pore opening by binding to cyclophilin D and displacing it from ANT. In addition, ADP inhibits pore opening by binding to ANT and decreasing the sensitivity of the trigger site to $Ca^{2+}$. CsA and ADP blocked the effect of o-GSAO on pore opening (FIG. 19).

Example 12

Comparison of GSAO and o-GSAO

Cell Proliferation and Viability Assay

Method

BAE or human pancreatic carcinoma BxPC-3 cells were seeded at a density of $10^3$ cells per well into 96 well plates in DMEM containing 10% foetal bovine serum and allowed to adhere for 24 h. Cells were washed and incubated with DMEM containing 10% foetal bovine serum and GSAO or o-GSAO and cultured for a further 48 h. Some BAE cells were arrested for 24 h in medium containing 0.25% serum and cultured for a further 48 h in medium containing 0.25% or 10% serum, in the presence of GSAO or o-GSAO. Viable attached cells were determined using MTT.

Figures 20A, 20B:
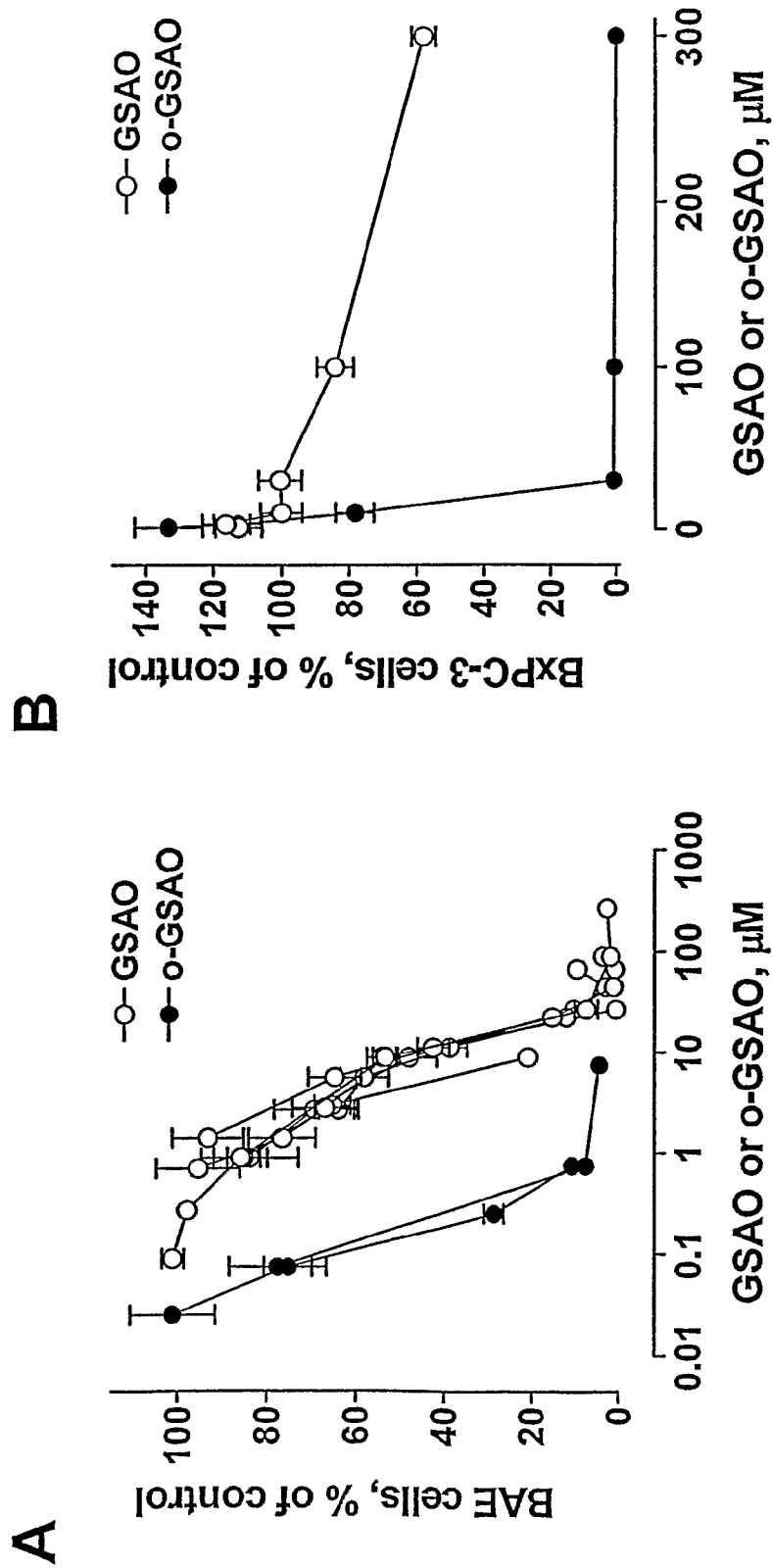
FIG. 20. Number of attached BAE (part A) or BxPC-3 (part B) cells remaining after 48 h incubation in medium containing 10% serum with GSAO (●) or o-GSAO (○). Each data point is the mean±SE of triplicate determinations. Results for BAE cells are from 6 (GSAO) or 2 (o-GSAO) different experiments.
Figures 21A, 21B:
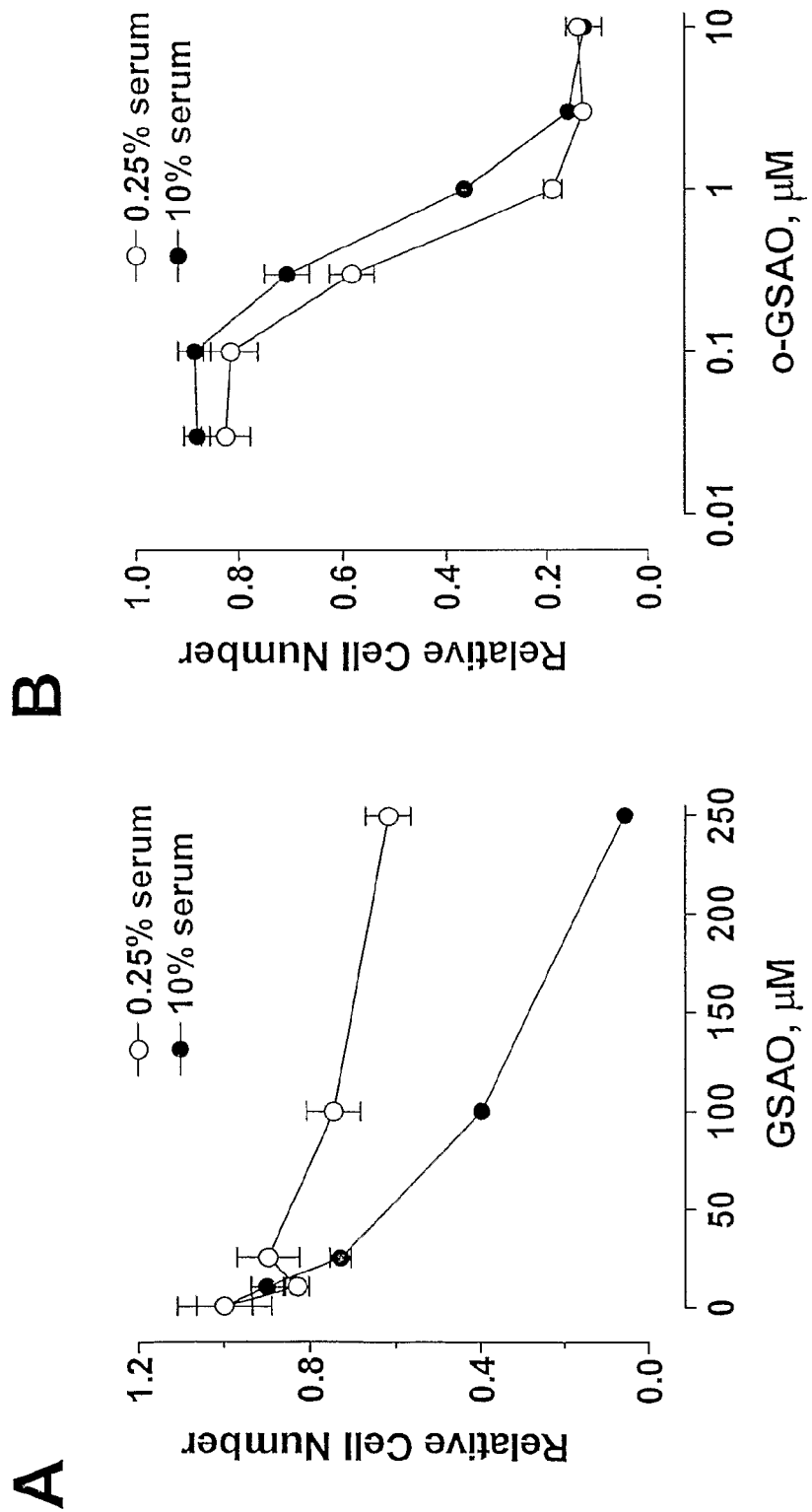
FIG. 21. Number of attached BAE cells remaining after 48 h incubation in medium containing 0.25% (○) or 10% (●) serum with GSAO (A) or o-GSAO (B). Each data point is the mean±SE of triplicate determinations.

Results o-GSAO is ~50-times more effective than GSAO at inhibiting proliferation of BAE cells. The $IC_{50}$ for proliferation arrest of BAE cells was 8.3±2.1 μM and 0.16±0.03 μM for GSAO and o-GSAO, respectively (FIG. 20A). o-GSAO, like GSAO, was a selective inhibitor of BAE compared to BxPC-3 cell proliferation. The $IC_{50}$ for proliferation arrest of BxPC-3 cells was >300 μM and ~2 μM for GSAO and o-GSAO, respectively (FIG. 20B). In contrast to GSAO, however, o-GSAO was not selective for proliferating (angiogenic) endothelial cells (FIG. 21). O-GSAO reduced the viability of proliferating and growth-quiescent endothelial cells equally well. The response to o-GSAO was very similar to PAO in this experiment (see Don et al., 2003).

Example 13a

Comparison of GSAO and o-GSAO

Primary Tumour Growth Assay

Method

Female 7 to 9 week old Balb C nude were used (UNSW Biological Resource Centre). Mice were held in groups of 3 to 5 at a 12 h day and night cycle and were given animal chow and water ad libidum. A suspension of $2.5 \times 10^6$ BxPC-3 cells in 0.2 mL of PBS was injected subcutaneously in the proximal midline. Tumours were allowed to establish and grow to a size of ~40 mm³ after which they were randomised into four groups. Tumour volume was calculated using the relationship, $a \cdot b^2 \cdot 0.52$, where a is the longest and b the shortest diameter. Animals were treated with either GSAO or o-GSAO at a dose 1 or 10 mg/kg/day in 0.1 mL of PBS. The compounds were administered subcutaneously at a site distant from the tumour. Tumour volume and animal weight was measured every 2 or 3 days.

Results

Figure 22:
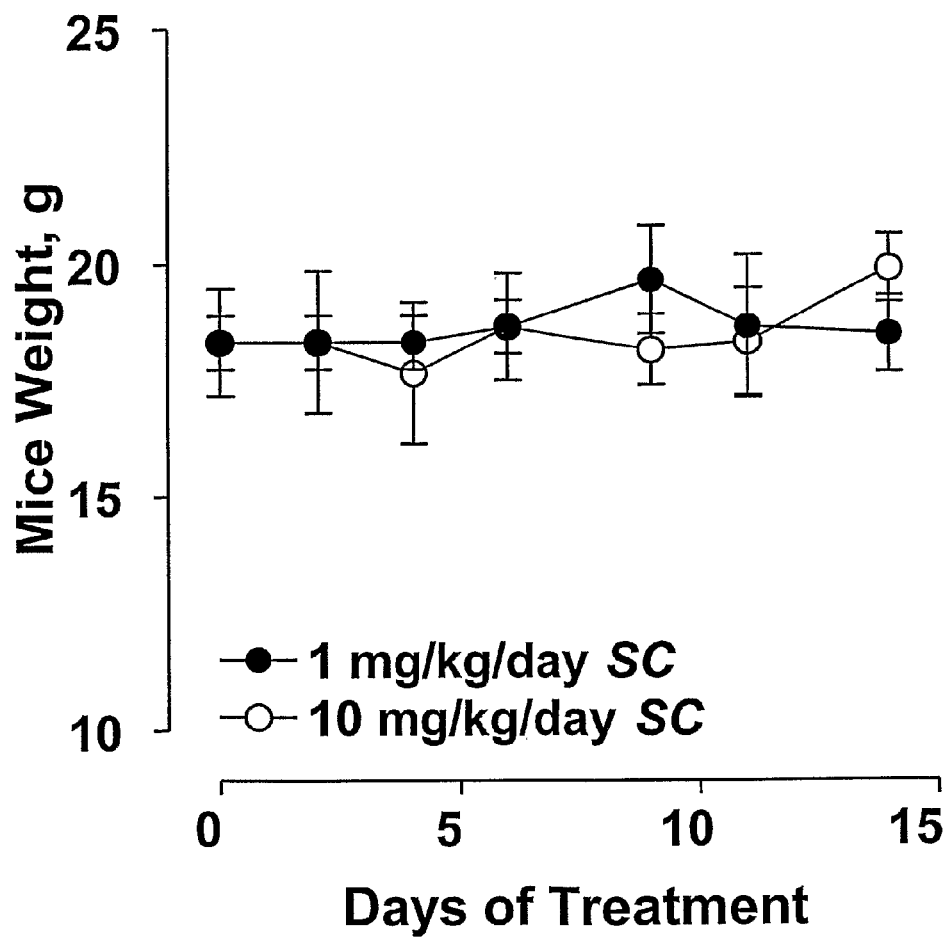
FIG. 22. Toxicity of o-GSAO. Balb-C mice (6-8 week old, 3 per group) were treated subcutaneously with 1 or 10 mg/kg/day of o-GSAO in 0.1 mL of PBS. The data points are the mean±SE of the mice weights.

There were short-term behavioural side-effects of administration of o-GSAO to Balb C mice, although there was no weight loss observed. The results are presented in Table 3 and FIG. 22.

TABLE 3

Side-effects of o-GSAO administration.

| Day | 1 mg/kg o-GSAO | 10 mg/kg o-GSAO |
|---|---|---|
| 1 | nil | ruffled fur; hyperactivity; mild tremors[a] |
| 2 | ruffled fur; mild hyperactivity[b] | ruffled fur; mild hyperactivity[b] |
| 3 | ruffled fur; mild hyperactivity[b] | ruffled fur; mild hyperactivity[b] |
| 4 | ruffled fur; mild hyperactivity[b] | ruffled fur; mild hyperactivity[b] |
| 5 | ruffled fur; hyperactivity; clonic movements of the hind limbs[b] | ruffled fur; hyperactivity; clonic movements of the hind limbs[b] |
| 6 | ruffled fur; hyperactivity; clonic movements of the hind limbs[b] | ruffled fur; hyperactivity; clonic movements of the hind limbs[b] |
| 7 | ruffled fur; hyperactivity; clonic movements of the hind limbs[b] | ruffled fur; hyperactivity; clonic movements of the hind limbs[b] |
| 8 | ruffled fur; hyperactivity[b] | ruffled fur; hyperactivity[b] |
| 9 | ruffled fur; mild hyperactivity[b] | ruffled fur; mild hyperactivity[b] |
| 10 | ruffled fur; mild hyperactivity[b] | ruffled fur; mild hyperactivity[b] |
| 11 | ruffled fur; mild hyperactivity[b] | ruffled fur; mild hyperactivity[b] |
| 13 | nil | skin necrosis at the injection site |
| 14 | nil | skin necrosis at the injection site |

[a]behavioural signs appeared 20-25 min after injection and lasted for 5-10 min.
[b]behavioural signs appeared 10-15 min after injection and lasted for 5-10 min.

Example 13b

Comparison of GSAO and o-GSAO

Anti-Tumour Efficacy

Method

Balb-C nude mice bearing ~40 mm³ BxPC-3 tumours were randomised into four groups (n=10 or 11 per group) and treated subcutaneously with either GSAO (part A) or o-GSAO (part B) at 1 or 10 mg/kg/day in 0.1 mL of PBS. Parts C and D are the mice weights for the respective groups, where the arrow indicates start of treatment. The data points are the mean±SE of the tumour volumes or mice weights. Treatment with 10 mg/kg o-GSAO (part B) was stopped at day 14 due to necrosis and inflammation at sites of injection in 7 out of 11 mice (3/11 with severe ulcers, 4/11 with medium ulcers). There was also some weight loss in this group (part D).

Results

Figures 23A, 23B, 23C, 23D:
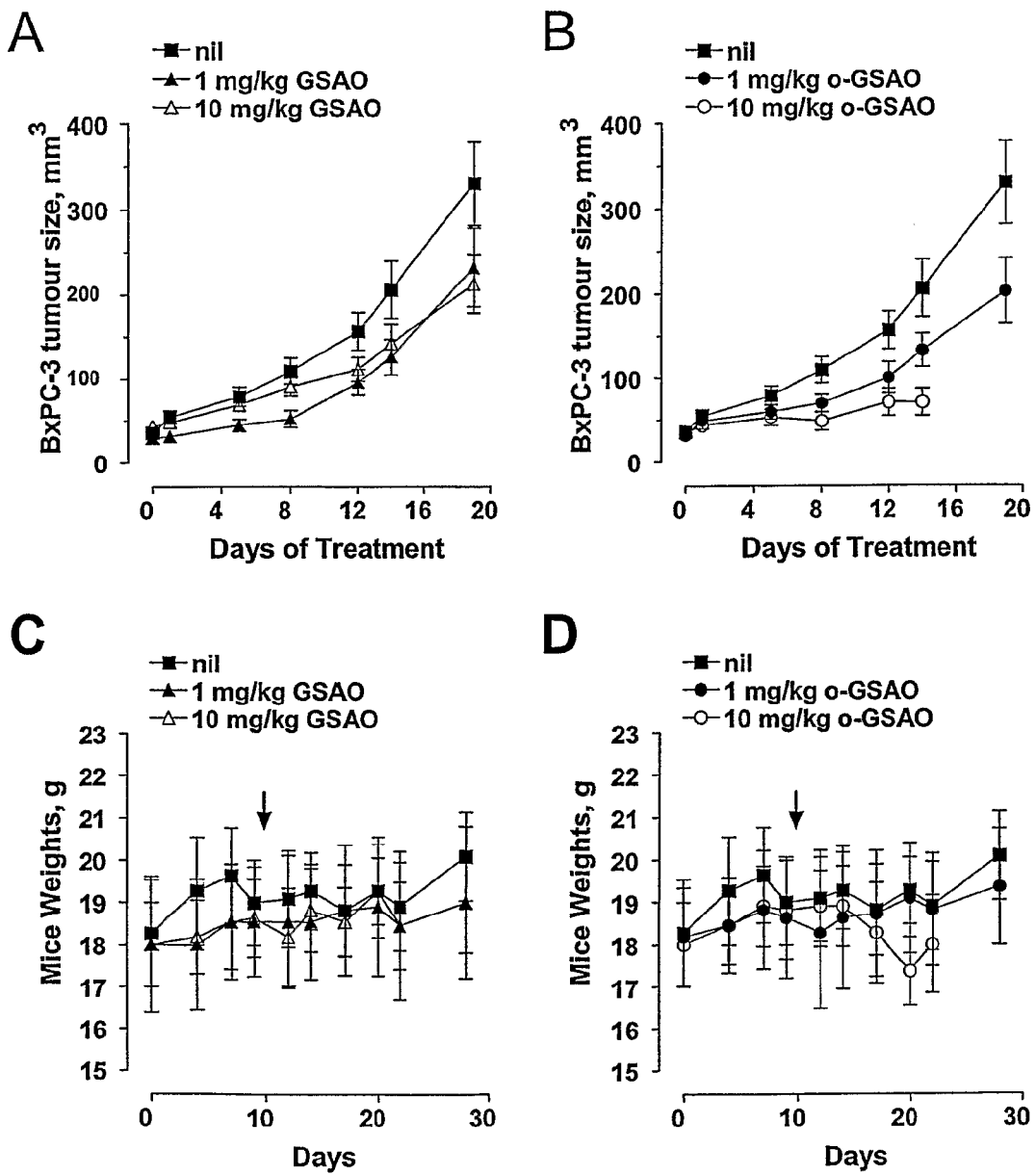
FIG. 23. Anti-tumour efficacy of o-GSAO compared to GSAO. Balb-C nude mice bearing ~40 mm³ BxPC-3 tumours were randomised into four groups (n=10 or 11 per group) and treated subcutaneously with either GSAO (part A) or o-GSAO (part B) at 1 or 10 mg/kg/day in 0.1 mL of PBS. Parts C and D are the mice weights for the respective groups, where the arrow indicates start of treatment. The data points are the mean±SE of the tumour volumes or mice weights. Treatment with 10 mg/kg o-GSAO (part B) was stopped at day 14 due to necrosis and inflammation at sites of injection in 7 out of 11 mice (3/11 with severe ulcers, 4/11 with medium ulcers). There was also some weight loss in this group (part D).

Short-term behavioural side-effects were observed following administration of o-GSAO to Balb C mice and also thickening of the skin and occasional necrosis with repeated injections in the same area. The behavioural side-effects were not observed in the Balb C nude mice in the tumour experiment (Example 13a), although the skin necrosis was more severe in these mice. Indeed, treatment with 10 mg/kg o-GSAO was stopped at day 14 due to severe necrosis and inflammation at injection sites in 7 of 11 animals. The only weight loss observed in either mice strain was in this group. These side-effects were not observed with GSAO administration (FIG. 23).

In summary, o-GSAO is more efficacious than GSAO in vitro, but has side-effects that are not apparent with GSAO administration. Unlike GSAO, o-GSAO is not selective for proliferating versus growth-quiescent endothelial cells.

REFERENCES

Ades, E. W., Candal, F. J., Swerlick, R. A., George, V. G., Summers, S., Bosse, D. C., and Lawley, T. J. HMEC-1: Establishment of an immortalized human microvascular endothelial cell line. J. Invest. Dermatol. 99, 683-690, 1992.

Carmeliet, P. and Jain, R. K. Angiogenesis in cancer and other diseases. Nature 407, 249-257, 2000.

Crompton, M. The mitochondrial permeability transition pore and its role in cell death. Biochem. J. 341, 233-249, 1999.

Crompton, M., Costi, A. and Hayat, L. Evidence for the presence of a reversible $Ca^{2+}$-dependent pore activated by oxidative stress in heart mitochondria. Biochem. J. 245, 915-918, 1987.

Crompton, M., Ellinger, H. and Costi, A. Inhibition by cyclosporin A of a $Ca^{2+}$-dependent pore in heart mitochondria activated by inorganic phosphate and oxidative stress. Biochem. J. 255, 357-360, 1988.

Donoghue, N., Yam, P. T. W., Jiang, X., and Hogg, P. J. Presence of closely spaced protein thiols on the surface of mammalian cells. Protein Sci. 9, 2436-2445, 2000.

Folkman, J. Angiogenesis and its inhibitors. In Important Advances in Oncology, DeVita, V. T., Hellman, S., and Rosenberg, S., eds. (J.B. Lippincott Company, PD) pp. 42-62, 1985.

Halestrap, A. P., McStay, G. P., Clarke, S. J. The permeability transition pore complex: another view. Biochimie 84, 153-66, 2002.

Halestrap, A. P., Woodfield, K. Y. and Connern, C. P. Oxidative stress, thiol reagents, and membrane potential modulate the mitochondrial permeability transition by affecting nucleotide binding to the adenine nucleotide translocase. J. Biol. Chem. 272, 3346-3354, 1997.

Hanahan, D. and Folkman, J. Patterns and emerging mechanisms of the angiogenic switch during tumourigenesis. Cell 86, 353-364, 1996.

Haworth, R. A. and Hunter, D. R. Control of the mitochondrial permeability transition pore by high-affinity ADP binding at the ADP/ATP translocase in permeabilized mitochondria. J. Bioenerg. Biomembr. 32, 91-96, 2000.

Haworth, R. A. and Hunter, D. R. The $Ca^{2+}$-induced membrane transition in mitochondria. II. Nature of the $Ca^{2+}$ trigger site. Arch. Biochem. Biophys. 195, 460-467, 1979.

Holmgren, L., O'Reilly, M. S., and Folkman, J. Dormancy of micrometastases: balanced proliferation and apoptosis in the presence of angiogenesis suppression. Nature Med. 1, 149-153, 1995.

Hunter, D. R. and Haworth, R. A. The $Ca^{2+}$-induced membrane transition in mitochondria. I. The protective mechanisms. Arch. Biochem. Biophys. 195, 453-459, 1979.

Majima, E., Yamaguchi, N., Chuman, H., Shinohara, Y., Ishida, M., Goto, S, and Terada, H. Binding of the fluorescein derivative eosin Y to the mitochondrial ADP/ATP carrier: characterization of the adenine nucleotide binding site. Biochemistry 37, 424-432, 1998.

Nguyen, M., Shing, Y., and Folkman, J. Quantitation of angiogenesis and antiangiogenesis in the chick embryo chorioallantoic membrane. Microvascular Res. 47, 31-40, 1994.

Oliver, M. H., Harrison, N. K., Bishop, J. E., Cole, P. J., and Laurent, G. J. A rapid and convenient assay for counting cells cultured in microwell plates: application for assessment of growth factors. J. Cell Sci. 92, 513-518, 1989.

O'Reilly, M. S., Boehm, T., Shing, Y., Fukai, N., Vasios, G., Lane, W. S., Flynn, E., Birkhead, J. R., Olsen, B. R., and Folkman J. Endostatin: an endogenous inhibitor of angiogenesis and tumour growth. Cell 88, 277-285, 1997.

Petit, J. M., Maftah, A., Ratinaud, M. H., and Julien, R. 10N-nonyl acridine orange interacts with cardiolipin and allows the quantification of this phospholipid in isolated mitochondria. Eur. J. Biochem. 209, 267-273, 1992.

Schnaitman, C. and Greenawalt, J. W. Enzymatic properties of the inner and outer membranes of rat liver mitochondria. J. Cell Biol. 38, 158-75, 1968.

Smiley, S. T., Reers, M., Mottola-Hartshorn, C., Lin, M., Chen, A., Smith, T. W., Steele, G. D., and Chen, L. B. Intracellular heterogeneity in mitochondrial membrane potentials revealed by a J-aggregate-forming lipophilic cation JC-1. Proc. Natl. Acad. Sci. USA 88, 3671-3675, 1991.

Vanden Hoek, T. L., Becker, L. B., Shao, Z., Li, C., and Schumacker, P. T. Reactive oxygen species released from mitochondria during brief hypoxia induce preconditioning in cardiomyocytes. J. Biol. Chem. 29, 18092-18098, 1998.

Zanetti, M., Zwacka, R. M., Engelhardt, J. F., Katusic, Z. S., and O'Brien, T. Superoxide anions and endothelial cell proliferation in normoglycemia and hyperglycemia. Arterioscler. Thromb. Vasc. Biol. 21, 195-200, 2001.

I claim:

1. A compound selected from the group consisting of:

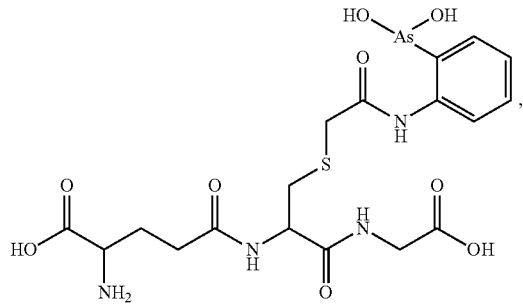

-continued

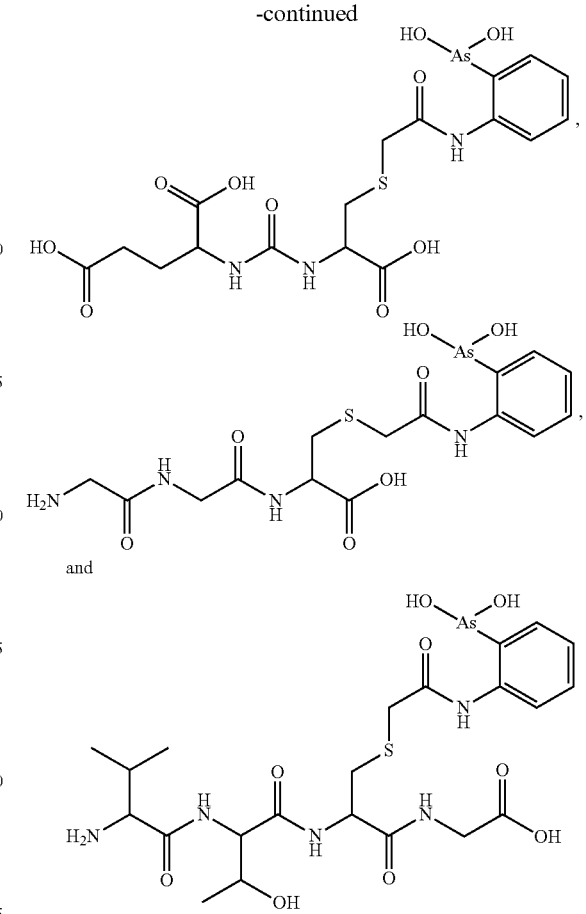

or a pharmaceutically acceptable salt thereof.

2. A pharmaceutical composition comprising a compound according to claim 1 together with a pharmaceutically acceptable carrier, adjuvant and/or diluent.

* * * * *